(12) United States Patent
Wingfield et al.

(10) Patent No.: US 11,827,669 B2
(45) Date of Patent: Nov. 28, 2023

(54) ANTIBODIES AND METHODS FOR THE DIAGNOSIS AND TREATMENT OF HEPATITIS B VIRUS INFECTION

(71) Applicant: THE USA, AS REPRESENTED BY THE SECRETARY, DEPT. OF HEALTH AND HUMAN SERVICES, Bethesda, MD (US)

(72) Inventors: Paul T. Wingfield, Bethesda, MD (US); Norman R. Watts, Bethesda, MD (US); Alasdair C Steven, Bethesda, MD (US)

(73) Assignee: THE USA, AS REPRESENTED BY THE SECRETARY, DEPT. OF HEALTH AND HUMAN SERVICES, Bethesda, MD (US)

( * ) Notice: Subject to any disclaimer, the term of this patent is extended or adjusted under 35 U.S.C. 154(b) by 331 days.

(21) Appl. No.: 16/631,290

(22) PCT Filed: Jul. 19, 2018

(86) PCT No.: PCT/US2018/042870
§ 371 (c)(1),
(2) Date: Jan. 15, 2020

(87) PCT Pub. No.: WO2019/018629
PCT Pub. Date: Jan. 24, 2019

(65) Prior Publication Data
US 2021/0380668 A1 Dec. 9, 2021

Related U.S. Application Data

(60) Provisional application No. 62/534,603, filed on Jul. 19, 2017.

(51) Int. Cl.
| | | |
|---|---|---|
| *C07K 16/08* | (2006.01) | |
| *A61K 47/68* | (2017.01) | |
| *A61K 45/06* | (2006.01) | |
| *A61K 39/00* | (2006.01) | |
| *G01N 33/569* | (2006.01) | |

(52) U.S. Cl.
CPC ............ *C07K 16/082* (2013.01); *A61K 45/06* (2013.01); *A61K 47/6839* (2017.08); *G01N 33/56994* (2013.01); *A61K 2039/585* (2013.01); *C07K 2317/24* (2013.01); *C07K 2317/31* (2013.01); *C07K 2317/33* (2013.01); *C07K 2317/55* (2013.01); *C07K 2317/565* (2013.01); *C07K 2317/92* (2013.01); *G01N 2333/02* (2013.01); *G01N 2469/10* (2013.01); *G01N 2800/26* (2013.01)

(58) Field of Classification Search
None
See application file for complete search history.

(56) References Cited

U.S. PATENT DOCUMENTS

2013/0136744 A1 5/2013 Bouche et al.

FOREIGN PATENT DOCUMENTS

| WO | WO 97/35204 | 9/1997 |
|---|---|---|
| WO | WO 01/81421 | 11/2001 |
| WO | 2014145252 A2 | 9/2014 |
| WO | 2017194782 A2 | 11/2017 |

OTHER PUBLICATIONS

Ferns et al. "Monoclonal Antibodies to Hepatitis Be Antigen (HBeAg) Derived from Hepatitis B Core Antigen (HBcAg): Their Use in Characterization and Detection of HBeAg," Journal of General Virology, May 1984, vol. 65, No. 5, pp. 899-908.
Rudikoff et al. "Single amino acid substitution altering antigen-binding specificity," PNAS, Mar. 1982, vol. 79, pp. 1979-1983.
Walsh et al. "Hepatitis B Precore Protein: Pathogenic Potential and Therapeutic Promise," Yonsei Medical Journal, Sep. 2012, vol. 53, No. 5, pp. 875-885.
Watts et al. "Molecular Basis for the High Degree of Antigenic Cross-Reactivity between Hepatitis B Virus Capsids (HBcAg) and Dimeric Capsid-Related Protein (HBeAg): Insights into the Enigmatic Nature of the e-Antigen," Journal of Molecular Biology, vol. 398, No. 4, pp. 530-541.
Xun et al. "Intracellular-delivery of a single-chain antibody against hepatitis B core protein via cell-penetrating peptide inhibits hepatitis B virus replication in vitro," International Journal of Molecular Medicine, Feb. 2013, vol. 31, No. 2, pp. 369-376.
Zhuang et al. "Chimeric rabbit/human Fab antibodies against the hepatitis B e-antigen and their potential applications in assays, characterization, and therapy," Journal of Biological Chemistry, Oct. 2017, vol. 292, No. 40, pp. 16760-16772.
International Preliminary Report on Patentability for International (PCT) Patent Application No. PCT/US2018/042870, dated Jan. 30, 2020 13 pages.
Offcial Action for European Patent Application No. 18750051.7, dated Feb. 26, 2020 3 pages.
International Search Report and Written Opinion prepared by the European Patent Office dated Nov. 20, 2018, for International Application No. PCT/US2018/042870.
Mathieu Dondelinger et al: "Understanding the Significance and Implications of Antibody Numbering and Antigen-Binding Surface/Residue Definition", Frontiers in Immunology,vol. 9, Oct. 16, 2018 (Oct. 16, 2018), pp. 1-15.
European examination report dated Jul. 16, 2021 in related European Application No. 18750051.7, 14 pages.
Kaspar, M. et al. "Fibronectin as target for tumor therapy", Int J Cancer. Mar. 15, 2006;118(6): pp. 1331-1339.
Chinese Office Action dated Jan. 28, 2023 in Chinese Application No. 201880059238.8, 5 pages.

*Primary Examiner* — Marianne P Allen
(74) *Attorney, Agent, or Firm* — Fox Rothschild LLP

(57) ABSTRACT

Antibodies and compositions of matter useful for the detection, diagnosis and treatment of Hepatitis B Virus infection in mammals, and to methods of using those compositions of matter for the same.

8 Claims, 12 Drawing Sheets
Specification includes a Sequence Listing.

HBV c-antigen (HBcAg)

MDIDPYKEFG ATVELLSFLP SDFFPSVRDL LDTAAALYRD
ALESPEHCSP HHTALRQAIL CWGDLMTLAT WVGTNLEDPA
SRDLVVSYVN TNVGLKFRQL LWFHISCLTF GRETVLEYLV
SFGVWIRTPP AYRPPNAPIL STLPETTVVR RRGRSPRRRT
PSPRRRRSQS PRRRRSQSRE SQC (SEQ ID NO.1)

Number of Amino Acids : 183

Molecular Weight: 21,041

*FIG. 1A*

HBV e-antigen (HBeAg)

(-10)        (-1)
SKLCLGWLWG MDIDPYKEFG ATVELLSFLP SDFFPSVRDL
LDTAAALYRD ALESPEHCSP HHTALRQAIL CWGDLMTLAT
WVGTNLEDPA SRDLVVSYVN TNVGLKFRQL LWFHISCLTF
GRETVLEYLV SFGVWIRTPP AYRPPNAPIL STLPETTVV(R)(R)
(SEQ ID NO:2)

Number of Amino Acids: 159

Molecular Weight: 17,914

*FIG. 1B*

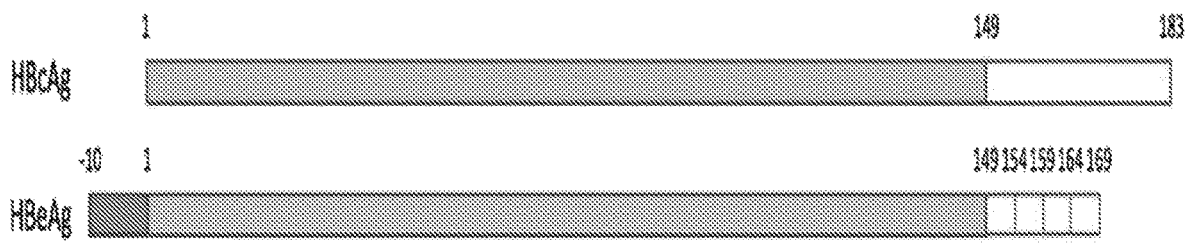

*FIG. 1C*

SEQUENCE LISTING

<160> NUMBER OF SEQ ID NOS: 158

<210> SEQ ID NO 1
<211> LENGTH: 183
<212> TYPE: PRT
<213> ORGANISM: Unknown
<220> FEATURE:
<223> OTHER INFORMATION: Hepadnaviridae

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

```
Glu Thr Thr Val Val Arg Arg Gly Arg Ser Pro Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 2
<211> LENGTH: 161
<212> TYPE: PRT
<213> ORGANISM: Unknown
<220> FEATURE:
<223> OTHER INFORMATION: Hepadnaviridae

<400> SEQUENCE: 2

Ser Lys Leu Cys Leu Gly Trp Leu Trp Gly Met Asp Ile Asp Pro Tyr
1               5                   10                  15

Lys Glu Phe Gly Ala Thr Val Glu Leu Leu Ser Phe Leu Pro Ser Asp
                20                  25                  30

Phe Phe Pro Ser Val Arg Asp Leu Leu Asp Thr Ala Ala Ala Leu Tyr
            35                  40                  45

Arg Asp Ala Leu Glu Ser Pro Glu His Cys Ser Pro His His Thr Ala
50                  55                  60

Leu Arg Gln Ala Ile Leu Cys Trp Gly Asp Leu Met Thr Leu Ala Thr
65                  70                  75                  80

Trp Val Gly Thr Asn Leu Glu Asp Pro Ala Ser Arg Asp Leu Val Val
                85                  90                  95

Ser Tyr Val Asn Thr Asn Val Gly Leu Lys Phe Arg Gln Leu Leu Trp
            100                 105                 110

Phe His Ile Ser Cys Leu Thr Phe Gly Arg Glu Thr Val Leu Glu Tyr
        115                 120                 125

Leu Val Ser Phe Gly Val Trp Ile Arg Thr Pro Pro Ala Tyr Arg Pro
    130                 135                 140

Pro Asn Ala Pro Ile Leu Ser Thr Leu Pro Glu Thr Thr Val Val Arg
145                 150                 155                 160

Arg

<210> SEQ ID NO 3
<211> LENGTH: 11
<212> TYPE: PRT
<213> ORGANISM: Unknown
<220> FEATURE:
<223> OTHER INFORMATION: Leporidae

<400> SEQUENCE: 3

Gln Ala Ser Gln Ser Ile Ser Ser Arg Leu Gly
1               5                   10

<210> SEQ ID NO 4
<211> LENGTH: 7
<212> TYPE: PRT
<213> ORGANISM: Unknown
<220> FEATURE:
<223> OTHER INFORMATION: Leporidae

<400> SEQUENCE: 4

Gly Ala Ser Thr Leu Thr Ser
1               5
```

```
<210> SEQ ID NO 5
<211> LENGTH: 10
<212> TYPE: PRT
<213> ORGANISM: Unknown
<220> FEATURE:
<223> OTHER INFORMATION: Leporidae

<400> SEQUENCE: 5

Leu Gly Ser Asp Thr Ser Asp Thr Thr Ala
1               5                   10

<210> SEQ ID NO 6
<211> LENGTH: 10
<212> TYPE: PRT
<213> ORGANISM: Unknown
<220> FEATURE:
<223> OTHER INFORMATION: Leporidae

<400> SEQUENCE: 6

Gly Ile Asp Leu Ser Ser Asn Ala Ile Ser
1               5                   10

<210> SEQ ID NO 7
<211> LENGTH: 12
<212> TYPE: PRT
<213> ORGANISM: Unknown
<220> FEATURE:
<223> OTHER INFORMATION: Leporidae

<400> SEQUENCE: 7

Ile Ile Tyr Gly Gly Ser Ile Pro Tyr Tyr Ser Arg
1               5                   10

<210> SEQ ID NO 8
<211> LENGTH: 15
<212> TYPE: PRT
<213> ORGANISM: Unknown
<220> FEATURE:
<223> OTHER INFORMATION: Leporidae

<400> SEQUENCE: 8

Gly Lys Ser Asp Gly Asp Gly Tyr Ala Ala Tyr Arg Leu Asp Pro
1               5                   10                  15

<210> SEQ ID NO 9
<211> LENGTH: 11
<212> TYPE: PRT
<213> ORGANISM: Unknown
<220> FEATURE:
<223> OTHER INFORMATION: Leporidae

<400> SEQUENCE: 9

Gln Ala Ser Gln Ser Ile Ser Ser Arg Leu Gly
1               5                   10

<210> SEQ ID NO 10
<211> LENGTH: 10
<212> TYPE: PRT
<213> ORGANISM: Unknown
<220> FEATURE:
<223> OTHER INFORMATION: Leporidae

<400> SEQUENCE: 10

Leu Gly Ser Asp Thr Ser Thr Asp Thr Ala
1               5                   10
```

```
<210> SEQ ID NO 11
<211> LENGTH: 7
<212> TYPE: PRT
<213> ORGANISM: Unknown
<220> FEATURE:
<223> OTHER INFORMATION: Leporidae

<400> SEQUENCE: 11

Gly Ala Ser Thr Leu Thr Ser
1               5

<210> SEQ ID NO 12
<211> LENGTH: 10
<212> TYPE: PRT
<213> ORGANISM: Unknown
<220> FEATURE:
<223> OTHER INFORMATION: Leporidae

<400> SEQUENCE: 12

Gly Ile Asp Leu Ser Ser Asn Ala Ile Ser
1               5                   10

<210> SEQ ID NO 13
<211> LENGTH: 12
<212> TYPE: PRT
<213> ORGANISM: Unknown
<220> FEATURE:
<223> OTHER INFORMATION: Leporidae

<400> SEQUENCE: 13

Ile Ile Tyr Gly Gly Ser Ile Pro Tyr Tyr Ser Arg
1               5                   10

<210> SEQ ID NO 14
<211> LENGTH: 15
<212> TYPE: PRT
<213> ORGANISM: Unknown
<220> FEATURE:
<223> OTHER INFORMATION: Leporidae

<400> SEQUENCE: 14

Gly Lys Ser Asp Gly Asp Gly Tyr Ala Ala Tyr Arg Leu Asp Pro
1               5                   10                  15

<210> SEQ ID NO 15
<211> LENGTH: 11
<212> TYPE: PRT
<213> ORGANISM: Unknown
<220> FEATURE:
<223> OTHER INFORMATION: Leporidae

<400> SEQUENCE: 15

Gln Ala Ser Gln Ser Ile Ser Ser Arg Leu Ala
1               5                   10

<210> SEQ ID NO 16
<211> LENGTH: 7
<212> TYPE: PRT
<213> ORGANISM: Unknown
<220> FEATURE:
<223> OTHER INFORMATION: Leporidae

<400> SEQUENCE: 16

Gly Ala Ser Thr Leu Ala Ser
1               5
```

```
<210> SEQ ID NO 17
<211> LENGTH: 10
<212> TYPE: PRT
<213> ORGANISM: Unknown
<220> FEATURE:
<223> OTHER INFORMATION: Leporidae

<400> SEQUENCE: 17

Leu Gly Ser Asp Thr Ser Thr Asn Thr Ala
1               5                   10

<210> SEQ ID NO 18
<211> LENGTH: 10
<212> TYPE: PRT
<213> ORGANISM: Unknown
<220> FEATURE:
<223> OTHER INFORMATION: Leporidae

<400> SEQUENCE: 18

Gly Ile Asp Leu Ser Ser Asn Ala Ile Thr
1               5                   10

<210> SEQ ID NO 19
<211> LENGTH: 12
<212> TYPE: PRT
<213> ORGANISM: Unknown
<220> FEATURE:
<223> OTHER INFORMATION: Leporidae

<400> SEQUENCE: 19

Ile Ile Tyr Gly Gly Ser Ile Pro Tyr Tyr Ser Arg
1               5                   10

<210> SEQ ID NO 20
<211> LENGTH: 15
<212> TYPE: PRT
<213> ORGANISM: Unknown
<220> FEATURE:
<223> OTHER INFORMATION: Leporidae

<400> SEQUENCE: 20

Gly Lys Ser Asp Gly Asp Gly Tyr Ala Ala Tyr Arg Leu Asp Pro
1               5                   10                  15

<210> SEQ ID NO 21
<211> LENGTH: 11
<212> TYPE: PRT
<213> ORGANISM: Unknown
<220> FEATURE:
<223> OTHER INFORMATION: Leporidae

<400> SEQUENCE: 21

Gln Ala Ser Gln Ser Val Ser Gly Arg Leu Gly
1               5                   10

<210> SEQ ID NO 22
<211> LENGTH: 7
<212> TYPE: PRT
<213> ORGANISM: Unknown
<220> FEATURE:
<223> OTHER INFORMATION: Leporidae

<400> SEQUENCE: 22

Gly Ala Ser Thr Leu Ala Ser
1               5
```

```
<210> SEQ ID NO 23
<211> LENGTH: 10
<212> TYPE: PRT
<213> ORGANISM: Unknown
<220> FEATURE:
<223> OTHER INFORMATION: Leporidae

<400> SEQUENCE: 23

Leu Gly Ser Asp Thr Ser Thr Asp Thr Ala
1               5                   10

<210> SEQ ID NO 24
<211> LENGTH: 10
<212> TYPE: PRT
<213> ORGANISM: Unknown
<220> FEATURE:
<223> OTHER INFORMATION: Leporidae

<400> SEQUENCE: 24

Gly Ile Asp Leu Ser Ser Asn Ala Ile Ser
1               5                   10

<210> SEQ ID NO 25
<211> LENGTH: 12
<212> TYPE: PRT
<213> ORGANISM: Unknown
<220> FEATURE:
<223> OTHER INFORMATION: Leporidae

<400> SEQUENCE: 25

Ile Ile Tyr Gly Gly Ser Ile Ala Tyr Tyr Ser Arg
1               5                   10

<210> SEQ ID NO 26
<211> LENGTH: 15
<212> TYPE: PRT
<213> ORGANISM: Unknown
<220> FEATURE:
<223> OTHER INFORMATION: Leporidae

<400> SEQUENCE: 26

Gly Lys Ser Asp Gly Asp Gly Tyr Ala Ala Tyr Arg Leu Asp Pro
1               5                   10                  15

<210> SEQ ID NO 27
<211> LENGTH: 11
<212> TYPE: PRT
<213> ORGANISM: Unknown
<220> FEATURE:
<223> OTHER INFORMATION: Leporidae

<400> SEQUENCE: 27

Gln Ala Ser Gln Ser Ile Ser Ser Arg Leu Gly
1               5                   10

<210> SEQ ID NO 28
<211> LENGTH: 7
<212> TYPE: PRT
<213> ORGANISM: Unknown
<220> FEATURE:
<223> OTHER INFORMATION: Leporidae

<400> SEQUENCE: 28

Gly Ala Ser Thr Leu Ala Ser
1               5
```

```
<210> SEQ ID NO 29
<211> LENGTH: 10
<212> TYPE: PRT
<213> ORGANISM: Unknown
<220> FEATURE:
<223> OTHER INFORMATION: Leporidae

<400> SEQUENCE: 29

Leu Gly Ser Asp Thr Ser Thr Asp Thr Ala
1               5                   10

<210> SEQ ID NO 30
<211> LENGTH: 10
<212> TYPE: PRT
<213> ORGANISM: Unknown
<220> FEATURE:
<223> OTHER INFORMATION: Leporidae

<400> SEQUENCE: 30

Gly Ile Asp Leu Ser Thr Asn Ala Ile Ser
1               5                   10

<210> SEQ ID NO 31
<211> LENGTH: 12
<212> TYPE: PRT
<213> ORGANISM: Unknown
<220> FEATURE:
<223> OTHER INFORMATION: Leporidae

<400> SEQUENCE: 31

Ile Ile Tyr Gly Gly Ser Ile Ser Tyr Tyr Ser Ser
1               5                   10

<210> SEQ ID NO 32
<211> LENGTH: 15
<212> TYPE: PRT
<213> ORGANISM: Unknown
<220> FEATURE:
<223> OTHER INFORMATION: Leporidae

<400> SEQUENCE: 32

Gly Lys Ser Asp Gly Asp Gly Tyr Ala Ala Tyr Arg Leu Asp Pro
1               5                   10                  15

<210> SEQ ID NO 33
<211> LENGTH: 11
<212> TYPE: PRT
<213> ORGANISM: Unknown
<220> FEATURE:
<223> OTHER INFORMATION: Leporidae

<400> SEQUENCE: 33

Gln Ala Ser Gln Ser Ile Ser Ser Arg Leu Ala
1               5                   10

<210> SEQ ID NO 34
<211> LENGTH: 7
<212> TYPE: PRT
<213> ORGANISM: Unknown
<220> FEATURE:
<223> OTHER INFORMATION: Leporidae

<400> SEQUENCE: 34

Gly Ala Ser Thr Leu Ala Ser
1               5
```

```
<210> SEQ ID NO 35
<211> LENGTH: 10
<212> TYPE: PRT
<213> ORGANISM: Unknown
<220> FEATURE:
<223> OTHER INFORMATION: Leporidae

<400> SEQUENCE: 35

Leu Gly Ser Asp Thr Ser Asp Thr Thr Ala
1               5                   10

<210> SEQ ID NO 36
<211> LENGTH: 10
<212> TYPE: PRT
<213> ORGANISM: Unknown
<220> FEATURE:
<223> OTHER INFORMATION: Leporidae

<400> SEQUENCE: 36

Gly Ile Asp Leu Ser Ser Asn Ala Ile Ser
1               5                   10

<210> SEQ ID NO 37
<211> LENGTH: 12
<212> TYPE: PRT
<213> ORGANISM: Unknown
<220> FEATURE:
<223> OTHER INFORMATION: Leporidae

<400> SEQUENCE: 37

Ile Ile Tyr Gly Gly Ser Ile Ala Tyr Tyr Pro Thr
1               5                   10

<210> SEQ ID NO 38
<211> LENGTH: 15
<212> TYPE: PRT
<213> ORGANISM: Leporidae

<400> SEQUENCE: 38

Gly Lys Ser Asp Gly Asp Gly Tyr Ala Ala Tyr Arg Leu Asp Pro
1               5                   10                  15

<210> SEQ ID NO 39
<211> LENGTH: 11
<212> TYPE: PRT
<213> ORGANISM: Unknown
<220> FEATURE:
<223> OTHER INFORMATION: Leporidae

<400> SEQUENCE: 39

Gln Ala Ser Gln Ser Ile Ser Ser Arg Leu Ala
1               5                   10

<210> SEQ ID NO 40
<211> LENGTH: 7
<212> TYPE: PRT
<213> ORGANISM: Unknown
<220> FEATURE:
<223> OTHER INFORMATION: Leporidae

<400> SEQUENCE: 40

Gly Ala Ser Thr Leu Ala Ser
1               5
```

```
<210> SEQ ID NO 41
<211> LENGTH: 10
<212> TYPE: PRT
<213> ORGANISM: Unknown
<220> FEATURE:
<223> OTHER INFORMATION: Leporidae

<400> SEQUENCE: 41

Leu Gly Ser Asp Thr Ser Thr Asn Thr Ala
1               5                   10

<210> SEQ ID NO 42
<211> LENGTH: 10
<212> TYPE: PRT
<213> ORGANISM: Unknown
<220> FEATURE:
<223> OTHER INFORMATION: Leporidae

<400> SEQUENCE: 42

Gly Ile Asp Leu Asn Ser Asn Ala Ile Thr
1               5                   10

<210> SEQ ID NO 43
<211> LENGTH: 12
<212> TYPE: PRT
<213> ORGANISM: Unknown
<220> FEATURE:
<223> OTHER INFORMATION: Leporidae

<400> SEQUENCE: 43

Ile Ile Tyr Gly Gly Ser Ile Ser Tyr Tyr Pro Ser
1               5                   10

<210> SEQ ID NO 44
<211> LENGTH: 15
<212> TYPE: PRT
<213> ORGANISM: Unknown
<220> FEATURE:
<223> OTHER INFORMATION: Leporidae

<400> SEQUENCE: 44

Gly Lys Ser Asp Gly Asp Gly Tyr Ala Ala Tyr Arg Leu Asp Pro
1               5                   10                  15

<210> SEQ ID NO 45
<211> LENGTH: 11
<212> TYPE: PRT
<213> ORGANISM: Unknown
<220> FEATURE:
<223> OTHER INFORMATION: Leporidae

<400> SEQUENCE: 45

Gln Ala Ser Gln Ser Ile Ser Arg Arg Leu Ala
1               5                   10

<210> SEQ ID NO 46
<211> LENGTH: 7
<212> TYPE: PRT
<213> ORGANISM: Unknown
<220> FEATURE:
<223> OTHER INFORMATION: Leporidae

<400> SEQUENCE: 46

Gly Ala Ser Thr Leu Ala Ser
1               5
```

```
<210> SEQ ID NO 47
<211> LENGTH: 10
<212> TYPE: PRT
<213> ORGANISM: Unknown
<220> FEATURE:
<223> OTHER INFORMATION: Leporidae

<400> SEQUENCE: 47

Leu Gly Ser Asp Thr Ser Thr Asn Thr Ala
1               5                   10

<210> SEQ ID NO 48
<211> LENGTH: 10
<212> TYPE: PRT
<213> ORGANISM: Unknown
<220> FEATURE:
<223> OTHER INFORMATION: Leporidae

<400> SEQUENCE: 48

Gly Ile Asp Leu Asn Ser Asn Ala Ile Thr
1               5                   10

<210> SEQ ID NO 49
<211> LENGTH: 12
<212> TYPE: PRT
<213> ORGANISM: Leporidae

<400> SEQUENCE: 49

Ile Ile Tyr Gly Gly Ser Ile Ser Tyr Tyr Pro Ser
1               5                   10

<210> SEQ ID NO 50
<211> LENGTH: 15
<212> TYPE: PRT
<213> ORGANISM: Unknown
<220> FEATURE:
<223> OTHER INFORMATION: Leporidae

<400> SEQUENCE: 50

Gly Lys Ser Asp Gly Asp Gly Tyr Ala Ala Tyr Arg Leu Asp Pro
1               5                   10                  15

<210> SEQ ID NO 51
<211> LENGTH: 11
<212> TYPE: PRT
<213> ORGANISM: Unknown
<220> FEATURE:
<223> OTHER INFORMATION: Leporidae

<400> SEQUENCE: 51

Gln Ala Ser Gln Ser Ile Ser Asn Arg Leu Ala
1               5                   10

<210> SEQ ID NO 52
<211> LENGTH: 7
<212> TYPE: PRT
<213> ORGANISM: Unknown
<220> FEATURE:
<223> OTHER INFORMATION: Leporidae

<400> SEQUENCE: 52

Gly Ala Ser Thr Leu Ala Ser
1               5
```

```
<210> SEQ ID NO 53
<211> LENGTH: 10
<212> TYPE: PRT
<213> ORGANISM: Unknown
<220> FEATURE:
<223> OTHER INFORMATION: Leporidae

<400> SEQUENCE: 53

Leu Gly Ser Asp Thr Ser Thr Asn Thr Ala
1               5                   10

<210> SEQ ID NO 54
<211> LENGTH: 10
<212> TYPE: PRT
<213> ORGANISM: Unknown
<220> FEATURE:
<223> OTHER INFORMATION: Leporidae

<400> SEQUENCE: 54

Gly Ile Asp Leu Ser Ser Tyr Ala Met Ala
1               5                   10

<210> SEQ ID NO 55
<211> LENGTH: 12
<212> TYPE: PRT
<213> ORGANISM: Unknown
<220> FEATURE:
<223> OTHER INFORMATION: Leporidae

<400> SEQUENCE: 55

Ile Ile Tyr Gly Gly Ser Ile Pro Tyr Tyr Ala Asn
1               5                   10

<210> SEQ ID NO 56
<211> LENGTH: 15
<212> TYPE: PRT
<213> ORGANISM: Unknown
<220> FEATURE:
<223> OTHER INFORMATION: Leporidae

<400> SEQUENCE: 56

Gly Thr Ser Asp Gly Glu Gly Tyr Ala Ala Tyr Arg Leu Asp Pro
1               5                   10                  15

<210> SEQ ID NO 57
<211> LENGTH: 11
<212> TYPE: PRT
<213> ORGANISM: Unknown
<220> FEATURE:
<223> OTHER INFORMATION: Leporidae

<400> SEQUENCE: 57

Gln Ala Ser Glu Asp Ile Ser Ser Arg Leu Ala
1               5                   10

<210> SEQ ID NO 58
<211> LENGTH: 7
<212> TYPE: PRT
<213> ORGANISM: Unknown
<220> FEATURE:
<223> OTHER INFORMATION: Leporidae

<400> SEQUENCE: 58

Gly Ala Ser Thr Leu Ala Ser
1               5
```

```
<210> SEQ ID NO 59
<211> LENGTH: 10
<212> TYPE: PRT
<213> ORGANISM: Unknown
<220> FEATURE:
<223> OTHER INFORMATION: Leporidae

<400> SEQUENCE: 59

Leu Gly Ser Tyr Ser Ser Ser Asp Thr Ala
1               5                   10

<210> SEQ ID NO 60
<211> LENGTH: 10
<212> TYPE: PRT
<213> ORGANISM: Unknown
<220> FEATURE:
<223> OTHER INFORMATION: Leporidae

<400> SEQUENCE: 60

Gly Ile Asp Leu Ser Ser Asn Ala Ile Ser
1               5                   10

<210> SEQ ID NO 61
<211> LENGTH: 12
<212> TYPE: PRT
<213> ORGANISM: Unknown
<220> FEATURE:
<223> OTHER INFORMATION: Leporidae

<400> SEQUENCE: 61

Ile Ile Tyr Gly Gly Ser Ile Pro Tyr Tyr Ser Arg
1               5                   10

<210> SEQ ID NO 62
<211> LENGTH: 15
<212> TYPE: PRT
<213> ORGANISM: Unknown
<220> FEATURE:
<223> OTHER INFORMATION: Leporidae

<400> SEQUENCE: 62

Gly Lys Ser Asp Gly Asp Gly Tyr Ala Ala Tyr Arg Leu Asp Pro
1               5                   10                  15

<210> SEQ ID NO 63
<211> LENGTH: 13
<212> TYPE: PRT
<213> ORGANISM: Unknown
<220> FEATURE:
<223> OTHER INFORMATION: Leporidae

<400> SEQUENCE: 63

Gln Ala Ser Glu Ser Val Ala Asn Asn Asn Arg Leu Ser
1               5                   10

<210> SEQ ID NO 64
<211> LENGTH: 7
<212> TYPE: PRT
<213> ORGANISM: Unknown
<220> FEATURE:
<223> OTHER INFORMATION: Leporidae

<400> SEQUENCE: 64

Gly Ala Ser Thr Leu Ala Ser
1               5
```

```
<210> SEQ ID NO 65
<211> LENGTH: 10
<212> TYPE: PRT
<213> ORGANISM: Unknown
<220> FEATURE:
<223> OTHER INFORMATION: Leporidae

<400> SEQUENCE: 65

Leu Gly Ser Ala Ser Ser Thr Asp Thr Ala
1               5                   10

<210> SEQ ID NO 66
<211> LENGTH: 10
<212> TYPE: PRT
<213> ORGANISM: Unknown
<220> FEATURE:
<223> OTHER INFORMATION: Leporidae

<400> SEQUENCE: 66

Gly Ile Asp Leu Ser Ser Asn Ala Ile Ser
1               5                   10

<210> SEQ ID NO 67
<211> LENGTH: 12
<212> TYPE: PRT
<213> ORGANISM: Unknown
<220> FEATURE:
<223> OTHER INFORMATION: Leporidae

<400> SEQUENCE: 67

Ile Ile Tyr Gly Gly Ser Ile Pro Tyr Tyr Ser Arg
1               5                   10

<210> SEQ ID NO 68
<211> LENGTH: 15
<212> TYPE: PRT
<213> ORGANISM: Unknown
<220> FEATURE:
<223> OTHER INFORMATION: Leporidae

<400> SEQUENCE: 68

Gly Lys Ser Asp Gly Asp Gly Tyr Ala Ala Tyr Arg Leu Asp Pro
1               5                   10                  15

<210> SEQ ID NO 69
<211> LENGTH: 11
<212> TYPE: PRT
<213> ORGANISM: Unknown
<220> FEATURE:
<223> OTHER INFORMATION: Leporidae

<400> SEQUENCE: 69

Gln Ala Ser Gln Ser Ile Gly Ser Arg Leu Gly
1               5                   10

<210> SEQ ID NO 70
<211> LENGTH: 7
<212> TYPE: PRT
<213> ORGANISM: Unknown
<220> FEATURE:
<223> OTHER INFORMATION: Leporidae

<400> SEQUENCE: 70

Gly Ala Ser Thr Leu Ala Ser
1               5
```

```
<210> SEQ ID NO 71
<211> LENGTH: 10
<212> TYPE: PRT
<213> ORGANISM: Unknown
<220> FEATURE:
<223> OTHER INFORMATION: Leporidae

<400> SEQUENCE: 71

Leu Gly Ser Asp Thr Ser Ser Ala Thr Ala
1               5                   10

<210> SEQ ID NO 72
<211> LENGTH: 10
<212> TYPE: PRT
<213> ORGANISM: Unknown
<220> FEATURE:
<223> OTHER INFORMATION: Leporidae

<400> SEQUENCE: 72

Gly Ile Asp Leu Val Thr Tyr Ala Met Ala
1               5                   10

<210> SEQ ID NO 73
<211> LENGTH: 12
<212> TYPE: PRT
<213> ORGANISM: Unknown
<220> FEATURE:
<223> OTHER INFORMATION: Leporidae

<400> SEQUENCE: 73

Ile Ile Tyr Gly Gly Gly Leu Ser Tyr Tyr Pro Ser
1               5                   10

<210> SEQ ID NO 74
<211> LENGTH: 15
<212> TYPE: PRT
<213> ORGANISM: Unknown
<220> FEATURE:
<223> OTHER INFORMATION: Leporidae

<400> SEQUENCE: 74

Gly Ser Ser Asp Gly Asp Gly Tyr Ala Ala Tyr Arg Leu Asp Pro
1               5                   10                  15

<210> SEQ ID NO 75
<211> LENGTH: 11
<212> TYPE: PRT
<213> ORGANISM: Unknown
<220> FEATURE:
<223> OTHER INFORMATION: Leporidae

<400> SEQUENCE: 75

Gln Ala Arg Gln Ser Ile Gly Ser Arg Leu Gly
1               5                   10

<210> SEQ ID NO 76
<211> LENGTH: 7
<212> TYPE: PRT
<213> ORGANISM: Unknown
<220> FEATURE:
<223> OTHER INFORMATION: Leporidae

<400> SEQUENCE: 76

Gly Ala Ser Thr Leu Ala Ser
1               5
```

```
<210> SEQ ID NO 77
<211> LENGTH: 10
<212> TYPE: PRT
<213> ORGANISM: Unknown
<220> FEATURE:
<223> OTHER INFORMATION: Leporidae

<400> SEQUENCE: 77

Leu Gly Ser Asp Thr Ser Ser Asn Thr Ala
1               5                   10

<210> SEQ ID NO 78
<211> LENGTH: 10
<212> TYPE: PRT
<213> ORGANISM: Unknown
<220> FEATURE:
<223> OTHER INFORMATION: Leporidae

<400> SEQUENCE: 78

Gly Ile Asp Leu Val Thr Ser Ala Met Ala
1               5                   10

<210> SEQ ID NO 79
<211> LENGTH: 12
<212> TYPE: PRT
<213> ORGANISM: Unknown
<220> FEATURE:
<223> OTHER INFORMATION: Leporidae

<400> SEQUENCE: 79

Ile Ile Tyr Gly Gly Gly Leu Ser Tyr Tyr Pro Ser
1               5                   10

<210> SEQ ID NO 80
<211> LENGTH: 15
<212> TYPE: PRT
<213> ORGANISM: Unknown
<220> FEATURE:
<223> OTHER INFORMATION: Leporidae

<400> SEQUENCE: 80

Gly Ser Ser Asp Gly Asp Gly Tyr Ala Ala Tyr Arg Leu Asp Pro
1               5                   10                  15

<210> SEQ ID NO 81
<211> LENGTH: 11
<212> TYPE: PRT
<213> ORGANISM: Unknown
<220> FEATURE:
<223> OTHER INFORMATION: Leporidae

<400> SEQUENCE: 81

Gln Ala Arg Gln Ser Ile Gly Ser Arg Leu Gly
1               5                   10

<210> SEQ ID NO 82
<211> LENGTH: 7
<212> TYPE: PRT
<213> ORGANISM: Unknown
<220> FEATURE:
<223> OTHER INFORMATION: Leporidae

<400> SEQUENCE: 82

Gly Ala Ser Thr Leu Ala Ser
1               5
```

```
<210> SEQ ID NO 83
<211> LENGTH: 10
<212> TYPE: PRT
<213> ORGANISM: Unknown
<220> FEATURE:
<223> OTHER INFORMATION: Leporidae

<400> SEQUENCE: 83

Leu Gly Ser Asp Thr Ser Ser Asn Thr Ala
1               5                   10

<210> SEQ ID NO 84
<211> LENGTH: 10
<212> TYPE: PRT
<213> ORGANISM: Unknown
<220> FEATURE:
<223> OTHER INFORMATION: Leporidae

<400> SEQUENCE: 84

Gly Ile Asp Leu Val Thr Ser Ala Met Ala
1               5                   10

<210> SEQ ID NO 85
<211> LENGTH: 12
<212> TYPE: PRT
<213> ORGANISM: Unknown
<220> FEATURE:
<223> OTHER INFORMATION: Leporidae

<400> SEQUENCE: 85

Ile Ile Gly Gly Gly Gly Leu Ser Tyr Tyr Pro Ser
1               5                   10

<210> SEQ ID NO 86
<211> LENGTH: 15
<212> TYPE: PRT
<213> ORGANISM: Unknown
<220> FEATURE:
<223> OTHER INFORMATION: Leporidae

<400> SEQUENCE: 86

Gly Ser Ser Asp Gly Asp Gly Tyr Ala Ala Tyr Arg Leu Asp Pro
1               5                   10                  15

<210> SEQ ID NO 87
<211> LENGTH: 11
<212> TYPE: PRT
<213> ORGANISM: Unknown
<220> FEATURE:
<223> OTHER INFORMATION: Leporidae

<400> SEQUENCE: 87

Gln Ala Ser Gln Ser Ile Gly Ser Arg Leu Gly
1               5                   10

<210> SEQ ID NO 88
<211> LENGTH: 7
<212> TYPE: PRT
<213> ORGANISM: Unknown
<220> FEATURE:
<223> OTHER INFORMATION: Leporidae

<400> SEQUENCE: 88

Gly Ala Ser Thr Leu Ala Ser
1               5
```

-continued

<210> SEQ ID NO 89
<211> LENGTH: 10
<212> TYPE: PRT
<213> ORGANISM: Unknown
<220> FEATURE:
<223> OTHER INFORMATION: Leporidae

<400> SEQUENCE: 89

Leu Gly Ser Asp Thr Ser Ser Ala Thr Ala
1               5                   10

<210> SEQ ID NO 90
<211> LENGTH: 10
<212> TYPE: PRT
<213> ORGANISM: Unknown
<220> FEATURE:
<223> OTHER INFORMATION: Leporidae

<400> SEQUENCE: 90

Gly Ile Asp Leu Ser Ser Asn Ala Val Ser
1               5                   10

<210> SEQ ID NO 91
<211> LENGTH: 12
<212> TYPE: PRT
<213> ORGANISM: Unknown
<220> FEATURE:
<223> OTHER INFORMATION: Leporidae

<400> SEQUENCE: 91

Ile Ile Tyr Gly Gly Gly Ile Thr Tyr Tyr Ala Ser
1               5                   10

<210> SEQ ID NO 92
<211> LENGTH: 15
<212> TYPE: PRT
<213> ORGANISM: Unknown
<220> FEATURE:
<223> OTHER INFORMATION: Leporidae

<400> SEQUENCE: 92

Gly Ser Ser Asp Gly Asp Gly Tyr Ala Ala Tyr Arg Leu Asp Pro
1               5                   10                  15

<210> SEQ ID NO 93
<211> LENGTH: 11
<212> TYPE: PRT
<213> ORGANISM: Unknown
<220> FEATURE:
<223> OTHER INFORMATION: Leporidae

<400> SEQUENCE: 93

Gln Ala Ser Glu Asp Ile Ser Ser Arg Leu Ala
1               5                   10

<210> SEQ ID NO 94
<211> LENGTH: 7
<212> TYPE: PRT
<213> ORGANISM: Unknown
<220> FEATURE:
<223> OTHER INFORMATION: Leporidae

<400> SEQUENCE: 94

Ser Ala Ser Thr Leu Ala Ser
1               5

```
<210> SEQ ID NO 95
<211> LENGTH: 10
<212> TYPE: PRT
<213> ORGANISM: Unknown
<220> FEATURE:
<223> OTHER INFORMATION: Leporidae

<400> SEQUENCE: 95

Leu Gly Ser Leu Ser Ser Ser Asp Thr Ala
1               5                   10

<210> SEQ ID NO 96
<211> LENGTH: 10
<212> TYPE: PRT
<213> ORGANISM: Unknown
<220> FEATURE:
<223> OTHER INFORMATION: Leporidae

<400> SEQUENCE: 96

Gly Ile Asp Leu Val Thr Ser Ala Met Ala
1               5                   10

<210> SEQ ID NO 97
<211> LENGTH: 12
<212> TYPE: PRT
<213> ORGANISM: Unknown
<220> FEATURE:
<223> OTHER INFORMATION: Leporidae

<400> SEQUENCE: 97

Ile Ile Tyr Gly Gly Gly Leu Ser Tyr Tyr Pro Ser
1               5                   10

<210> SEQ ID NO 98
<211> LENGTH: 15
<212> TYPE: PRT
<213> ORGANISM: Unknown
<220> FEATURE:
<223> OTHER INFORMATION: Leporidae

<400> SEQUENCE: 98

Gly Ser Ser Asp Gly Asp Gly Tyr Ala Ala Tyr Arg Leu Asp Pro
1               5                   10                  15

<210> SEQ ID NO 99
<211> LENGTH: 11
<212> TYPE: PRT
<213> ORGANISM: Unknown
<220> FEATURE:
<223> OTHER INFORMATION: Leporidae

<400> SEQUENCE: 99

Gln Ala Ser Gln Ser Ile Gly Asp Lys Leu Ala
1               5                   10

<210> SEQ ID NO 100
<211> LENGTH: 7
<212> TYPE: PRT
<213> ORGANISM: Unknown
<220> FEATURE:
<223> OTHER INFORMATION: Leporidae

<400> SEQUENCE: 100

Ser Ala Ser Val Leu Ala Ser
1               5
```

```
<210> SEQ ID NO 101
<211> LENGTH: 10
<212> TYPE: PRT
<213> ORGANISM: Unknown
<220> FEATURE:
<223> OTHER INFORMATION: Leporidae

<400> SEQUENCE: 101

Leu Gly Ser His Thr Ala Ser Asp Ile Ala
1               5                   10

<210> SEQ ID NO 102
<211> LENGTH: 10
<212> TYPE: PRT
<213> ORGANISM: Unknown
<220> FEATURE:
<223> OTHER INFORMATION: Leporidae

<400> SEQUENCE: 102

Gly Ile Asp Leu Thr Asn Tyr Ala Met Gly
1               5                   10

<210> SEQ ID NO 103
<211> LENGTH: 12
<212> TYPE: PRT
<213> ORGANISM: Unknown
<220> FEATURE:
<223> OTHER INFORMATION: Leporidae

<400> SEQUENCE: 103

Ile Ile Asn Met Gly Ile Phe Thr Ser Tyr Ala Thr
1               5                   10

<210> SEQ ID NO 104
<211> LENGTH: 13
<212> TYPE: PRT
<213> ORGANISM: Unknown
<220> FEATURE:
<223> OTHER INFORMATION: Leporidae

<400> SEQUENCE: 104

Gly Asn Gly Gly Asn Tyr Pro Phe Tyr Ala Ile Asp Ile
1               5                   10

<210> SEQ ID NO 105
<211> LENGTH: 11
<212> TYPE: PRT
<213> ORGANISM: Unknown
<220> FEATURE:
<223> OTHER INFORMATION: Leporidae

<400> SEQUENCE: 105

Gln Ala Ser Gln Ser Val Ser Ala Tyr Leu Ser
1               5                   10

<210> SEQ ID NO 106
<211> LENGTH: 7
<212> TYPE: PRT
<213> ORGANISM: Unknown
<220> FEATURE:
<223> OTHER INFORMATION: Leporidae

<400> SEQUENCE: 106

Arg Ala Ser Thr Leu Ala Ser
1               5
```

```
<210> SEQ ID NO 107
<211> LENGTH: 10
<212> TYPE: PRT
<213> ORGANISM: Unknown
<220> FEATURE:
<223> OTHER INFORMATION: Leporidae

<400> SEQUENCE: 107

Leu Gly Thr Tyr Ser Ser Ser Asn Thr Ala
1               5                   10

<210> SEQ ID NO 108
<211> LENGTH: 10
<212> TYPE: PRT
<213> ORGANISM: Unknown
<220> FEATURE:
<223> OTHER INFORMATION: Leporidae

<400> SEQUENCE: 108

Gly Phe Ser Leu Ser Thr His Ala Ile Ser
1               5                   10

<210> SEQ ID NO 109
<211> LENGTH: 12
<212> TYPE: PRT
<213> ORGANISM: Unknown
<220> FEATURE:
<223> OTHER INFORMATION: Leporidae

<400> SEQUENCE: 109

Ile Ile Phe Ala Ala Ser Ser Thr Tyr Tyr Ala Ser
1               5                   10

<210> SEQ ID NO 110
<211> LENGTH: 14
<212> TYPE: PRT
<213> ORGANISM: Unknown
<220> FEATURE:
<223> OTHER INFORMATION: Leporidae

<400> SEQUENCE: 110

Thr Ser Ile Ser Ser Asp Gly Phe Pro Asp Asn Phe Asn Ile
1               5                   10

<210> SEQ ID NO 111
<211> LENGTH: 11
<212> TYPE: PRT
<213> ORGANISM: Leporidae

<400> SEQUENCE: 111

Gln Ala Ser Gln Ser Ile Asp Gly Ala Leu Ser
1               5                   10

<210> SEQ ID NO 112
<211> LENGTH: 7
<212> TYPE: PRT
<213> ORGANISM: Unknown
<220> FEATURE:
<223> OTHER INFORMATION: Leporidae

<400> SEQUENCE: 112

Val Ala Ser Ser Leu Ala Ser
1               5
```

```
<210> SEQ ID NO 113
<211> LENGTH: 10
<212> TYPE: PRT
<213> ORGANISM: Unknown
<220> FEATURE:
<223> OTHER INFORMATION: Leporidae

<400> SEQUENCE: 113

Leu Gly Thr Tyr Asn Ala Phe Asp Arg Ala
1               5                   10

<210> SEQ ID NO 114
<211> LENGTH: 10
<212> TYPE: PRT
<213> ORGANISM: Unknown
<220> FEATURE:
<223> OTHER INFORMATION: Leporidae

<400> SEQUENCE: 114

Gly Phe Ser Leu Ser Asn Tyr Ala Met Ile
1               5                   10

<210> SEQ ID NO 115
<211> LENGTH: 12
<212> TYPE: PRT
<213> ORGANISM: Unknown
<220> FEATURE:
<223> OTHER INFORMATION: Leporidae

<400> SEQUENCE: 115

Ile Ile Gly Ser Gly Gly Ser Pro Tyr Tyr Ala Ser
1               5                   10

<210> SEQ ID NO 116
<211> LENGTH: 14
<212> TYPE: PRT
<213> ORGANISM: Unknown
<220> FEATURE:
<223> OTHER INFORMATION: Leporidae

<400> SEQUENCE: 116

Thr Arg Gly Phe Ser Asp Val Tyr Asp His Ala Phe Asp Pro
1               5                   10

<210> SEQ ID NO 117
<211> LENGTH: 11
<212> TYPE: PRT
<213> ORGANISM: Unknown
<220> FEATURE:
<223> OTHER INFORMATION: Leporidae

<400> SEQUENCE: 117

Gln Ala Ser Gln Ser Ile Gly Asn Ala Leu Ala
1               5                   10

<210> SEQ ID NO 118
<211> LENGTH: 7
<212> TYPE: PRT
<213> ORGANISM: Unknown
<220> FEATURE:
<223> OTHER INFORMATION: Leporidae

<400> SEQUENCE: 118

Ala Gly Ser Asn Leu Ala Ser
1               5
```

```
<210> SEQ ID NO 119
<211> LENGTH: 10
<212> TYPE: PRT
<213> ORGANISM: Unknown
<220> FEATURE:
<223> OTHER INFORMATION: Leporidae

<400> SEQUENCE: 119

Leu Gly Thr Tyr Ser Ala Ile Asp Arg Ala
1               5                   10

<210> SEQ ID NO 120
<211> LENGTH: 10
<212> TYPE: PRT
<213> ORGANISM: Unknown
<220> FEATURE:
<223> OTHER INFORMATION: Leporidae

<400> SEQUENCE: 120

Gly Phe Ser Leu Ser Thr Tyr Ala Met Ile
1               5                   10

<210> SEQ ID NO 121
<211> LENGTH: 12
<212> TYPE: PRT
<213> ORGANISM: Unknown
<220> FEATURE:
<223> OTHER INFORMATION: Leporidae

<400> SEQUENCE: 121

Ile Ile Asn Thr Gly Gly Ser Ala Ser Tyr Ala Ser
1               5                   10

<210> SEQ ID NO 122
<211> LENGTH: 14
<212> TYPE: PRT
<213> ORGANISM: Unknown
<220> FEATURE:
<223> OTHER INFORMATION: Leporidae

<400> SEQUENCE: 122

Thr Arg Gly Val Asn Asp Ala Tyr Glu His Ala Phe Asp Pro
1               5                   10

<210> SEQ ID NO 123
<211> LENGTH: 11
<212> TYPE: PRT
<213> ORGANISM: Unknown
<220> FEATURE:
<223> OTHER INFORMATION: Leporidae

<400> SEQUENCE: 123

Gln Ala Ser Gln Ile Ile Gly Asn Ala Leu Ala
1               5                   10

<210> SEQ ID NO 124
<211> LENGTH: 7
<212> TYPE: PRT
<213> ORGANISM: Unknown
<220> FEATURE:
<223> OTHER INFORMATION: Leporidae

<400> SEQUENCE: 124

Asp Ala Ser Lys Val Pro Ser
1               5
```

```
<210> SEQ ID NO 125
<211> LENGTH: 10
<212> TYPE: PRT
<213> ORGANISM: Unknown
<220> FEATURE:
<223> OTHER INFORMATION: Leporidae

<400> SEQUENCE: 125

Leu Gly Thr Tyr Ser Ser Thr Asp Thr Ala
1               5                   10

<210> SEQ ID NO 126
<211> LENGTH: 10
<212> TYPE: PRT
<213> ORGANISM: Unknown
<220> FEATURE:
<223> OTHER INFORMATION: Leporidae

<400> SEQUENCE: 126

Gly Phe Ser Leu Ser Ser Trp Ala Val Thr
1               5                   10

<210> SEQ ID NO 127
<211> LENGTH: 12
<212> TYPE: PRT
<213> ORGANISM: Unknown
<220> FEATURE:
<223> OTHER INFORMATION: Leporidae

<400> SEQUENCE: 127

Lys Met Thr Ile Tyr Gly Ser Ala Tyr Tyr Ala Ser
1               5                   10

<210> SEQ ID NO 128
<211> LENGTH: 13
<212> TYPE: PRT
<213> ORGANISM: Unknown
<220> FEATURE:
<223> OTHER INFORMATION: Leporidae

<400> SEQUENCE: 128

Asp Tyr Tyr Gly Asn Gly Tyr Ala Ser Arg Leu Asp Pro
1               5                   10

<210> SEQ ID NO 129
<211> LENGTH: 11
<212> TYPE: PRT
<213> ORGANISM: Unknown
<220> FEATURE:
<223> OTHER INFORMATION: Leporidae

<400> SEQUENCE: 129

Gln Ala Ser Gln Ile Ile Gly Asn Ala Leu Ala
1               5                   10

<210> SEQ ID NO 130
<211> LENGTH: 7
<212> TYPE: PRT
<213> ORGANISM: Unknown
<220> FEATURE:
<223> OTHER INFORMATION: Leporidae

<400> SEQUENCE: 130

Asp Ala Ser Lys Val Pro Ser
1               5
```

```
<210> SEQ ID NO 131
<211> LENGTH: 10
<212> TYPE: PRT
<213> ORGANISM: Unknown
<220> FEATURE:
<223> OTHER INFORMATION: Leporidae

<400> SEQUENCE: 131

Leu Gly Thr Tyr Ser Ser Thr Asp Thr Gly
1               5                   10

<210> SEQ ID NO 132
<211> LENGTH: 10
<212> TYPE: PRT
<213> ORGANISM: Unknown
<220> FEATURE:
<223> OTHER INFORMATION: Leporidae

<400> SEQUENCE: 132

Gly Phe Ser Leu Ser Ser Trp Ala Val Thr
1               5                   10

<210> SEQ ID NO 133
<211> LENGTH: 12
<212> TYPE: PRT
<213> ORGANISM: Unknown
<220> FEATURE:
<223> OTHER INFORMATION: Leporidae

<400> SEQUENCE: 133

Lys Met Thr Ile Tyr Gly Ser Pro Tyr Tyr Ala Thr
1               5                   10

<210> SEQ ID NO 134
<211> LENGTH: 13
<212> TYPE: PRT
<213> ORGANISM: Unknown
<220> FEATURE:
<223> OTHER INFORMATION: Leporidae

<400> SEQUENCE: 134

Asp Tyr Tyr Gly Asn Gly Tyr Ala Ser Arg Leu Asp Pro
1               5                   10

<210> SEQ ID NO 135
<211> LENGTH: 11
<212> TYPE: PRT
<213> ORGANISM: Unknown
<220> FEATURE:
<223> OTHER INFORMATION: Leporidae

<400> SEQUENCE: 135

Gln Ala Ser Glu Asp Ile Gly Leu Ala Leu Ala
1               5                   10

<210> SEQ ID NO 136
<211> LENGTH: 7
<212> TYPE: PRT
<213> ORGANISM: Leporidae

<400> SEQUENCE: 136

Gly Ala Ser Tyr Leu Glu Ser
1               5
```

<210> SEQ ID NO 137
<211> LENGTH: 10
<212> TYPE: PRT
<213> ORGANISM: Unknown
<220> FEATURE:
<223> OTHER INFORMATION: Leporidae

<400> SEQUENCE: 137

Leu Gly Gly Phe Pro Leu Ala Ser Trp Ala
1               5                   10

<210> SEQ ID NO 138
<211> LENGTH: 10
<212> TYPE: PRT
<213> ORGANISM: Unknown
<220> FEATURE:
<223> OTHER INFORMATION: Leporidae

<400> SEQUENCE: 138

Gly Phe Ser Leu Ser Ser Tyr Ala Met Thr
1               5                   10

<210> SEQ ID NO 139
<211> LENGTH: 12
<212> TYPE: PRT
<213> ORGANISM: Unknown
<220> FEATURE:
<223> OTHER INFORMATION: Leporidae

<400> SEQUENCE: 139

Ile Ile Asp Ser Tyr Gly Ser Thr Tyr Tyr Ala Ser
1               5                   10

<210> SEQ ID NO 140
<211> LENGTH: 18
<212> TYPE: PRT
<213> ORGANISM: Unknown
<220> FEATURE:
<223> OTHER INFORMATION: Leporidae

<400> SEQUENCE: 140

Asn Ile Gly Ala Asp Tyr Ala Thr Asn Gly His Ala Phe Gly Phe Gly
1               5                   10                  15
His Ile

<210> SEQ ID NO 141
<211> LENGTH: 13
<212> TYPE: PRT
<213> ORGANISM: Unknown
<220> FEATURE:
<223> OTHER INFORMATION: Leporidae

<400> SEQUENCE: 141

Gln Ala Ser Glu Ser Val Phe Ser Gly Asn Arg Leu Ser
1               5                   10

<210> SEQ ID NO 142
<211> LENGTH: 7
<212> TYPE: PRT
<213> ORGANISM: Unknown
<220> FEATURE:
<223> OTHER INFORMATION: Leporidae

<400> SEQUENCE: 142

Ser Ala Ser Thr Leu Ala Ser
1               5

```
<210> SEQ ID NO 143
<211> LENGTH: 10
<212> TYPE: PRT
<213> ORGANISM: Unknown
<220> FEATURE:
<223> OTHER INFORMATION: Leporidae

<400> SEQUENCE: 143

Leu Gly Thr Ile Gly Tyr Thr Asp Thr Ala
1               5                   10

<210> SEQ ID NO 144
<211> LENGTH: 10
<212> TYPE: PRT
<213> ORGANISM: Unknown
<220> FEATURE:
<223> OTHER INFORMATION: Leporidae

<400> SEQUENCE: 144

Gly Phe Ser Leu Ser Arg Tyr Ser Ile Ser
1               5                   10

<210> SEQ ID NO 145
<211> LENGTH: 12
<212> TYPE: PRT
<213> ORGANISM: Unknown
<220> FEATURE:
<223> OTHER INFORMATION: Leporidae

<400> SEQUENCE: 145

Ile Ile Asp Thr Gly Gly Thr Ala Trp Tyr Ala Ser
1               5                   10

<210> SEQ ID NO 146
<211> LENGTH: 9
<212> TYPE: PRT
<213> ORGANISM: Unknown
<220> FEATURE:
<223> OTHER INFORMATION: Leporidae

<400> SEQUENCE: 146

Ile Trp Pro Thr Tyr Asp Thr Gly Ile
1               5

<210> SEQ ID NO 147
<211> LENGTH: 14
<212> TYPE: PRT
<213> ORGANISM: Unknown
<220> FEATURE:
<223> OTHER INFORMATION: Murine

<400> SEQUENCE: 147

Gln Ser Val Leu Tyr Ser Ser Asn Gln Lys Asn Tyr Leu Ala
1               5                   10

<210> SEQ ID NO 148
<211> LENGTH: 7
<212> TYPE: PRT
<213> ORGANISM: Unknown
<220> FEATURE:
<223> OTHER INFORMATION: Murine

<400> SEQUENCE: 148

Trp Ala Ser Thr Arg Glu Ser
1               5
```

-continued

```
<210> SEQ ID NO 149
<211> LENGTH: 10
<212> TYPE: PRT
<213> ORGANISM: Unknown
<220> FEATURE:
<223> OTHER INFORMATION: Murine

<400> SEQUENCE: 149

His Gln Tyr Leu Ser Ser Tyr Met Tyr Thr
1               5                   10

<210> SEQ ID NO 150
<211> LENGTH: 10
<212> TYPE: PRT
<213> ORGANISM: Unknown
<220> FEATURE:
<223> OTHER INFORMATION: Murine

<400> SEQUENCE: 150

Gly Phe Thr Phe Ser Ser Tyr Gly Met Ser
1               5                   10

<210> SEQ ID NO 151
<211> LENGTH: 12
<212> TYPE: PRT
<213> ORGANISM: Unknown
<220> FEATURE:
<223> OTHER INFORMATION: Murine

<400> SEQUENCE: 151

Ile Ser Ser Gly Gly Asn Tyr Ile Tyr Tyr Pro Asp
1               5                   10

<210> SEQ ID NO 152
<211> LENGTH: 12
<212> TYPE: PRT
<213> ORGANISM: Unknown
<220> FEATURE:
<223> OTHER INFORMATION: Murine

<400> SEQUENCE: 152

Gly Ala Tyr Ser Gly Ser Ser Ser Tyr Pro Met Asp
1               5                   10

<210> SEQ ID NO 153
<211> LENGTH: 11
<212> TYPE: PRT
<213> ORGANISM: Unknown
<220> FEATURE:
<223> OTHER INFORMATION: Leporidae

<400> SEQUENCE: 153

Gln Ala Ser Gln Ser Ile Ser Ser Trp Leu Ser
1               5                   10

<210> SEQ ID NO 154
<211> LENGTH: 7
<212> TYPE: PRT
<213> ORGANISM: Unknown
<220> FEATURE:
<223> OTHER INFORMATION: Leporidae

<400> SEQUENCE: 154

Tyr Asp Ala Ser Asn Leu Ala
1               5
```

```
<210> SEQ ID NO 155
<211> LENGTH: 12
<212> TYPE: PRT
<213> ORGANISM: Unknown
<220> FEATURE:
<223> OTHER INFORMATION: Leporidae

<400> SEQUENCE: 155

Leu Gly Gly Tyr Pro Ala Ala Ser Tyr Arg Thr Ala
1               5                   10

<210> SEQ ID NO 156
<211> LENGTH: 7
<212> TYPE: PRT
<213> ORGANISM: Unknown
<220> FEATURE:
<223> OTHER INFORMATION: Leporidae

<400> SEQUENCE: 156

Gly Phe Trp Leu Asn Trp Ala
1               5

<210> SEQ ID NO 157
<211> LENGTH: 13
<212> TYPE: PRT
<213> ORGANISM: Unknown
<220> FEATURE:
<223> OTHER INFORMATION: Leporidae

<400> SEQUENCE: 157

Ile Tyr Arg Gly Ser Gly Ser Glu Trp Tyr Ala Ser Trp
1               5                   10

<210> SEQ ID NO 158
<211> LENGTH: 12
<212> TYPE: PRT
<213> ORGANISM: Unknown
<220> FEATURE:
<223> OTHER INFORMATION: Leporidae

<400> SEQUENCE: 158

Ala Ala Asp Thr Thr Asp Asn Gly Tyr Phe Thr Ile
1               5                   10
```

ANTIBODIES AND METHODS FOR THE DIAGNOSIS AND TREATMENT OF HEPATITIS B VIRUS INFECTION

CROSS-REFERENCE TO RELATED APPLICATIONS

This application is a national stage application under 35 U.S.C. 371 and claims the benefit of PCT Application No. PCT/US2018/042870 having an international filing date of 19 Jul. 2018, which designated the United States, which PCT application claimed the benefit of U.S. provisional patent application Ser. No. 62/534,603, filed Jul. 19, 2017, the entire disclosures of each of which are incorporated herein by reference in their entireties.

REFERENCE TO A SEQUENCE LISTING

This application contains a Sequence Listing submitted electronically as a text file by EFS-Web. A corrected sequence listing was submitted electronically as a text file by EFS-Web on May 5, 2020. The text file, named "6137NIAMS-3-PUS_Corrected_Seq_listing_ST25", has a size in bytes of 32,613 bytes. The information contained in the electronic file is hereby incorporated by reference in its entirety pursuant to 37 C.F.R. § 1.52(e)(5).

FIELD OF THE INVENTION

The present invention is directed to compositions of matter useful for the diagnosis and treatment of Hepatitis B Virus infections in mammals and to methods of using those compositions of matter for the same.

BACKGROUND

Hepatitis B Virus (HBV) is a small partially double-stranded DNA pathogen which poses a health burden on a global scale. Viral hepatitis is the seventh leading cause of death in the world and may be increasing. HBV is non-cytopathic but chronic infection, which affects over 350 million people, and can ultimately lead to liver cirrhosis and hepatocellular carcinoma (HCC). Liver cirrhosis and HCC do not stem from acute infection but from repeated cycles of hepatocyte destruction and regeneration during the immune clearance phase of chronic infection. The first recombinant vaccine was the HBV surface antigen (HBsAg) produced in yeast and has proven highly effective. However, in many parts of the world the vaccine is either not available or it is too expensive. In areas with a large population of HBV carriers, more than 90% of perinatal transmissions result in chronic Hepatitis B virus infection (CHB). The factors which appear to establish CHB are the HBV e-antigen (HBeAg) and subviral particles composed of HBsAg, but the relationship between these antigens and the progression of CHB is complex.

HBV is an enveloped virus with a proteolipid surface glycoprotein (HBsAg) and a core composed of the core antigen (HBcAg) which forms an icosahedral structure containing the viral genome. Both the HBcAg and the closely related HBeAgs are derived from the C gene but initiated from two different start codons. The HBcAg is expressed as a 183-residue protein which polymerizes to form the viral capsid. HBeAg is expressed as a preprotein and, compared to HBcAg, has a 29-residue signal sequence upstream that targets the protein to the endoplasmic reticulum (ER). Following processing of the signal sequence by the ER signal peptidase, oxidation and additional Carboxyl-terminal processing occurs in the ER lumen. The secreted HBeAg retains 10 Amino-terminal residues from the pre-protein but the position of the Carboxyl-terminal processing is unclear, occurring between V149 and R154. While this processing scenario is true for most of HBeAg, about 15% of the protein in the endoplasmic reticulum returns to the cytoplasm. Cytoplasmic forms of HBeAg appear to be able to form DNAdeficient capsids, due to the lack of Carboxyl terminal arginine residues, and can be enveloped and released as decoy particles, thereby playing a role in maintaining viral persistence. Reduction of the soluble oxidized rHBeAg in vitro can cause a conformational switch leading to the assembly of capsid-like structures. The different redox conditions in the ER (oxidizing) and the cytoplasm (reducing) could mediate similar structural changes in vivo.

The HBeAg is not an essential structural component of the virion nor does it appear to take part in the viral replication cycle. Its role appears to be linked to long-term viral persistence in the host, as manifest in chronic HBV infection (typically defined as viral infection persisting six months after initial infection or treatment). Unlike the related HBcAg which activates type 1 T helper (Th1) cells leading to immune attack, the HBeAg activates Th2 cells which promote immune tolerance. HBeAg may cross the placenta and establish immune tolerance in the developing fetus and thereby suppress innate signaling pathways. The molecular details of these complex events are not fully elucidated and better tools are required to assess the specific roles of HBeAg. Identification and structural determinations of the key interactions of HBeAg would provide a clearer path to targeted therapeutics.

In CHB infection, the long-term persistence of HBeAg is associated with the development of HCC. On the other hand, HBeAg seroconversion (from HBeAg carrier to anti-HBeAg carrier) is a marker for the successful therapy of CHB patients. Therefore, the quantitative assay of HBeAg is of clinical importance. All currently available HBeAg assays have two shortcomings: (1) they are non-quantitative in that their readout is a value relative to a defined but arbitrary standard rather than a mass quantity; and (2) neither the antigen nor the antibodies are structurally defined, the latter often also cross-reacting with the HBcAg. This situation persists despite the advances made in defining in structural detail the antigenic determinants of rHBcAg capsids and rHBeAg dimers.

These HBV-associated diseases highlight the need for a better understanding of Hepatitis viruses and their role in mammalian diseases. As part of this understanding, there is a great need for additional diagnostic and therapeutic agents capable of accurately detecting the presence of HBV in a mammal and effectively inhibiting chronic and acute HBV infection and replication. Accordingly, it is an objective of the present invention to specifically identify HBV e-antigen polypeptides and to use that identification specificity to produce compositions of matter useful in the therapeutic treatment and diagnostic detection of HBV in mammals.

SUMMARY

The invention is in part based on a variety of antibodies to Hepatitis B virus (HBV) e-antigen and their use in the detection and diagnosis during active (especially chronic) HBV infection. The inventors have prepared a panel of chimeric Fabs against recombinant HBeAg (rHBeAg). The inventors studied these antibodies in terms of their binding affinity and stoichiometry and crossreactivity with the closely related rHBcAg. From these characterizations, they have developed a sensitive and quantitative assay for the HBeAg and compared its clinical performance with commercial tests. The protein constituents of the assay disclosed herein are of known sequence and structure and can be produced indefinitely by recombinant expression. These features are unique and constitute a powerful incentive for commercial development and application. For further characterization of HBeAg, the inventors immunoaffinity purified the protein from single-patient plasma samples for mass spectrometry. The results surprisingly indicated that the Carboxyl-terminus extends beyond V149, as previously determined, to at least R151.

Thus, this disclosure provides an antibody which binds, preferably specifically, to an HBV e-antigen protein (HBeAg). Optionally, the antibody is a monoclonal antibody, antibody fragment, chimeric antibody, humanized antibody, single-chain antibody, chimerica antibody (such as a chimeric rabbit/human monoclonal antibody, including a chimeric rabbit/human monoclonal antibody fragment "Fab"), or antibody that competitively inhibits the binding of an anti-HBeAg antibody to its respective antigenic epitope. The antibodies of this disclosure may optionally be produced in CHO cells or bacterial cells and preferably inhibit the growth or proliferation of, or induce the death of, a cell to which they bind. For diagnostic purposes, the antibodies of this disclosure may be detectably labeled, attached to a solid support, or the like, such as a lateral flow assay device which provides for point-of-care detection and/or diagnosis of HBV infection.

This disclosure also provides vectors comprising DNA encoding any of the herein described antibodies or antibody fragments. Host cells comprising any such vector are also provided. By way of example, the host cells may be CHO cells, E. coli cells, or yeast cells. A process for producing any of the herein described antibodies is further provided and comprises culturing host cells under conditions suitable for expression of the desired antibody and recovering the desired antibody from the cell culture.

The disclosure also provides a composition of matter comprising an anti-HBeAg antibody as described herein, in combination with a carrier. Optionally, the carrier is a pharmaceutically acceptable carrier.

This disclosure also provides an article of manufacture comprising a container and a composition of matter contained within the container, wherein the composition of matter may comprise an anti-HBeAg antibody as described herein. The article may optionally comprise a label affixed to the container, or a package insert included with the container, that refers to the use of the composition of matter for the therapeutic treatment or diagnostic detection of an HBV infection.

This disclosure also provides the use of an anti-HBeAg polypeptide or antibody as described herein, for the preparation of a medicament useful in the treatment of a condition which is responsive to the anti-HBeAg antibody.

This disclosure also provides any isolated antibody comprising one or more of the complementary determining regions (CDRs), including a CDR-L1, CDR-L2, CDR-L3, CDR-H2, or CDR-H3 sequence disclosed herein, or any antibody that binds to the same epitope as such antibody.

This disclosure also provides a method for inhibiting the growth of a cell that expresses an HBeAg, including contacting the cell with an antibody that binds to the HBeAg, wherein the binding of the antibody to the HBeAg causes inhibition of the growth of the cell expressing the HBeAg. In these methods, the cell may be one or more of a B-lymphocyte and an epithelial cell. Binding of the antibody to the HBeAg causes death of the cell expressing the HBeAg. Optionally, the antibody is a monoclonal antibody, antibody fragment, chimeric antibody, humanized antibody, or single-chain antibody. Antibodies employed in the methods of this disclosure may optionally be conjugated to a growth inhibitory agent or cytotoxic agent such as a toxin. The antibodies employed in the methods of this disclosure may optionally be produced in CHO cells or bacterial cells.

This disclosure also provides a method of therapeutically treating a mammal having an HBV infection by administering to the mammal a therapeutically effective amount of an antibody that binds to the HBeAg, thereby resulting in the effective therapeutic treatment of the infection in the mammal. In these therapeutic methods, the antibody may be a monoclonal antibody, antibody fragment, chimeric antibody, humanized antibody, or single-chain antibody. Antibodies employed in these methods may optionally be conjugated to a growth inhibitory agent or cytotoxic agent such as a toxin. The antibodies employed in these methods of this disclosure may optionally be produced in CHO cells or bacterial cells.

This disclosure also provides a method of determining the presence of an HBeAg in a sample suspected of containing the HBeAg, by exposing the sample to an antibody that binds to the HBeAg and determining binding of the antibody to the HBeAg in the sample, wherein the presence of such binding is indicative of the presence of the HBeAg in the sample. Optionally, the sample may contain cells (which may be fibroblasts, keratinocytes, or dendritic cells) suspected of expressing the HBeAg. The antibody employed in these methods may optionally be detectably labeled, attached to a solid support, or the like.

This disclosure also provides methods of diagnosing the presence of an HBV infection in a mammal, by detecting the level of an HBeAg in a test sample of tissue cells obtained from the mammal, wherein detection of the HBeAg in the test sample is indicative of the presence of HBV infection in the mammal from which the test sample was obtained.

This disclosure also provides methods of diagnosing the presence of an HBV infection in a mammal, by contacting a test sample comprising tissue cells obtained from the mammal with an antibody that binds to an HBeAg and detecting the formation of a complex between the antibody and the HBeAg in the test sample, wherein the formation of a complex is indicative of the presence of an HBV infection in the mammal. Optionally, the antibody employed is detectably labeled, attached to a solid support, or the like. In these methods, the test sample of tissue cells may be obtained from an individual suspected of having a viral infection.

This disclosure also provides a method of treating or preventing or slowing the progression of an HBV infection-related disorder by administering to a subject in need of such treatment an effective amount of an antagonist of an HBeAg. The HBV infection-related disorder may be loss of appetite, joint and muscle pain, low-grade fever, stomach pain, nausea, vomiting, jaundice, cirrhosis, hepatocellular carcinoma (HCC; liver cancer), in particular cirrhosis, or HCC secondary to CHB infection. In these methods, the antagonist of the HBeAg is an anti-HBeAg antibody of this disclosure. Effective treatment or prevention of the disorder may be a result of direct killing or growth inhibition of cells that express an HBeAg or by antagonizing the production of HBeAg.

This disclosure also provides methods of binding an antibody to a cell that expresses an HBeAg, by contacting a cell that expresses an HBeAg with an antibody of this disclosure under conditions which are suitable for binding of the antibody to the HBeAg and allowing binding therebetween. The antibody may be labeled with a molecule or compound that is useful for qualitatively and/or quantitatively determining the location and/or amount of binding of the antibody to the cell.

This disclosure also provides for the use of an HBeAg, a nucleic acid encoding an HBeAg, or a vector or host cell comprising that nucleic acid, or an anti-HBeAg antibody in the preparation of a medicament useful for (i) the therapeutic treatment or diagnostic detection or slowing the progression of an HBV infection, or (ii) the therapeutic treatment, prevention, or slowing the progression of an HBV infection-related disorder.

This disclosure also provides a method for inhibiting the production of additional viral particles in an HBV-infected mammal or cell, wherein the growth of the HBV infected cell is at least in part dependent upon the expression of an HBeAg (wherein the HBeAg may be expressed either within the infected cell itself or a cell that produces polypeptide(s) that have a growth potentiating effect on the infected cells), by contacting the HBeAg with an antibody that binds to the HBeAg, thereby antagonizing the growth-potentiating activity of the HBeAg and, in turn, inhibiting the growth of the infected cell. Preferably the growth of the infected cell is completely inhibited. More preferably, binding of the antibody to the HBeAg induces the death of the infected cell. Optionally, the antibody is a monoclonal antibody, antibody fragment, chimeric antibody, humanized antibody, or single-chain antibody. Antibodies employed in these methods may optionally be conjugated to a growth inhibitory agent or cytotoxic agent such as a toxin, or the like. The antibodies employed in the methods of this disclosure may optionally be produced in CHO cells or bacterial cells.

This disclosure also provides methods of treating a viral infection in a mammal, wherein the infection is at least in part dependent upon the expression of an HBeAg, by administering to the mammal a therapeutically effective amount of an antibody that binds to the HBeAg, thereby antagonizing the activity of the HBeAg and resulting in the effective treatment of the infection in the mammal. Optionally, the antibody is a monoclonal antibody, antibody fragment, chimeric antibody, humanized antibody, or single-chain antibody. Antibodies employed in these methods may optionally be conjugated to a growth inhibitory agent or cytotoxic agent such as a toxin, or the like. The antibodies employed in the methods of this disclosure may optionally be produced in CHO cells or bacterial cells.

Further embodiments will be evident to the skilled artisan upon a reading of the present specification. This disclosure contains the amino acid sequences of Table 1 (referring to the standard single letter amino acid abbreviations).

TABLE 1

"Fab" refers to the clone number of anti-rHBeAg. except rev which is anti-HIV-1 Rev. All clones are rabbit/human chimeric Fabs except me6, which is a murine/human chimeric. LCDR1 and HCDR1, etc refer to V-Light Chain and V-Heavy Chain CDR regions, respectively.

| SEQ ID NO | Description | Sequence |
|---|---|---|
| 1 | HBV c-antigen (HBeAg) | MDIDPYKEFGATV ELLSFLPSDFFPS VRDLLDTAAALYR DALESPEHCSPHH TALRQAILCWGDL MTLATWVGTNLED PASRDLVVSYVNT NVGLKFRQLLWFH ISCLTFGRETVLE YLVSFGVWIRTPP AYRPPNAPILSTL PETTVVRRRGRSP RRRTPSPRRRRSQ SPRRRRSQSRESQ C |
| 2 | HBV e-antigen (HBeAg) | SKLCLGWLWGMDID PYKEFGATVELLSF LPSDFFPSVRDLLD TAAALYRDALESPE HCSPHHTALRQAIL CWGDLMTLATWVGT NLEDPASRDLVVSY VNTNVGLKFRQLLW FHISCLTFGRETVL EYLVSFGVWIRTPP AYRPPNAPILSTLP ETTVVRR |
| 3 | Fab e01 LCDR1 | QASQSISSRLG |
| 4 | Fab e01 LCDR2 | GASTLTS |
| 5 | Fab e01 LCDR3 | LGSDTSDTTA |
| 6 | Fab e01 HCDR1 | GIDLSSNAIS |
| 7 | Fab e01 HCDR2 | IIYGGSIPYYSR |
| 8 | Fab e01 HCDR3 | GKSDGDGYAAYRLDP |
| 9 | Fab e13 LCDR1 | QASQSISSRLG |
| 10 | Fab e13 LCDR3 | LGSDTSTDTA |
| 11 | Fab e13 LCDR2 | GASTLTS |
| 12 | Fab e13 HCDR1 | GIDLSSNAIS |
| 13 | Fab e13 HCDR2 | IIYGGSIPYYSR |
| 14 | Fab e13 HCDR3 | GKSDGDGYAAYRLDP |
| 15 | Fab e25 LCDR1 | QASQSISSRLA |
| 16 | Fab e25 LCDR2 | GASTLAS |
| 17 | Fab e25 LCDR3 | LGSDTSTNTA |
| 18 | Fab e25 HCDR1 | GIDLSSNAIT |
| 19 | Fab e25 HCDR2 | IIYGGSIPYYSR |
| 20 | Fab e25 HCDR3 | GKSDGDGYAAYRLDP |
| 21 | Fab e17 LCDR1 | QASQSVSGRLG |

TABLE 1-continued

"Fab" refers to the clone number of anti-rHBeAg. except rev which is anti-HIV-1 Rev. All clones are rabbit/human chimeric Fabs except me6, which is a murine/human chimeric. LCDR1 and HCDR1, etc refer to V-Light Chain and V-Heavy Chain CDR regions, respectively.

| SEQ ID NO | Description | Sequence |
|---|---|---|
| 22 | Fab e17 LCDR2 | GASTLAS |
| 23 | Fab e17 LCDR3 | LGSDTSTDTA |
| 24 | Fab e17 HCDR1 | GIDLSSNAIS |
| 25 | Fab e17 HCDR2 | IIYGGSIAYYSR |
| 26 | Fab e17 HCDR3 | GKSDGDGYAAYRLDP |
| 27 | Fab e34 LCDR1 | QASQSISSRLG |
| 28 | Fab e34 LCDR2 | GASTLAS |
| 29 | Fab e34 LCDR3 | LGSDTSTDTA |
| 30 | Fab e34 HCDR1 | GIDLSTNAIS |
| 31 | Fab e34 HCDR2 | IIYGGSISYYSS |
| 32 | Fab e34 HCDR3 | GKSDGDGYAAYRLDP |
| 33 | Fab e02 LCDR1 | QASQSISSRLA |
| 34 | Fab e02 LCDR2 | GASTLAS |
| 35 | Fab e02 LCDR3 | LGSDTSDTTA |
| 36 | Fab e02 HCDR1 | GIDLSSNAIS |
| 37 | Fab e02 HCDR2 | IIYGGSIAYYPT |
| 38 | Fab e02 HCDR3 | GKSDGDGYAAYRLDP |
| 39 | Fab e04 LCDR1 | QASQSISSRLA |
| 40 | Fab e04 LCDR2 | GASTLAS |
| 41 | Fab e04 LCDR3 | LGSDTSTNTA |
| 42 | Fab e04 HCDR1 | GIDLNSNAIT |
| 43 | Fab e04 HCDR2 | IIYGGSISYYPS |
| 44 | Fab e04 HCDR3 | GKSDGDGYAAYRLDP |
| 45 | Fab e09 LCDR1 | QASQSISRRLA |
| 46 | Fab e09 LCDR2 | GASTLAS |
| 47 | Fab e09 LCDR3 | LGSDTSTNTA |
| 48 | Fab e09 HCDR1 | GIDLNSNAIT |
| 49 | Fab e09 HCDR2 | IIYGGSISYYPS |
| 50 | Fab e09 HCDR3 | GKSDGDGYAAYRLDP |
| 51 | Fab e06 LCDR1 | QASQSISNRLA |
| 52 | Fab e06 LCDR2 | GASTLAS |
| 53 | Fab e06 LCDR3 | LGSDTSTNTA |
| 54 | Fab e06 HCDR1 | GIDLSSYAMA |
| 55 | Fab e06 HCDR2 | IIYGGSIPYYAN |
| 56 | Fab e06 HCDR3 | GTSDGEGYAAYRLDP |
| 57 | Fab e14 LCDR1 | QASEDISSRLA |
| 58 | Fab e14 LCDR2 | GASTLAS |
| 59 | Fab e14 LCDR3 | LGSYSSSDTA |
| 60 | Fab e14 HCDR1 | GIDLSSNAIS |
| 61 | Fab e14 HCDR2 | IIYGGSIPYYSR |
| 62 | Fab e14 HCDR3 | GKSDGDGYAAYRLDP |
| 63 | Fab e16 LCDR1 | QASESVANNNRLS |
| 64 | Fab e16 LCDR2 | GASTLAS |
| 65 | Fab e16 LCDR3 | LGSASSTDTA |
| 66 | Fab e16 HCDR1 | GIDLSSNAIS |
| 67 | Fab e16 HCDR2 | IIYGGSIPYYSR |
| 68 | Fab e16 HCDR3 | GKSDGDGYAAYRLDP |
| 69 | Fab e10 LCDR1 | QASQSIGSRLG |
| 70 | Fab e10 LCDR2 | GASTLAS |
| 71 | Fab e10 LCDR3 | LGSDTSSATA |
| 72 | Fab e10 HCDR1 | GIDLVTYAMA |
| 73 | Fab e10 HCDR2 | IIYGGGLSYYPS |
| 74 | Fab e10 HCDR3 | GSSDGDGYAAYRLDP |
| 75 | Fab e03 LCDR1 | QARQSIGSRLG |
| 76 | Fab e03 LCDR2 | GASTLAS |
| 77 | Fab e03 LCDR3 | LGSDTSSNTA |
| 78 | Fab e03 HCDR1 | GIDLVTSAMA |
| 79 | Fab e03 HCDR2 | IIYGGGLSYYPS |
| 80 | Fab e03 HCDR3 | GSSDGDGYAAYRLDP |
| 81 | Fab e12 LCDR1 | QARQSIGSRLG |
| 82 | Fab e12 LCDR2 | GASTLAS |
| 83 | Fab e12 LCDR3 | LGSDTSSNTA |
| 84 | Fab e12 HCDR1 | GIDLVTSAMA |

TABLE 1-continued

"Fab" refers to the clone number of anti-rHBeAg. except rev which is anti-HIV-1 Rev. All clones are rabbit/human chimeric Fabs except me6, which is a murine/human chimeric. LCDR1 and HCDR1, etc refer to V-Light Chain and V-Heavy Chain CDR regions, respectively.

| SEQ ID NO | Description | Sequence |
|---|---|---|
| 85 | Fab e12 HCDR2 | IIGGGGLSYYPS |
| 86 | Fab e12 HCDR3 | GSSDGDGYAAYRLDP |
| 87 | Fab e24 LCDR1 | QASQSIGSRLG |
| 88 | Fab e24 LCDR2 | GASTLAS |
| 89 | Fab e24 LCDR3 | LGSDTSSATA |
| 90 | Fab e24 HCDR1 | GIDLSSNAVS |
| 91 | Fab e24 HCDR2 | IIYGGGITYYAS |
| 92 | Fab e24 HCDR3 | GSSDGDGYAAYRLDP |
| 93 | Fab e05 LCDR1 | QASEDISSRLA |
| 94 | Fab e05 LCDR2 | SASTLAS |
| 95 | Fab e05 LCDR3 | LGSLSSSDTA |
| 96 | Fab e05 HCDR1 | GIDLVTSAMA |
| 97 | Fab e05 HCDR2 | IIYGGGLSYYPS |
| 98 | Fab e05 HCDR3 | GSSDGDGYAAYRLDP |
| 99 | Fab e30 LCDR1 | QASQSIGDKLA |
| 100 | Fab e30 LCDR2 | SASVLAS |
| 101 | Fab e30 LCDR3 | LGSHTASDIA |
| 102 | Fab e30 HCDR1 | GIDLTNYAMG |
| 103 | Fab e30 HCDR2 | IINMGEFTSYAT |
| 104 | Fab e30 HCDR3 | GNGGNYPFYAIDI |
| 105 | Fab e29 LCDR1 | QASQSVSAYLS |
| 106 | Fab e29 LCDR2 | RASTLAS |
| 107 | Fab e29 LCDR3 | LGTYSSSNTA |
| 108 | Fab e29 HCDR1 | GFSLSTHAIS |
| 109 | Fab e29 HCDR2 | IIFAASSTYYAS |
| 110 | Fab e29 HCDR3 | TSISSDGFPDNFNI |
| 111 | Fab e28 LCDR1 | QASQSIDGALS |
| 112 | Fab e28 LCDR2 | VASSLAS |
| 113 | Fab e28 LCDR3 | LGTYNAFDRA |
| 114 | Fab e28 HCDR1 | GFSLSNYAMI |
| 115 | Fab e28 HCDR2 | IIGSGGSPYYAS |
| 116 | Fab e28 HCDR3 | TRGFSDVYDHAFDP |
| 117 | Fab e21 LCDR1 | QASQSIGNALA |
| 118 | Fab e21 LCDR2 | AGSNLAS |
| 119 | Fab e21 LCDR3 | LGTYSAIDRA |
| 120 | Fab e21 HCDR1 | GFSLSTYAMI |
| 121 | Fab e21 HCDR2 | IINTGGSASYAS |
| 122 | Fab e21 HCDR3 | TRGVNDAYEHAFDP |
| 123 | Fab e32 LCDR1 | QASQIIGNALA |
| 124 | Fab e32 LCDR2 | DASKVPS |
| 125 | Fab e32 LCDR3 | LGTYSSTDTA |
| 126 | Fab e32 HCDR1 | GFSLSSWAVT |
| 127 | Fab e32 HCDR2 | KMTIYGSAYYAS |
| 128 | Fab e32 HCDR3 | DYYGNGYASRLDP |
| 129 | Fab e38 LCDR1 | QASQIIGNALA |
| 130 | Fab e38 LCDR2 | DASKVPS |
| 131 | Fab e38 LCDR3 | LGTYSSTDTG |
| 132 | Fab e38 HCDR1 | GFSLSSWAVT |
| 133 | Fab e38 HCDR2 | KMTIYGSPYYAT |
| 134 | Fab e38 HCDR3 | DYYGNGYASRLDP |
| 135 | Fab e08 LCDR1 | QASEDIGLALA |
| 136 | Fab e08 LCDR2 | GASYLES |
| 137 | Fab e08 LCDR3 | LGGFPLASWA |
| 138 | Fab e08 HCDR1 | GFSLSSYAMT |
| 139 | Fab e08 HCDR2 | IIDSYGSTYYAS |
| 140 | Fab e08 HCDR3 | NIGADYATNGHAFGFGHI |
| 141 | Fab e15 LCDR1 | QASESVFSGNRLS |
| 142 | Fab e15 LCDR2 | SASTLAS |
| 143 | Fab e15 LCDR3 | LGTIGYTDTA |
| 144 | Fab e15 HCDR1 | GFSLSRYSIS |
| 145 | Fab e15 HCDR2 | IIDTGGTAWYAS |
| 146 | Fab e15 HCDR3 | IWPTYDTGI |
| 147 | Fab me6 LCDR1 | QSVLYSSNQKNYLA |
| 148 | Fab me6 LCDR2 | WASTRES |

TABLE 1-continued

"Fab" refers to the clone number of anti-rHBeAg. except rev which is anti-HIV-1 Rev. All clones are rabbit/human chimeric Fabs except me6, which is a murine/human chimeric. LCDR1 and HCDR1, etc refer to V-Light Chain and V-Heavy Chain CDR regions, respectively.

| SEQ ID NO | Description | Sequence |
|---|---|---|
| 149 | Fab me6 LCDR3 | HQYLSSYMYT |
| 150 | Fab me6 HCDR1 | GFTFSSYGMS |
| 151 | Fab me6 HCDR2 | ISSGGNYIYYPD |
| 152 | Fab me6 HCDR3 | GAYSGSSSYPMD |
| 153 | Fab rev LCDR1 | QASQSISSWLS |
| 154 | Fab rev LCDR2 | YDASNLA |
| 155 | Fab rev LCDR3 | LGGYPAASYRTA |
| 156 | Fab rev HCDR1 | GFWLNWA |
| 157 | Fab rev HCDR2 | IYRGSGSEWYASW |
| 158 | Fab rev HCDR3 | AADTTDNGYFTI |

BRIEF DESCRIPTION OF THE FIGURES

FIGS. 1A-1C show the amino acid sequences of (FIG. 1A; SEQ ID NO:1) HBcAg (amino acids 1-183) and (FIG. 1B; SEQ ID NO:2) rHBeAg [amino acids (−10)-149]. The amino acid sequences of the HBcAg and rHBeAgs with the genotype D subtype adw. The amino-terminal residues "(R)(R)" in FIG. 1B are variable in the HBeAg. FIG. 1C shows the sequence schematics for HBcAg and HBeAg. In addition to the assembly domain (residues 1-149), HBcAg has an arginine-rich nucleic acid-binding domain (residues 150-183). HBeAg shares the assembly domain with HBcAg but has a 10-residue propeptide (−10 to −1) and a potentially variable Carboxyl-terminus.

FIG. 5A shows Biacore sensograms indicating binding kinetics generated from immobilized Fab e13 (ligand) titrated with analyte mixtures containing a fixed amount of rHBeAg (1.5 µM) and a variable amount of Fab me6 (0-133 nM). FIG. 5B shows immobilized Fab me6 (ligand) titrated with analyte mixtures containing either a fixed amount (0.4 µM) of rHBeAg and a variable amount of Fab e13, or a fixed amount (1.5 µM) rHBeAg and a variable amount of Fab me6. The steady-state maximum binding is plotted as a function of analyte Fab concentration (abscissa). For both FIGS. 5A and 5B, the ordinate scales indicate SPR response in resonance units (RU).

FIG. 6D shows the HBV-negative patient plasma samples were used in the ELISA to determine cut-off values (CO). Negative-control average OD 450 nm was <0.07 with STD=0.0036. FIG. 6E shows the intra-plate coefficient of variability (CV) indicates variability of data independent of absolute values and the inter-plate CV, the variation from repeated experiments (precision). Generally acceptable values for intra- and inter-assay CV are <10 and <15, respectively. FIG. 6F shows the matrix effect checks non-specific interaction of plasma components. The titration plots indicate no significant interactions occur.

FIG. 6G is a calibration curve for rHBeAg over the range 0-0.5 µg/ml (28 nM). FIGS. 6H and 6I are calibration curves for WHO reference standard over the ranges 0-1.0 and 0-10 PE IU/ml, respectively. The lowest detection limit for rHBeAg is 4 ng/ml. From the plots: 1 PE IU/ml approx. 0.2 µg/ml (10 nM) rHBeAg. Each experiment (FIGS. 6G-6I) was performed in triplicate and the average values plotted. The linear fits are shown on the right in each FIG.

FIG. 9A is a SDSPAGE/Western blot of rHBeAg run under reducing (R) conditions (+DTT) and non-reducing conditions (O). The position of the reduced monomer is indicated with M, and the oxidized monomer with the higher mobility with M*. HBeAg was immunoaffinity purified from an individual HBV positive patient and analyzed under reducing (+R) and non-reducing conditions (+O). An HBV-negative plasma sample was analyzed under reducing conditions (−R). FIG. 9B shows SDS-PAGE with Coomassie Blue staining: rHBeAg analyzed under reducing (lane 1) and non-reducing conditions (lane 2); rHBcAg analyzed under reducing (lane 3) and non-reducing conditions (lane 4). Due to the intra-molecular disulfide bond (Cys(−7)-Cys61) in rHBeAg, the protein in lane 2 has a slightly higher mobility than the reduced form, whereas, due to the inter-molecular disulfide bond (Cys61-Cys61) in rHBcAg, the protein in lane 4 has a substantially lower mobility than the reduced from. The molecular weights of a standard protein mixture are indicated.

DETAILED DESCRIPTION

I. Definitions

Figure 2:
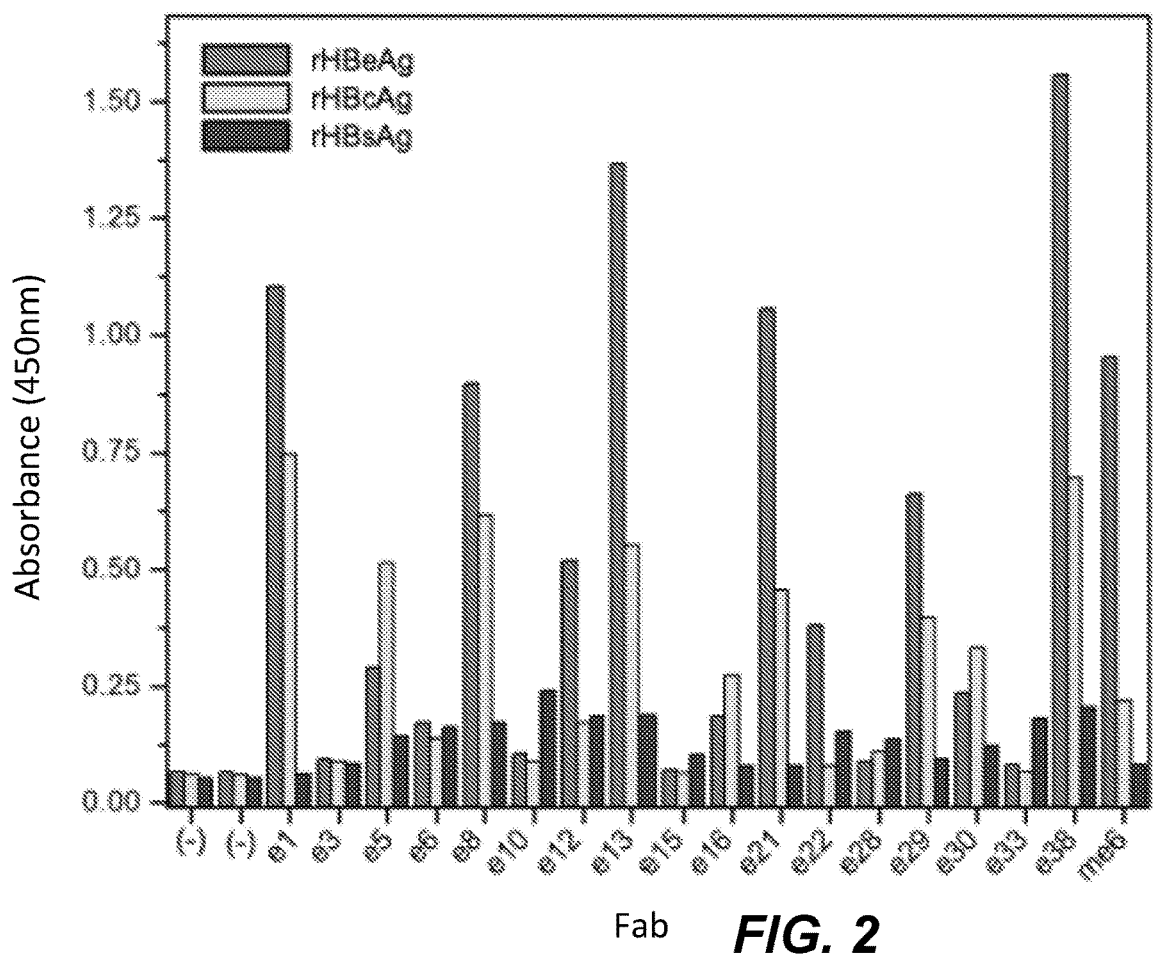
FIG. 2 shows the results of screening the affinity and specificity of Fabs. Microtitre plates were coated with 10 µg/ml of dimeric rHBeAg, HBcAg capsid or rHBsAg, washed, blocked, and then treated with 2 µg/ml of the indicated Fab. Following additional washing, bound Fab was detected with antihuman IgG. The samples indicated with (−) were probed with two different HBV-negative human plasmas. This survey was performed twice, with similar results.

The terms "HBeAg" and "HBV e-antigen" as used herein, refer to various Hepatitis B Virus polypeptides. The HBeAgs described herein may be isolated from a variety of sources, such as from human tissue types or from another source, or prepared by recombinant or synthetic methods. The term "HBeAg" refers to each individual HBV e-polypeptide disclosed herein. All disclosures in this specification which refer to the "HBeAg" refer to each of the polypeptides individually as well as jointly. For example, descriptions of the preparation of, purification of, derivation of, formation of antibodies to or against, formation of HBeAg binding oligopeptides to or against, administration of, compositions containing, treatment of a disease with, etc., pertain to each polypeptide of the disclosure individually. The term "HBeAg" also includes variants and recombinant forms of the HBV e-antigens disclosed herein.

In the Hepatitis B virus literature, there are different terms for each of the HBV proteins, and these can also have different meanings, causing considerable ambiguity and potential for confusion: the terms HBcAg, HBc and core antigen may refer to a protein (either natural or recombinant), an antigen, or the viral nucleocapsid; the terms HBeAg, HBe and e-antigen may refer to a protein, an antigen, or a disease state. In addition, there are ambiguities of sequence (subtype, laboratory mutation, and both the Amino- and Carboxyl-termini), oxidation state, and assembly state (monomer, dimer, and capsid). To avoid such ambiguities, in this disclosure these proteins are referred to by the following terms: The assembly state of HBcAg (either dimer or capsid) will be stated where necessary. The sequences for HBcAg and HBeAg are provided in FIGS. 1A and 1B, respectively. HBcAg (HBV core antigen, the viral nucleocapsid); HBeAg (HBV e-antigen, a soluble protein produced during infection, largely collinear with HBcAg); HBsAg (HBV surface antigen, a component of the virion envelope); rHBcAg (recombinant HBV core antigen, a dimeric protein corresponding to core antigen residues 1-149 and having an intermolecular disulfide bond; rHBeAg (recombinant HBV e-antigen, a dimeric protein corresponding to core antigen residues 1-149, but preceded by a 10-residue propeptide and having an intramolecular C(−7)-C61 disulfide bond; rHBsAg (recombinant HBV surface antigen, corresponding to the Small form of HBsAg, genotype D).

A "native sequence HBeAg" comprises a polypeptide having the same amino acid sequence as the corresponding HBeAg derived from nature. Such native sequence HBeAgs can be isolated from nature or can be produced by recombinant or synthetic means. The term "native sequence HBeAg" specifically encompasses naturally-occurring truncated or secreted forms of the specific HBeAg (e.g., an extracellular domain sequence), naturally-occurring variant forms (e.g., alternatively spliced forms) and naturally-occurring allelic variants of the polypeptide. The native sequence HBeAgs disclosed herein may be mature or full-length native sequence polypeptides comprising the full-length amino acids sequences.

"HBeAg variant" means an HBeAg, preferably an active HBeAg, as defined herein having at least about 80% amino acid sequence identity with a full-length native HBeAg sequence as disclosed herein, an extracellular domain of an HBeAg, as disclosed herein or any other fragment of a full-length HBeAg sequence as disclosed herein (such as those encoded by a nucleic acid that represents only a portion of the complete coding sequence for a full-length HBeAg). Such HBeAg variants include, for instance, HBeAgs wherein one or more amino acid residues are added or deleted, at the N- or C-terminus of the full-length native amino acid sequence. Ordinarily, an HBeAg variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence HBeAg sequence as disclosed herein, or any other specifically defined fragment of a full-length HBeAg sequence as disclosed herein. Optionally, HBeAg variant polypeptides will have no more than one conservative amino acid substitution as compared to the native HBeAg sequence, alternatively no more than 2, 3, 4, 5, 6, 7, 8, 9, or 10 conservative amino acid substitution as compared to the native HBeAg sequence.

"Percent (%) amino acid sequence identity" with respect to amino acid sequences, such as the HBeAg sequences identified herein, is defined as the percentage of amino acid residues in a candidate sequence that are identical to the amino acid residues in the specific HBeAg sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, % amino acid sequence identity values may be generated using the sequence comparison computer program ALIGN-2, wherein the complete source code for the ALIGN-2 program is provided in U.S. Pat. No. 7,160,985, which is incorporated herein by reference. The ALIGN-2 sequence comparison computer program was authored by Genentech, Inc. and the source code thereof has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California or may be compiled from the source code. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as 100 times the fraction X/Y, where X is the number of amino acid residues scored as identical matches by the sequence alignment program ALIGN-2 in that program's alignment of A and B, and where Y is the total number of amino acid residues in B. Where the length of amino acid sequence A is not equal to the length of amino acid sequence B, the % amino acid sequence identity of A to B will not equal % amino acid sequence identity of B to A.

"HBeAg variant polynucleotide" or "HBeAg variant nucleic acid sequence" means a nucleic acid molecule which encodes an HBeAg, preferably an active HBeAg, as defined herein and which has at least about 80% nucleic acid sequence identity with a nucleic acid sequence encoding a full-length native sequence HBeAg sequence as disclosed herein, a specific domain of an HBeAg, as disclosed herein or any other fragment of a full-length HBeAg sequence as disclosed herein (such as those encoded by a nucleic acid that represents only a portion of the complete coding sequence for a full-length HBeAg). Ordinarily, a HBeAg variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence HBeAg sequence, an extracellular domain of an HBeAg or any other fragment of a full-length HBeAg sequence. Variants do not encompass the native nucleotide sequence.

Ordinarily, HBeAg variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 nucleotides in length, wherein in this context the term "about" means the referenced nucleotide sequence length plus or minus 10% of that referenced length.

"Isolated," when used to describe the various HBeAgs disclosed herein, means a polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. The polypeptide may be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or silver stain. Isolated polypeptide includes polypeptide in situ within recombinant cells, since at least one component of the HBeAg natural environment will not be present. Ordinarily, isolated polypeptide will be prepared by at least one purification step.

An "isolated" HBeAg-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers (1995).

"Stringent conditions" or "high stringency conditions" as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/ sodium citrate) followed by a 10 minute high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" used herein refers to a chimeric polypeptide comprising an HBeAg or anti-HBeAg antibody fused to a "tag polypeptide." The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of an HBeAg which retain a biological and/or an immunological activity of native or naturally-occurring HBeAg, wherein "biological" activity refers to a biological function (either inhibitory or stimulatory) caused by a native or naturally-occurring HBeAg other than the ability to induce the production of an antibody against an antigenic epitope possessed by a native or naturally-occurring HBeAg and an "immunological" activity refers to the ability to induce the production of an antibody against an antigenic epitope possessed by a native or naturally-occurring HBeAg.

The term "antagonist" is used in the broadest sense, and includes any molecule that partially or fully blocks, inhibits, or neutralizes a biological activity of a native HBeAg disclosed herein. In a similar manner, the term "agonist" is used in the broadest sense and includes any molecule that mimics a biological activity of a native HBeAg disclosed herein. Suitable agonist or antagonist molecules specifically include agonist or antagonist antibodies or antibody fragments, fragments or amino acid sequence variants of native HBeAgs, peptides, antisense oligonucleotides, small organic molecules, etc. Methods for identifying agonists or antagonists of an HBeAg may comprise contacting an HBeAg with a candidate agonist or antagonist molecule and measuring a detectable change in one or more biological activities normally associated with the HBeAg.

"Treating" or "treatment" or "alleviation" refers to both therapeutic treatment and prophylactic or preventative measures, wherein the object is to prevent or slow the progression (lessen) the targeted pathologic condition or disorder. Those in need of treatment include those already with the disorder as well as those prone to have the disorder or those in whom the disorder is to be prevented. A subject or mammal is successfully "treated" for an HBeAg-expressing viral infection if, after receiving a therapeutic amount of an anti-HBeAg antibody or HBeAg binding oligopeptide according to the methods of this disclosure, the patient shows observable and/or measurable reduction in or absence of one or more of the following: reduction in the number of infected cells or absence of the infected cells; reduction in the number of infected cells; inhibition (i.e., slow to some extent and preferably stop) of HBV infection including the spread of infection into tissues; inhibition (i.e., slow to some extent and preferably stop) of infection spread; inhibition, to some extent, and/or relief to some extent, of one or more of the symptoms associated with the HBV infection, including chronic HBV infection, such as cirrhosis and HCC; reduced morbidity and mortality, and improvement in quality of life issues. To the extent the anti-HBeAg antibody or HBeAg binding oligopeptide may prevent growth or infection and/or kill existing infected cells, it may be cytostatic and/or cytotoxic. Reduction of these signs or symptoms may also be felt by the patient. The above parameters for assessing successful treatment and improvement in the HBV-associated diseases and disorders are readily measurable by procedures familiar to a medical provider.

"Chronic" administration refers to administration of the agent(s) in a continuous mode as opposed to an acute mode, to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of or diagnosis of a viral infection refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody or HBeAg binding oligopeptide of this disclosure can adhere or attach. Examples of solid phases encompassed herein include those formed partially or entirely of glass (e.g., controlled pore glass), polysaccharides (e.g., agarose), polyacrylamides, polystyrene, polyvinyl alcohol, and silicones. Depending on the context, the solid phase can comprise the well of an assay plate or a lateral flow assay device; in others, it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as an HBeAg, an antibody thereto or a HBeAg binding oligopeptide) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of a polypeptide, antibody or HBeAg binding oligopeptide, or an agonist or antagonist thereof as disclosed herein is an amount sufficient to carry out a specifically stated purpose. An "effective amount" may be determined empirically in relation to the stated purpose.

The term "therapeutically effective amount" refers to an amount of an antibody, polypeptide, or HBeAg binding oligopeptide, or other drug effective to "treat" a disease or disorder in a subject or mammal. In the case of an HBV infection, the therapeutically effective amount of the drug may reduce the number of infected cells; inhibit (i.e., slow to some extent and preferably stop) spread of the infection into other cells, and/or relieve to some extent one or more of the symptoms associated with the infection, including CHB infection. See the definition herein of "treating." To the extent the drug may prevent growth and/or kill existing infected cells, it may be cytostatic, cytotoxic, anti-inflammatory, immunomodulatory, and/or immunosuppressing.

A "growth inhibitory amount" of an anti-HBeAg antibody or HBeAg binding oligopeptide is an amount capable of inhibiting the growth of a cell, especially virus infected cell, either in vitro or in vivo. A "growth inhibitory amount" of an anti-HBeAg antibody or HBeAg binding oligopeptide for purposes of inhibiting infected cell growth may be determined empirically.

A "cytotoxic amount" of an anti-HBeAg antibody or HBeAg binding is an amount capable of causing the destruction of a cell, especially virus infected cell, either in vitro or in vivo. A "cytotoxic amount" of an anti-HBeAg antibody or HBeAg binding oligopeptide for purposes of inhibiting cell growth may be determined empirically.

The term "antibody" is used in the broadest sense and specifically covers, for example, single anti-HBeAg monoclonal antibodies (including agonist, antagonist, and neutralizing antibodies), anti-HBeAg antibody compositions with polyepitopic specificity, polyclonal antibodies, chimeric antibodies, single chain anti-HBeAg antibodies, and fragments of anti-HBeAg antibodies (see below) as long as they exhibit the desired biological or immunological activity or specificity. The term "immunoglobulin" (Ig) is used interchangeably with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The antibody may be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells because at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, CT, 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses based on relatively minor differences in CH sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of an antibody for its antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 3-30, or more typically, 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, MD (1991)). The constant domains are not involved directly in binding an antibody to an antigen, but exhibit various effector functions, such as participation of the antibody in antibody dependent cellular cytotoxicity (ADCC).

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, useful monoclonal antibodies of this disclosure may be prepared by the hybridoma methodology first described by Kohler et al., Nature, 256: 495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with, or homologous to, corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape, etc.), and human constant region sequences.

Chimeric rabbit/human Fabs consist of rabbit variable domains $V_H$ and $V_K$ and human constant domains $C_H1$ and $C_L$ (Rader, C., et al., (2000) *The rabbit antibody repertoire as a novel source for the generation of therapeutic human antibodies.* J Biol Chem 275:13668-676; Rader, C. (2009) *Generation and selection of rabbit antibody libraries by phage display.* Methods Mol Biol 525:101-28, xiv). It has been shown that libraries of such chimeric hybrid antibodies can be generated from the spleen and bone marrow of immunized rabbits and subsequently selected by phage display (Popkov, M., et al., (2004) *Human/mouse cross-reactive anti-VEGF receptor 2 recombinant antibodies selected from an immune b9 allotype rabbit antibody library.* J Immunol Methods 288:149-64). These Fabs can be conveniently expressed in *E. coli* using an expression cassette with two signal sequences, pelB and ompA, which direct secretion of the two chains into the oxidizing periplasmic space. A Carboxyl-terminal His-tag on the $V_H$-$C_H1$ chain allows purification of the soluble protein. Such chimeric antibodies often have both high affinity and specificity and can be fully humanized, making them both powerful research tools and of therapeutic potential.

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide-linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) can recognize and bind antigen, although at a lower affinity than the entire binding site.

"Single-chain Fv" (also abbreviated as "sFv" or "scFv") are antibody fragments that comprise the VH and VL antibody domains connected into a single polypeptide chain.

Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all at least one, and typically two, variable domains, in which all or substantially all the hypervariable loops correspond to those of a non-human immunoglobulin and all or substantially all the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-25 (1986); Riechmann et al., Nature 332:323-329 (1988); and Presta, Curr. Op. Struct. Biol. 2:593-96 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "binds specifically" to a human antigen (i.e., has a binding affinity (Kd) value of no more than about $1\times10^{-7}$ M, preferably no more than about $1\times10^{-8}$ and most preferably no more than about $1\times10^{-9}$ M) but has a binding affinity for a homologue of the antigen from a second non-human mammalian species which is at least about 50-fold, or at least about 500-fold, or at least about 1000-fold, weaker than its binding affinity for the human antigen. The species-dependent antibody can be of any of the various types of antibodies as defined above, but preferably is a humanized or human antibody.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, MD (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same," as used herein, denotes a sufficiently high degree of similarity between two numeric values (generally one associated with an antibody of the disclosure and the other associated with a reference/comparator antibody) such that one of skill in the art would consider the difference between the two values to be of little or no biological and/or statistical significance within the context of the biological characteristic measured by the values (e.g., Kd values). The difference between the two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of this disclosure. Illustrative embodiments are described in the following.

The "Kd" or "Kd value" according to this disclosure is measured by a radiolabeled antigen binding assay (MA) performed with the Fab version of an antibody of interest and its antigen as described by the following assay that measures solution binding affinity of Fabs for antigen by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) are coated overnight with 5 mcg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate, 100 pM or 26 pM [125I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to ensure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 microliter/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. The Kd or Kd value may also be measured by using surface plasmon resonance assays using a BIAcore™-2000 or a BIAcore™-3000 (BIAcore, Inc., Piscataway, NJ) at 25° C. with immobilized antigen CM5 chips at approx. 10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, into 5 mcg/ml (approx. 0.2 uM) before injection at a flow rate of 5 microliter/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 microliter/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol Biol 293:865-881. If the on-rate exceeds $10^6$ M-1 S-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrometer (Aviv Instruments) or a 8000-series SLM-Aminco spectrophotometer (ThermoSpectronic) with a stir red cuvette.

An "on-rate" or "rate of association" or "association rate" or "kon" according to this disclosure can also be determined with the same surface plasmon resonance technique described above using a BIAcore™-2000 or a BIAcore™-3000 (BIAcore, Inc., Piscataway, NJ) at 25° C. with immobilized antigen CM5 chips at approx. 10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 mcg/ml (approx. 0.2 uM) before injection at a flow rate of 5 microliter/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 microliter/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) was calculated as the ratio koff/kon. See, e.g., Chen, Y., et al., (1999) J. Mol Biol 293:865-81. However, if the on-rate exceeds $10^6$ M-1 S-1 by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The phrase "substantially reduced," or "substantially different", as used herein, denotes a sufficiently high degree of difference between two numeric values (generally one associated with an antibody of the disclosure and the other associated with a reference/comparator antibody) such that one of skill in the art would consider the difference between the two values to be of statistical significance within the context of the biological characteristic measured by the values (e.g., Kd values, HAMA response). The difference between the two values is preferably greater than about 10%, preferably greater than about 20%, preferably greater than about 30%, preferably greater than about 40%, preferably greater than about 50% of the value for the reference/comparator antibody.

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is an HBeAg polypeptide.

An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two, or one of positions 71H, 73H and 78H; for instance, the amino acid residues at those positions may be 71A, 73T and/or 78A. The VL acceptor human framework may be identical in sequence to the VL human immunoglobulin framework sequence or human consensus framework sequence.

Antibodies of this disclosure may compete for binding to the same epitope as is bound by a second antibody. Monoclonal antibodies are considered to share the "same epitope" if each blocks binding of the other by 40% or greater at the same antibody concentration in a standard in vitro antibody competition binding analysis.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., supra. For the VL, the subgroup may be subgroup kappa I as in Kabat et al. For the VH, the subgroup is subgroup III as in Kabat.

A "VH subgroup III consensus framework" comprises the consensus sequence obtained from the amino acid sequences in variable heavy subgroup III of Kabat et al.

A "VL subgroup I consensus framework" comprises the consensus sequence obtained from the amino acid sequences in variable light kappa subgroup I of Kabat et al.

An "unmodified human framework" is a human framework which has the same amino acid sequence as the acceptor human framework, e.g. lacking human to non-human amino acid substitution(s) in the acceptor human framework.

An "altered hypervariable region" for the purposes herein is a hypervariable region comprising one or more (e.g. one to about 16) amino acid substitution(s) therein.

An "un-modified hypervariable region" for the purposes herein is a hypervariable region having the same amino acid sequence as a non-human antibody from which it was derived, i.e. one which lacks one or more amino acid substitutions therein.

The term "hypervariable region", "HVR", "HV" or "CDR", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). Several hypervariable region delineations are in use and are encompassed herein. The Kabat Complementarity Determining Regions (CDRs) are based on sequence variability and are the most commonly used. The "contact" hypervariable regions are based on an analysis of the available complex crystal structures. The residues from each of these hypervariable regions are noted below. Unless otherwise denoted, Kabat numbering is employed. Hypervariable region locations are generally: amino acids 24-34 (HVR-L1), amino acids 49-56 (HVR-L2), amino acids 89-97 (HVR-L3), amino acids 26-35A (HVR-H1), amino acids 49-65 (HVR-H2), and amino acids 93-102 (HVR-H3). Hypervariable regions may also comprise "extended hypervariable regions" as follows: amino acids 24-36 (L1), and amino acids 46-56 (L2) in the VL, numbered according to Kabat et al., supra for each of these definitions.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity or binding specificity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-55 (1995); Yelton et al. J. Immunol. 155:1994-2004 (1995); Jackson et al., J. Immunol. 154(7):3310-19 (1995); and Hawkins et al, J. Mol. Biol. 226:889-96 (1992).

A "blocking" antibody or an "antagonist" antibody is one which inhibits or reduces biological activity of the antigen it binds. Preferred blocking antibodies or antagonist antibodies substantially or completely inhibit the biological activity of the antigen.

A "HBeAg binding oligopeptide" is an oligopeptide that binds, preferably specifically, to an HBeAg. HBeAg binding oligopeptides may be chemically synthesized using known oligopeptide synthesis methodology or may be prepared and purified using recombinant technology. HBeAg binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides are capable of binding, preferably specifically, to an HBeAg. HBeAg binding oligopeptides of this disclosure preferably comprise or consist of at least one complementarity determining region (CDR) of the antibodies of this disclosure. HBeAg binding oligopeptides may be identified without undue experimentation using well known techniques. In this regard, techniques for screening oligopeptide libraries for oligopeptides that are capable of specifically binding to a polypeptide target are known in the art (see, e.g., U.S. Pat. Nos. 5,556,762, 5,750,373, 4,708, 871, 4,833,092, 5,223,409, 5,403,484, 5,571,689, 5,663, 143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-16 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, Smith, G. P. (1991) Current Opin. Biotechnol., 2:668).

An antibody, oligopeptide or other organic molecule "which binds" an antigen of interest, e.g. an HBV polypeptide antigen target, is one that binds the antigen with sufficient affinity such that the antibody or oligopeptide is useful as a diagnostic and/or therapeutic agent in targeting a viral particle, or a cell or a tissue expressing the antigen, and does not significantly cross-react with other proteins, such as other herpes virus proteins. The extent of binding of the antibody or oligopeptide to a "non-target" protein will often be less than about 10% of the binding of the antibody or oligopeptide to its target protein as determined by fluorescence activated cell sorting (FACS) analysis or radioimmunoprecipitation (RIA). Regarding the binding of an antibody or oligopeptide to a target molecule, the terms "specific binding" or "specifically binds to" or "is specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or "is specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. The term "specific binding" may refer to binding where a molecule binds to a particular polypeptide or epitope on a particular polypeptide without substantially binding to any other polypeptide or polypeptide epitope.

An antibody or oligopeptide that "inhibits the growth of infected cells expressing an HBeAg" or a "growth inhibitory" antibody or oligopeptide is one which results in measurable growth inhibition of infected cells expressing or overexpressing the appropriate HBeAg. The HBeAg may be a transmembrane polypeptide expressed on the surface of an infected cell or may be a polypeptide that is produced and secreted by an infected cell. Preferred growth inhibitory anti-HBeAg antibodies or oligopeptides inhibit growth of HBeAg-expressing cells by greater than 20%, preferably from about 20% to about 50%, and even more preferably, by greater than 50% (e.g., from about 50% to about 100%) as compared to the appropriate control, the control typically being cells not treated with the antibody or oligopeptide being tested. Growth inhibition can be measured at an antibody concentration of about 0.1 to 30 mcg/ml or about 0.5 nM to 200 nM in cell culture, where the growth inhibition is determined 1-10 days after exposure of the cells to the antibody. Growth inhibition of cells in vivo can be determined in various ways such as is described in the Examples section below. The antibody is growth inhibitory in vivo if administration of the anti-HBeAg antibody at about 1 μg/kg to about 100 mg/kg body weight results in reduction in infected cells or inhibited HBV proliferation within about 1 day to 3 months from the first administration of the antibody, preferably within about 1 to 5 days.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. (USA) 95:652-56 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), may be performed.

An antibody or oligopeptide which "induces cell death" is one which causes a viable cell to become nonviable. The cell is one which expresses an HBeAg or is infected with HBV. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody or oligopeptide can induce cell death, loss of membrane integrity as evaluated by uptake of propidium iodide (PI), trypan blue (see Moore et al. Cytotechnology 17:1-11 (1995)) or 7AAD can be assessed relative to untreated cells.

A "HBeAg-expressing cell" is a cell which expresses an endogenous or transfected HBeAg which may include expression either on the cell surface or in a secreted form.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD, or IgM.

The word "label" when used herein refers to a detectable compound or composition which is conjugated directly or indirectly to an antibody or oligopeptide to generate a "labeled" antibody or oligopeptide. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32 and radioactive isotopes of Lu), chemotherapeutic agents, enzymes and fragments thereof such as nucleolytic enzymes, antibiotics, immune suppressants, and toxins such as small molecule toxins or enzymatically active toxins of bacterial, fungal, plant or animal origin, including fragments and/or variants thereof. An antiviral agent causes destruction of virus-infected cells.

A "growth inhibitory agent" when used herein refers to a compound or composition which inhibits growth of a cell, especially an HBV-infected cell, either in vitro or in vivo. Thus, the growth inhibitory agent may be one which significantly reduces the percentage of HBV-infected cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, -γ, and λ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

II. Compositions and Methods

A. Anti-HBeAg Antibodies

This disclosure provides anti-HBeAg antibodies which may find use herein as therapeutic and/or diagnostic agents. Exemplary antibodies include polyclonal, monoclonal, chimeric, humanized, bispecific, and heteroconjugate antibodies.

1. Polyclonal Antibodies

Polyclonal antibodies are preferably raised in animals by multiple subcutaneous or intraperitoneal injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, SOCl2, or R1N=C=NR, where R and R1 are different alkyl groups.

Animals are immunized against the antigen, immunogenic conjugates, or derivatives by combining, e.g., 100 mcg or 5 mcg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, California USA, and SP-2 and derivatives e.g., X63-Ag8-653 cells available from the American Type Culture Collection, Manassas, Virginia, USA. Human myeloma and mouse-human heteromyeloma cell lines also have been described for producing human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (MA) or enzyme-linked immunosorbent assay (ELISA). The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Plückthun, Immunol. Revs. 130:151-188 (1992).

Monoclonal antibodies or antibody fragments may be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 21:2265-66 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-HBeAg antibodies of this disclosure may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-25 (1986); Riechmann et al., Nature, 332:323-29 (1988); and Presta, Curr. Op. Struct. Biol., 2:593-96 (1992)).

Methods for humanizing non-human antibodies are known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is important to reduce antigenicity and HAMA response (human anti-mouse antibody) when the antibody is intended for human therapeutic use. According to the "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a framework region derived from the consensus sequence of all human antibodies of a subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

It is further important that antibodies be humanized with retention of high binding affinity for the antigen and other favorable biological properties. To achieve this goal, humanized antibodies may be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity or specificity for the target antigen(s), is achieved. In general, the hypervariable region residues are directly and most substantially involved in influencing antigen binding.

Various forms of humanized anti-HBeAg antibodies are contemplated. For example, the humanized antibody may be an antibody fragment, such as a Fab, which is optionally conjugated with one or more cytotoxic agent(s) to generate an immunoconjugate. Alternatively, the humanized antibody may be an intact antibody, such as an intact IgG1 antibody.

As an alternative to humanization, human antibodies can be generated. For example, it is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-58 (1993); Bruggemann et al., Year in Immuno. 7:33 (1993); U.S. Pat. Nos. 5,545, 806, 5,569,825, 5,591,669 (all of GenPharm); U.S. Pat. No. 5,545,807; and WO 97/17852.

Alternatively, phage display technology (McCafferty et al., Nature 348:552-53 (1990)) can be used to produce human antibodies and antibody fragments in vitro, from immunoglobulin variable (V) domain gene repertoires from unimmunized donors. Using this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-71 (1993). Several sources of V-gene segments can be used for phage display. Clackson et al., Nature, 352:624-28 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-97 (1991), or Griffith et al., EMBO J. 12:725-34 (1993). See, also, U.S. Pat. Nos. 5,565,332 and 5,573,905.

As discussed above, human antibodies may also be generated in vitro in activated B cells (see, for example, U.S. Pat. Nos. 5,567,610 and 5,229,275).

4. Antibody Fragments

In certain circumstances, there are advantages to using antibody fragments rather than whole antibodies. The smaller size of the fragments allows for rapid clearance, and may lead to improved access to HBV-infected cells or organs in a mammal.

Various techniques have been developed to produce antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., Bio/Technology 10:163-67 (1992)). Using another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques to produce antibody fragments will be apparent to the skilled practitioner. The antibody of choice may also be a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870. Such linear antibody fragments may be monospecific or bispecific.

5. Bispecific Antibodies

Bispecific antibodies have binding specificities for at least two different epitopes. Exemplary bispecific antibodies may bind to two different epitopes of a HBeAg protein. Other such antibodies may combine a HBeAg binding site with a binding site for another protein. Alternatively, an anti-HBeAg arm may be combined with an arm which binds to a triggering molecule on a leukocyte such as a T-cell receptor molecule (e.g. CD3) (see, e.g., Baeuerle, et al., Curr. Opin. Mol. Ther. 11(1):22-30 (2009)), or Fc receptors for IgG (FcγR), such as FcγRI (CD64), FcγRII (CD32) and FcγRIII (CD16), to focus and localize cellular defense mechanisms to the HBeAg-expressing cell. Bispecific antibodies may also be used to localize cytotoxic agents to HBV-infected cells which express HBeAg. These antibodies possess a HBeAg-binding arm and an arm which binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., F(ab')2 bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. Nos. 5,821,337 and 6,407,213 teach bispecific anti-ErbB2/anti-CD3 antibodies. Additional bispecific antibodies that bind an epitope on the CD3 antigen and a second epitope have been described in U.S. Pat. No. 5,078,998 (anti-CD3/tumor cell antigen); U.S. Pat. No. 5,601,819 (anti-CD3/IL-2R; anti-CD3/CD28; anti-CD3/CD45); U.S. Pat. No. 6,129,914 (anti-CD3/malignant B cell antigen); U.S. Pat. No. 7,112,324 (anti-CD3/CD19); U.S. Pat. No. 6,723,538 (anti-CD3/CCR5); U.S. Pat. No. 7,235,641 (anti-CD3/EpCAM); U.S. Pat. No. 7,262,276 (anti-CD3/ovarian tumor antigen); and U.S. Pat. No. 5,731,168 (anti-CD3/CD4IgG).

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-39 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-59 (1991).

Using a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, CH2, and CH3 regions. It is preferred to have the first heavy-chain constant region (CH1) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three-polypeptide fragment when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

Preferably, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh, Methods in Enzymology 121:210 (1986).

Using another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with several cross-linking techniques. Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med. 175: 217-25 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed could bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., J. Immunol. 148(5):1547-53 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized to produce antibody homodimers. The "diabody" technology described by Hollinger et al., Proc. Natl. Acad. Sci. USA 90:6444-48 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments using single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147:60 (1991).

6. Heteroconjugate Antibodies

Heteroconjugate antibodies are also within the scope of this disclosure. Heteroconjugate antibodies are composed of two covalently joined antibodies. Such antibodies have been proposed to target immune system cells to unwanted cells (see U.S. Pat. No. 4,676,980), and for treatment of HIV infection (see WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of this disclosure may be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)
n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody preferably further comprises at least two (and preferably four) light chain variable domain polypeptides. The multivalent antibody may comprise from about two to about eight light chain variable domain polypeptides. The light chain variable domain polypeptides contemplated here comprise a light chain variable domain and, optionally, further comprise a $C_L$ domain.

8. Effector Function Engineering

It may be desirable to modify the antibodies of this disclosure with respect to effector function, e.g., to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-95 (1992) and Shopes, B. J. Immunol. 148:2918-22 (1992). Homodimeric antibodies with enhanced anti-viral activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-30 (1989).

To increase the serum half-life of the antibody, a salvage receptor binding epitope may be incorporated into the antibody (especially an antibody fragment) as described in U.S. Pat. No. 5,739,277. The term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

9. Immunoconjugates

The disclosure also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate). Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

This disclosure further contemplates an immunoconjugate formed between an antibody and a compound with nucleolytic activity (e.g., a ribonuclease or a DNA endonuclease such as a deoxyribonuclease; DNase).

For selective destruction of an HBV-infected cell, the antibody may comprise a radioactive atom. A variety of radioactive isotopes are available to produce radioconjugated anti-HBeAg antibodies. Examples include At211, 1131, I125, Y90, Re186, Re188, Sm153, Bi212, P32, Pb212 and radioactive isotopes of Lu. When the conjugate is used for diagnosis, it may comprise a radioactive atom for scintigraphic studies, for example tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the disclosure expressly contemplate, but are not limited to, an ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate) which are commercially available from Pierce Biotechnology, Inc., Rockford, IL).

Alternatively, a fusion protein comprising the anti-HBeAg antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The antibody may also be conjugated to a "receptor" (such streptavidin) for utilization in pre-targeting of viral infected cells, wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-HBeAg antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of this disclosure can be conjugated to the liposomes as described in Martin et al., J. Biol. Chem. 257:286-288 (1982) via a disulfide interchange reaction. A chemotherapeutic agent is optionally contained within the liposome. See Gabizon et al., J. National Cancer Inst. 81(19):1484 (1989).

B. HBeAg Binding Oligopeptides

HBeAg binding oligopeptides of this disclosure are oligopeptides that bind, preferably specifically, to an HBeAg. HBeAg binding oligopeptides may be chemically synthesized using known oligopeptide synthesis methodology or may be prepared and purified using recombinant technology. HBeAg binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to an HBeAg. HBeAg binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

Bacteriophage (phage) display is one known technique used to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) Science 249:386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., Gene, 215:439 (1998); Zhu et al., Cancer Research, 58(15): 3209-14 (1998); Jiang et al., Infection & Immunity, 65(11): 4770-77 (1997); Ren et al., Gene, 195(2):303-11 (1997); Ren, Protein Sci., 5: 1833 (1996); Efimov et al., Virus Genes, 10:173 (1995)) and T7 phage display systems (Smith and Scott, Methods in Enzymology, 217: 228-57 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of Staphlylococcus aureus protein A as an affinity tag has also been reported (Li et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. Screening for Anti-HBeAg Antibodies and HBeAg Binding Oligopeptides with the Desired Properties Techniques for generating antibodies or oligopeptides that bind to HBeAgs have been described above. One may further select antibodies or oligopeptides with certain biological characteristics, as desired.

The growth inhibitory effects of an anti-HBeAg antibody of this disclosure may be assessed by methods known in the art, e.g., using cells which express an HBeAg either endogenously or following transfection with the HBeAg gene. For example, appropriate HBV infected cells may be treated with an anti-HBeAg monoclonal antibody or oligopeptide of this disclosure at various concentrations for a few days (e.g., 2-7) and stained with crystal violet or MTT or analyzed by some other colorimetric assay. Another method of measuring proliferation would be by comparing 3H-thymidine uptake by the cells treated in the presence or absence an anti-HBeAg antibody, or HBeAg binding oligopeptide of the disclosure. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of infected cells in vivo can be determined in various ways known in the art. Preferably, the anti-HBeAg antibody, or HBeAg binding oligopeptide will inhibit cell proliferation of an HBV infected cell in vitro or in vivo by about 25-100% compared to the untreated infected cell, more preferably, by about 30-100%, and even more preferably by about 50-100% or 70-100%. Growth inhibition can be measured at an antibody concentration of about 0.5 to 30 µg/ml or about 0.5 nM to 200 nM in cell culture, where the growth inhibition is determined 1-10 days after exposure of the cells to the antibody. The antibody is growth inhibitory in vivo if administration of the anti-HBeAg antibody at about 1 µg/kg to about 100 mg/kg body weight results in reduction in cell growth or proliferation within about 5 days to 3 months from the first administration of the antibody, preferably within about 5 to 30 days.

To select for an anti-HBeAg antibody, HBeAg binding oligopeptide which induces cell death, loss of membrane integrity as indicated by, e.g., propidium iodide (PI), trypan blue or 7AAD uptake may be assessed relative to control. A PI uptake assay can be performed in the absence of complement and immune effector cells. HBeAg-expressing cells are incubated with medium alone or medium containing the appropriate anti-HBeAg antibody (e.g., at about 10 µg/ml), HBeAg binding oligopeptide. The cells are incubated for a 3-day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those anti-HBeAg antibodies, or HBeAg binding oligopeptides that induce statistically significant levels of cell death as determined by PI uptake may be selected as cell death-inducing anti-HBeAg antibodies or HBeAg binding oligopeptides.

To screen for antibodies or oligopeptides which bind to an epitope on an HBeAg bound by an antibody of interest, a cross-blocking assay such as that described in Antibodies, A Laboratory Manual, Cold Spring Harbor Laboratory, Ed Harlow and David Lane (1988), can be performed. This assay can be used to determine if a test antibody or oligopeptide binds the same site or epitope as a known anti-HBeAg antibody. Alternatively or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of an HBeAg can be used in competition assays with the test antibodies or with a test antibody and an antibody with a characterized or known epitope.

D. Anti-HBeAg Antibody and HBeAg Binding Oligopeptide Variants

In addition to the anti-HBeAg antibodies described herein, it is contemplated that anti-HBeAg antibody variants can be prepared. Anti-HBeAg antibody variants can be prepared by introducing appropriate nucleotide changes into the encoding DNA, and/or by synthesis of the desired antibody or polypeptide. Those skilled in the art will appreciate that amino acid changes may alter post-translational processes of the anti-HBeAg antibody, such as changing the number or position of glycosylation sites or altering the membrane anchoring characteristics.

Variations in the anti-HBeAg antibodies described herein can be made, for example, using any of the techniques and guidelines for conservative and non-conservative mutations set forth, for instance, in U.S. Pat. No. 5,364,934. Variations may be a substitution, deletion, or insertion of one or more codons encoding the antibody or polypeptide that results in a change in the amino acid sequence as compared with the native sequence antibody or polypeptide. Optionally, the variation is by substitution of at least one amino acid with any other amino acid in one or more of the domains of the anti-HBeAg antibody. Guidance in determining which amino acid residue may be inserted, substituted or deleted without adversely affecting the desired activity may be found by comparing the sequence of the anti-HBeAg antibody with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions, or substitutions of amino acids in the sequence and testing the resulting variants for activity exhibited by the full-length or mature native sequence.

Anti-HBeAg antibody fragments are provided herein. Such fragments may be truncated at the N-terminus or C-terminus, or may lack internal residues, for example, when compared with a full length native antibody. Certain fragments lack amino acid residues that are not essential for a desired biological activity of the anti-HBeAg antibody.

Anti-HBeAg antibody fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR.

Preferably, anti-HBeAg antibody fragments share at least one biological and/or immunological activity with the native anti-HBeAg antibodies disclosed herein.

Conservative substitutions of interest are shown in the following table under the heading of preferred substitutions. If such substitutions result in a change in biological activity, then more substantial changes, denominated exemplary substitutions in this table, or as further described below in reference to amino acid classes, are introduced and the products screened.

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the anti-HBeAg antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
    (2) neutral hydrophilic: Cys, Ser, Thr; Asn; Gln
    (3) acidic: Asp, Glu;
    (4) basic: His, Lys, Arg;
    (5) residues that influence chain orientation: Gly, Pro; and
    (6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the anti-HBeAg antibody variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, Science, 244:1081-85 (1989)). Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isoteric amino acid can be used.

Any cysteine residue not involved in maintaining the proper conformation of the anti-HBeAg antibody also may be substituted, generally with serine, to improve the oxidative stability of the molecule and prevent aberrant crosslinking. Conversely, cysteine bond(s) may be added to the anti-HBeAg antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. To identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and HBeAg. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-HBeAg antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-HBeAg antibody.

E. Modifications of Anti-HBeAg Antibodies

Covalent modifications of anti-HBeAg antibodies and HBeAgs are included within the scope of this disclosure. One type of covalent modification includes reacting targeted amino acid residues of an anti-HBeAg antibody with an organic derivatizing agent that can react with selected side chains or the N- or C-terminal residues of the anti-HBeAg antibody. Derivatization with bifunctional agents is useful, for instance, for crosslinking anti-HBeAg antibody to a water-insoluble support matrix or surface for use in purifying anti-HBeAg antibodies, or detection of HBeAg protein in biological samples, or HBV diagnostic assays. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of the anti-HBeAg antibody included within the scope of this disclosure comprises altering the native glycosylation pattern of the antibody or polypeptide. "Altering the native glycosylation pattern" is intended for purposes herein to mean deleting one or more carbohydrate moieties found in native sequence anti-HBeAg antibody (either by removing the underlying glycosylation site or by deleting the glycosylation by chemical and/or enzymatic means), and/or adding one or more glycosylation sites that are not present in the native sequence anti-HBeAg antibody. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetyl galactosamine, galactose, or xylose to a hydroxyamino acid, most commonly serine or threonine, although 5-hydroxyproline or 5-hydroxylysine may also be used.

Addition of glycosylation sites to the anti-HBeAg antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-HBeAg antibody (for O-linked glycosylation sites). The anti-HBeAg antibody amino acid sequence may optionally be altered through changes at the DNA level, particularly by mutating the DNA encoding the anti-HBeAg antibody at preselected bases such that codons are generated that will translate into the desired amino acids.

Another means of increasing the number of carbohydrate moieties on the anti-HBeAg antibody is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the anti-HBeAg antibody may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved using a variety of endo- and exo-glycosidases as described by Thotakura et al., Meth. Enzymol., 138:350 (1987).

Another type of covalent modification of anti-HBeAg antibody comprises linking the antibody or polypeptide to one of a variety of nonproteinaceous polymers, e.g., polyethylene glycol (PEG), polypropylene glycol, or polyoxyalkylenes, in the manner set forth in U.S. Pat. Nos. 4,640, 835; 4,496,689; 4,301,144; 4,670,417; 4,791,192 or 4,179, 337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-HBeAg antibody of this disclosure may also be modified in a way to form chimeric molecules comprising an anti-HBeAg antibody fused to another, heterologous polypeptide or amino acid sequence.

Such a chimeric molecule may comprise a fusion of the anti-HBeAg antibody with a tag polypeptide which provides an epitope to which an anti-tag antibody can selectively bind. The epitope tag is generally placed at the amino- or carboxyl-terminus of the anti-HBeAg antibody. The presence of such epitope-tagged forms of the anti-HBeAg antibody can be detected using an antibody against the tag polypeptide. Also, provision of the epitope tag enables the anti-HBeAg antibody to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto (Evan et al., Molecular and Cellular Biology, 5:3610-16 (1985)); and the Herpes Simplex virus glycoprotein D (gD) tag and its antibody (Paborsky et al., Protein Engineering, 3(6):547-553 (1990)). Other tag polypeptides include the Flag-peptide (Hopp et al., BioTechnology, 6:1204-10 (1988)); the KT3 epitope peptide (Martin et al., Science, 255:192-194 (1992)); an α-tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)).

Alternatively, the chimeric molecule may comprise a fusion of the anti-HBeAg antibody with an immunoglobulin or a region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-HBeAg antibody in place of at least one variable region within an Ig molecule. Preferably, the immunoglobulin fusion includes the hinge, CH2 and CH3, or the hinge, CHL CH2 and CH3 regions of an IgG1 molecule. For the production of immunoglobulin fusions, see also U.S. Pat. No. 5,428,130.

F. Preparation of Anti-HBeAg Antibodies and HBeAg binding Oligopeptides

The description below relates primarily to production of anti-HBeAg antibodies and HBeAg binding oligopeptides by culturing cells transformed or transfected with a vector containing anti-HBeAg antibody, or HBeAg binding oligopeptide-encoding nucleic acid. It is, of course, contemplated that alternative methods, which are well known in the art, may be employed to prepare anti-HBeAg antibodies and HBeAg binding oligopeptides. For instance, the appropriate amino acid sequence, or portions thereof, may be produced by direct peptide synthesis using solid-phase techniques (e.g., Stewart et al., Solid-Phase Peptide Synthesis, W.H. Freeman Co., San Francisco, CA (1969); Merrifield, J. Am. Chem. Soc., 85:2149-54 (1963)). In vitro protein synthesis may be performed using manual techniques or by automation. Automated synthesis may be accomplished, for instance, using an Applied Biosystems Peptide Synthesizer (Foster City, CA) using manufacturer's instructions. Various portions of the anti-HBeAg antibody may be chemically synthesized separately and combined using chemical or enzymatic methods to produce the desired anti-HBeAg antibody.

1. Isolation of DNA Encoding Anti-HBeAg Antibody

DNA encoding anti-HBeAg antibody may be obtained from a cDNA library prepared from tissue believed to possess the anti-HBeAg antibody mRNA and to express it at a detectable level. Accordingly, human anti-HBeAg antibody DNA can be conveniently obtained from a cDNA library prepared from human tissue. The anti-HBeAg antibody-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding anti-HBeAg antibody is to use PCR methodology [Sambrook et al., supra; Dieffenbach et al., PCR Primer: A Laboratory Manual (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like 32P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acids having protein coding sequences may be obtained by screening selected cDNA or genomic libraries using the deduced amino acid sequence, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-HBeAg antibody production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated, and electroporation. Depending on the host cell used, transformation is performed using standard techniques appropriate to such cells. The calcium treatment employing calcium chloride, as described in Sambrook et al., supra, or electroporation is generally used for prokaryotes. Infection with Agrobacterium tumefaciens is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For techniques for transforming mammalian cells, see Keown et al., Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as E. coli. Various E. coli strains are publicly available, such as E. coli K12 strain MM294 (ATCC 31,446); E. coli X1776 (ATCC 31,537); E. coli strain W3110 (ATCC 27,325) and K5 772 (ATCC 53,635). Other suitable prokaryotic host cells include Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis (e.g., B. licheniformis 41P disclosed in DD 266,710 published 12 Apr. 1989), Pseudomonas such as P. aeruginosa, and Streptomyces. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including E. coli W3110 strain 1A2, which has the complete genotype tonA; E. coli W3110 strain 9E4, which has the complete genotype tonA ptr3; E. coli W3110 strain 27C7 (ATCC 55,244), which has the complete genotype tonA ptr3 phoA E15 (argF-lac)169 degP ompT kanr; E. coli W3110 strain 37D6, which has the complete genotype tonA ptr3 phoA E15 (argF-lac)169 degP ompT rbs7 ilvG kanr; E. coli W3110 strain 40B4, which is strain 37D6 with a non-kanamycin resistant degP deletion mutation; and an E. coli strain having mutant periplasmic protease disclosed in U.S. Pat. No. 4,946,783. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in HBV or HBV-infected cell destruction. Full length antibodies have greater half-life in circulation. Production in E. coli is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the E. coli cell paste in a soluble fraction and can be purified through, e.g., a protein A or G column depending on the isotype. Final purification can be carried out similar to the process for purifying antibody expressed, e.g., in CHO cells.

In addition to prokaryotes, eukaryotic microbes such as filamentous fungi or yeast are suitable cloning or expression hosts for anti-HBeAg antibody-encoding vectors. Saccharomyces cerevisiae is a commonly used lower eukaryotic host microorganism. Others include Schizosaccharomyces pombe (Beach and Nurse, Nature, 290: 140 [1981]; EP 139,383 published 2 May 1985); Kluyveromyces hosts (U.S. Pat. No. 4,943,529; Fleer et al., Bio/Technology, 9:968-975 (1991)) such as, e.g., K. lactis (MW98-8C, CBS683, CBS4574; Louvencourt et al., J. Bacteriol., 154(2):737-742 [1983]), K. fragilis (ATCC 12,424), K. bulgaricus (ATCC 16,045), K. wickeramii (ATCC 24,178), K. waltii (ATCC 56,500), K. drosophilarum (ATCC 36,906; Van den Berg et al., Bio/Technology, 8:135 (1990)), K. thermotolerans, and K. marxianus; yarrowia (EP 402,226); Pichia pastoris (EP 183,070; Sreekrishna et al., J. Basic Microbiol., 28:265-278 [1988]); Candida; Trichoderma reesia (EP 244,234); Neurospora crassa (Case et al., Proc. Natl. Acad. Sci. USA, 76:5259-5263 [1979]); Schwanniomyces such as Schwanniomyces occidentalis (EP 394,538 published 31 Oct. 1990); and filamentous fungi such as, e.g., Neurospora, Penicillium, Tolypocladium (WO 91/00357 published 10 Jan. 1991), and Aspergillus hosts such as A. nidulans (Ballance et al., Biochem. Biophys. Res. Commun., 112:284-289 [1983]; Tilburn et al., Gene, 26:205-221 [1983]; Yelton et al., Proc. Natl. Acad. Sci. USA, 81: 1470-1474 [1984]) and A. niger (Kelly and Hynes, EMBO J., 4:475-479 [1985]). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, The Biochemistry of Methylotrophs, 269 (1982).

Suitable host cells for the expression of glycosylated anti-HBeAg antibody are derived from multicellular organisms. Examples of invertebrate cells include insect cells such as *Drosophila* S2 and *Spodoptera* Sf9, as well as plant cells, such as cell cultures of cotton, corn, potato, soybean, *petunia*, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to this disclosure, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-HBeAg antibody production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding anti-HBeAg antibody may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The anti-HBeAg monoclonal antibodies may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-HBeAg antibody-encoding DNA that is inserted into the vector. The signal sequence may be a prokaryotic signal sequence selected, for example, from the group of the alkaline phosphatase, penicillinase, 1 pp, or heat-stable enterotoxin II leaders. For yeast secretion, the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the anti-HBeAg antibody-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 [Stinchcomb et al., Nature, 282:39 (1979); Kingsman et al., Gene, 7:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 (Jones, Genetics, 85:12 (1977)).

Expression and cloning vectors usually contain a promoter operably linked to the anti-HBeAg antibody-encoding nucleic acid sequence to direct mRNA synthesis. Promoters recognized by a variety of potential host cells are well known. Promoters suitable for use with prokaryotic hosts include the β-lactamase and lactose promoter systems (Chang et al., Nature, 275:615 (1978); Goeddel et al., Nature, 281:544 (1979)), alkaline phosphatase, a tryptophan (trp) promoter system (Goeddel, Nucleic Acids Res., 8:4057 (1980)), and hybrid promoters such as the tac promoter (deBoer et al., Proc. Natl. Acad. Sci. USA, 80:21-25 (1983)). Promoters for use in bacterial systems also will contain a Shine-Dalgarno sequence operably linked to the DNA encoding anti-HBeAg antibody.

Examples of suitable promoting sequences for use with yeast hosts include the promoters for 3-phosphoglycerate kinase (Hitzeman et al., J. Biol. Chem., 255:2073 (1980)) or other glycolytic enzymes (Hess et al., J. Adv. Enzyme Reg., 7:149 (1968); Holland, Biochemistry, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-HBeAg antibody transcription from vectors in mammalian host cells is controlled, for example, by promoters obtained from the genomes of viruses such as polyoma virus, fowlpox virus (UK 2,211,504), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the anti-HBeAg antibody by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the anti-HBeAg antibody coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-HBeAg antibody.

Still other methods, vectors, and host cells suitable for adaptation to the synthesis of anti-HBeAg antibody in recombinant vertebrate cell culture are described in Gething et al., Nature, 293:620-25 (1981); Mantei et al., Nature, 281:40-46 (1979); EP 117,060; and EP 117,058.

4. Culturing the Host Cells

The host cells used to produce the anti-HBeAg antibody of this disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA (Thomas, Proc. Natl. Acad. Sci. USA, 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence HBeAg or against a synthetic peptide based on the DNA sequences provided herein or against exogenous sequence fused to HBeAg DNA and encoding a specific antibody epitope.

6. Purification of Anti-HBeAg Antibodies and HBeAg Binding Oligopeptides

Forms of anti-HBeAg antibody may be recovered from culture medium or from host cell lysates. If membrane-bound, it can be released from the membrane using a suitable detergent solution (e.g. Triton-X 100) or by enzymatic cleavage. Cells employed in expression of anti-HBeAg antibody can be disrupted by physical or chemical means, such as freeze-thaw cycling, sonication, mechanical disruption, or cell lysing agents.

It may be desired to purify anti-HBeAg antibody from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-HBeAg antibody and HBeAg. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the anti-HBeAg antibody produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$ or $\gamma 4$ heavy chains (Lindmark et al., J. Immunol. Meth. 62:1-13 (1983)). Protein G is recommended for all mouse isotypes and for human $\gamma 3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, NJ) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

G. Pharmaceutical Formulations

Therapeutic formulations of the anti-HBeAg antibodies or HBeAg binding oligopeptides of this disclosure are prepared for storage by mixing the antibody, polypeptide, or oligopeptide having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or nonionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the indication being treated, preferably those with complementary activities that do not adversely affect each other. For example, in addition to an anti-HBeAg antibody or HBeAg binding oligopeptide, it may be desirable to include in the one formulation, an additional antibody, e.g., a second anti-HBeAg antibody which binds a different epitope on the HBeAg. Alternatively, or additionally, the composition may further comprise a cytokine, an anti-inflammatory agent, or an interferon. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and $\gamma$ ethyl-L-glutamate, nondegradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

H. Diagnosis and Treatment with Anti-HBeAg Antibodies or HBeAg Binding Oligopeptides HBeAg expression may be evaluated using an in vivo diagnostic assay, e.g., by administering a molecule (such as an anti-HBeAg antibody or HBeAg binding oligopeptide) which binds the molecule to be detected and is tagged with a detectable label (e.g., a radioactive isotope or a fluorescent label) and externally scanning the patient for localization of the label.

As described above, the anti-HBeAg antibodies or oligopeptides of this disclosure have various non-therapeutic applications. The anti-HBeAg antibodies or oligopeptides of this disclosure are useful for diagnosis and staging of HBV infections. The antibodies or oligopeptides are also useful for purification or immunoprecipitation of HBeAg from cells, for detection and quantitation of HBeAg in vitro, e.g., in an ELISA or a Western blot, to kill and eliminate HBeAg-expressing cells from a population of mixed cells as a step in the purification of other cells.

An exemplary method of detection of HBeAg in a biological sample, (which method may therefore be diagnostic of chronic HBV infection) is a sandwich ELISA, in which the antibody is bound to the solid phase or support, which is then contacted with the biological sample being tested to extract the antigen from the sample by formation of a binary solid phase antibody:antigen complex. After a suitable incubation period, the solid support is washed to remove the residue of the fluid sample and then contacted with a solution containing a known quantity of labeled antibody. The label is then detected to provide a quantitative assessment of the antigen in the biological sample. Based on testing results described in detail below, the pairing of Mab e6 Fab and Fab e13 for capture and detection, respectively, of HBeAg was found to be the best combination for sandwich ELISA detection of HBeAg in human plasma samples.

Another exemplary method of detection of HBeAg in a biological sample, (which method may therefore be diagnostic of chronic HBV infection) is an epitope blocking ELISA (EB ELISA), in which methods specific antibodies from positive sera inhibit a selected mAb from recognizing its specific epitope such that color development is inhibited when a color-producing reagent which binds to the selected mAb is added to the sample. Negative sera, however, allow a strong color reaction. The assay depends on the ability of anti-HBeAg antibodies present in the biological sample to block binding of a selected HBe-antigen mAb to HB-e antigens or recombinant antigens adsorbed on a micro titer plate. More specifically, in an EB ELISA of this disclosure, ELISA plates are coated with an optimal concentration of recombinant HBeAg or an inactivated HBV strain in a coating buffer. An optimal concentration can be determined by using a checkerboard titration by two-dimensional serial dilution of coating antigen and a known positive antibody and selecting the most favorable concentration which gives maximal optical density (O.D.) value in the ELISA reading. Test sera samples are added to each well of the coated plates and incubated, washed and then incubated with supernatant from an anti-HBeAg mAb of this disclosure. Plates may be washed again and the bound mAb is detected by the addition of diluted horseradish peroxidase (HRP)-labeled antibody, such as an HRP-labeled rabbit anti-mouse antibody, which binds to the mAb. The plates may be washed and then incubated with 3,3',5,5'-tetramethyl benzidine or other color-producing reagent, such as 2,2-Azino-bis(3-ethylbenzothiazoline-6-sulfonic acid) or o-phenylenediamine dihydrochloride. The reaction is stopped and the color development read. The percent inhibition of the colorimetric reaction caused by antibodies in the sample which block the binding of the mAb to the antigen is calculated for each serum sample. These EB ELISA testing methods provide a convenient, highly specific and sensitive means for detecting HBV virus (specifically HBeAg) and may detect lower levels of antibody (or CHB infection) than can be consistently detected in other tests.

Currently, HBV infection prevention and treatment involves preventing transmission of the virus, vaccination, or administration of interferons. Anti-HBeAg antibody or oligopeptide therapy (such as by passive immunotherapy) may be especially desirable in elderly patients or immuno-compromised patients or pregnant patients who may not tolerate the side effects of vaccination or vaccine components or interferons, or who cannot mount an immunological response.

A conjugate comprising an anti-HBeAg antibody or oligopeptide conjugated with a cytotoxic agent may be administered to the patient. Preferably, the immunoconjugate bound to the anti-HBeAg antibody is internalized by the cell, resulting in increased therapeutic efficacy of the immunoconjugate in killing the infected cell to which it binds. Preferably, the cytotoxic agent targets or interferes with the nucleic acid in the infected cell. The anti-HBeAg antibodies or oligopeptides or conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody or oligopeptide is preferred.

Other therapeutic regimens may be combined with the administration of the anti-HBeAg antibody or oligopeptide. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-HBeAg antibody or antibodies or oligopeptides with administration of an antibody directed against another HBV antigen.

The therapeutic treatment methods of this disclosure may include the combined administration of an anti-HBeAg antibody (or antibodies) or oligopeptides and an interferon.

For the prevention or treatment of HBV infection or HBV-associated disease, the dosage and mode of administration of these antibodies and therapeutic proteins will be chosen by the medical provider according to known criteria. The appropriate dosage of antibody or oligopeptide will depend on the type of disease to be treated, as defined above, the severity and course of the disease, whether the antibody or oligopeptide is administered for preventive or therapeutic purposes, previous therapy, the patient's clinical history and response to the antibody or oligopeptide and the discretion of the medical provider. The antibody or oligopeptide is suitably administered to the patient at one time or over a series of treatments. Preferably, the antibody or oligopeptide is administered by intravenous infusion or by subcutaneous injections. Depending on the type and severity of the disease, about 1 mcg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-HBeAg antibody. However, other dosage regimens may be useful. A typical daily dosage might range from about 1 mcg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to medical providers of skill in the art.

Aside from administration of the anti-HBeAg antibody to a patient, this disclosure contemplates administration of the antibody by gene therapy. Such administration of nucleic acid encoding the antibody is encompassed by the expression "administering a therapeutically effective amount of an antibody." See, for example, WO96/07321 concerning the use of gene therapy to generate intracellular antibodies.

There are two major approaches to getting the nucleic acid (optionally contained in a vector) into the patient's cells; in vivo and ex vivo. For in vivo delivery, the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

The anti-HBeAg antibodies of the disclosure can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail above, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, to minimize side effects or therapeutic complications, certain other Fc regions may be used.

These antibodies may include an antibody that competes for binding or binds substantially to, the same epitope as the antibodies of the disclosure. Antibodies having the biological characteristics of the present anti-HBeAg antibodies of this disclosure are also contemplated, specifically including the in vivo targeting, and infection inhibiting or preventing, or cytotoxic characteristics.

The present anti-HBeAg antibodies or oligopeptides are useful for treating an HBV infection or alleviating one or more symptoms of the infection in a mammal. The antibody or oligopeptide can bind to at least a portion of an infected cell that express HBeAg in the mammal. Preferably, the antibody or oligopeptide is effective to destroy or kill HBeAg-expressing cells or inhibit the growth of such cells, in vitro or in vivo, upon binding to HBeAg on the cell. Such an antibody includes a naked anti-HBeAg antibody (not conjugated to any agent). Naked antibodies that have cytotoxic or cell growth inhibition properties can be further harnessed with a cytotoxic agent to render them even more potent in HBV or HBV-infected cell destruction. Cytotoxic properties can be conferred to an anti-HBeAg antibody by, e.g., conjugating the antibody with a cytotoxic agent, to form an immunoconjugate as described herein. The cytotoxic agent or a growth inhibitory agent is preferably a small molecule.

This disclosure also provides a composition comprising an anti-HBeAg antibody or oligopeptide of the disclosure, and a carrier. For the purposes of treating HBV infection, compositions can be administered to the patient in need of such treatment, wherein the composition can comprise one or more anti-HBeAg antibodies present as an immunoconjugate or as the naked antibody. The compositions may comprise these antibodies or oligopeptides in combination with other therapeutic agents. The formulation may be a therapeutic formulation comprising a pharmaceutically acceptable carrier.

This disclosure also provides isolated nucleic acids encoding the anti-HBeAg antibodies. Nucleic acids encoding both the H and L chains and especially the hypervariable region residues, chains which encode the native sequence antibody as well as variants, modifications and humanized versions of the antibody, are encompassed.

The disclosure also provides methods useful for treating an HBV infection or alleviating one or more symptoms of the infection in a mammal, comprising administering a therapeutically effective amount of an anti-HBeAg antibody or oligopeptide of this disclosure to the mammal. The antibody or oligopeptide therapeutic compositions can be administered short term (acutely) or chronically, or intermittently as directed by a medical professional. Also provided are methods of inhibiting the growth of, and killing an HBeAg-expressing cell.

J. Articles of Manufacture and Kits

This disclosure also provides assay devices, kits, and articles of manufacture comprising at least one anti-HBeAg antibody or oligopeptide of this disclosure, optionally linked to a label, such as a fluorescent or radiolabel. The articles of manufacture may contain materials useful for the detection, diagnosis, or treatment of HBV infection. A preferred device is a lateral flow assay device which provides for point-of-care detection and/or diagnosis of an HBV infection. The article of manufacture comprises a container and a label or package insert on or associated with the container. Suitable containers include, for example, bottles, vials, syringes, etc. The containers may be formed from a variety of materials such as glass or plastic. The container holds a composition which is effective for detecting or treating the HBV infection and may have a sterile access port (for example the container may be an intravenous solution bag or a vial having a stopper pierceable by a hypodermic injection needle). At least one active agent in the composition is an anti-HBeAg antibody or oligopeptide of this disclosure. The label or package insert indicates that the composition is used for detecting or treating HBV infection. The label or package insert may further comprise instructions for using the antibody or oligopeptide composition, e.g., in the testing or treating of the infected patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for HBV-infected cell killing assays, for purification, or immunoprecipitation of HBeAg from cells. For isolation and purification of HBeAg, the kit can contain an anti-HBeAg antibodies or oligopeptides coupled to beads (e.g., sepharose beads). Kits can be provided which contain the antibodies or oligopeptides for detection and quantitation of HBeAg in vitro, e.g., in an ELISA or a Western blot. As with the article of manufacture, the kit comprises a container and a label or package insert on or associated with the container. The container holds a composition comprising at least one anti-HBeAg antibody or oligopeptide of the disclosure. Additional containers may be included that contain, e.g., diluents and buffers, control antibodies. The label or package insert may provide a description of the composition as well as instructions for the intended in vitro or diagnostic use.

Exemplary kits of this disclosure will contain at least one anti-HBeAg mAb or related binding protein of this disclosure, components for detecting immunospecific binding of the mAb or related binding protein to HBeAg in a biological sample, and instructions for use, depending upon the method selected, such as epitope blocking, competitive, sandwich, and the like. These kits also may contain positive and negative controls. They may also be configured to be used with automated analyzers or automated immunohistochemical slide staining instruments. A preferred kit is one to be used in a sandwich ELISA, as depicted in FIG. 6C. Another preferred kit is one to be used in an epitope blocking ELISA. Such kits comprise a mAb or related binding protein which binds to an HBeAg epitope, and reagents for detecting binding of said binding protein to said epitope.

The anti-HBeAg antibody or oligopeptide of this disclosure may also be provided as part of an assay device. Such assay devices include lateral flow assay devices. A common type of disposable lateral flow assay device includes a zone or area for receiving the liquid sample, a conjugate zone, and a reaction zone. These assay devices are commonly known as lateral flow test strips. They employ a porous material, e.g., nitrocellulose, defining a path for fluid flow capable of supporting capillary flow. Examples include those described in U.S. Pat. Nos. 5,559,041, 5,714,389, 5,120,643, and 6,228,660 all of which are incorporated herein by reference in their entireties. The anti-HBeAg antibody or oligopeptide of this disclosure may also be used in a lateral flow assay device in conjunction with other antibodies to detect multiple HBV proteins or other herpesvirus proteins using a single biological sample from a subject or patient being tested on one portable, point-of-care device.

Another type of assay device is a non-porous assay device having projections to induce capillary flow. Examples of such assay devices include the open lateral flow device as disclosed in PCT International Publication Nos. WO 2003/103835, WO 2005/089082, WO 2005/118139, and WO 2006/137785, all of which are incorporated herein by reference in their entireties.

All patent and literature references cited in the present specification are hereby incorporated by reference in their entirety.

The foregoing disclosure is sufficient to enable one skilled in the art to practice the invention. The present invention is not to be limited in scope by the constructs described, because the described embodiments are illustrations of certain aspects of the invention and any constructs that are functionally equivalent are within the scope of this invention.

EXAMPLES

The inventors generated chimeric rabbit/human monoclonal antibody fragments directed against the recombinant Hepatitis B e-antigen (rHBeAg) through phage display. Rabbit monoclonal antibodies often have both high affinity and specificity and can recognize epitopes conserved between human, rat and mouse antigens. The repertoire of chimeric Fab molecules produced in these studies, comprising rabbit variable domains and human constant domains, bind specifically to the rHBeAg. These 50 kDa chimeric Fab molecules can be fully humanized and converted to an IgG by fusion with Fc coding sequences. This can be advantageous in applications where greater size and/or bivalency are desired. Alternatively, the 50 kDa Fab can be downsized to a 25 kDa scFv, which is sometimes more suitable as a crystallization chaperone as it can form a more closely packed crystal.

Materials and Methods Used in these Studies

Figure 9A:
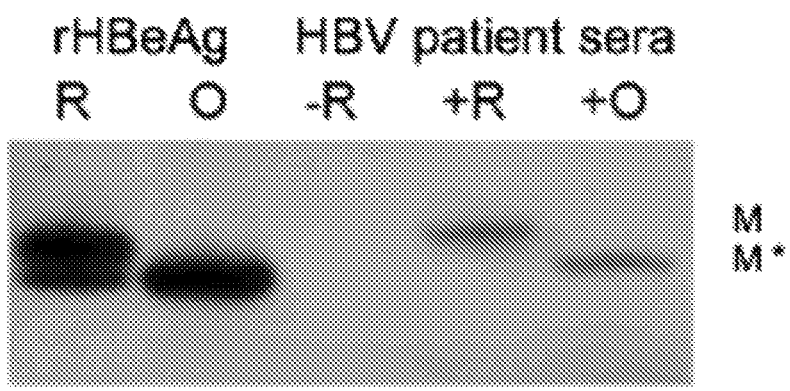
FIGS. 9A and 9B show immunoaffinity purification of HBeAg from HBV patient plasma.
Figure 9B:
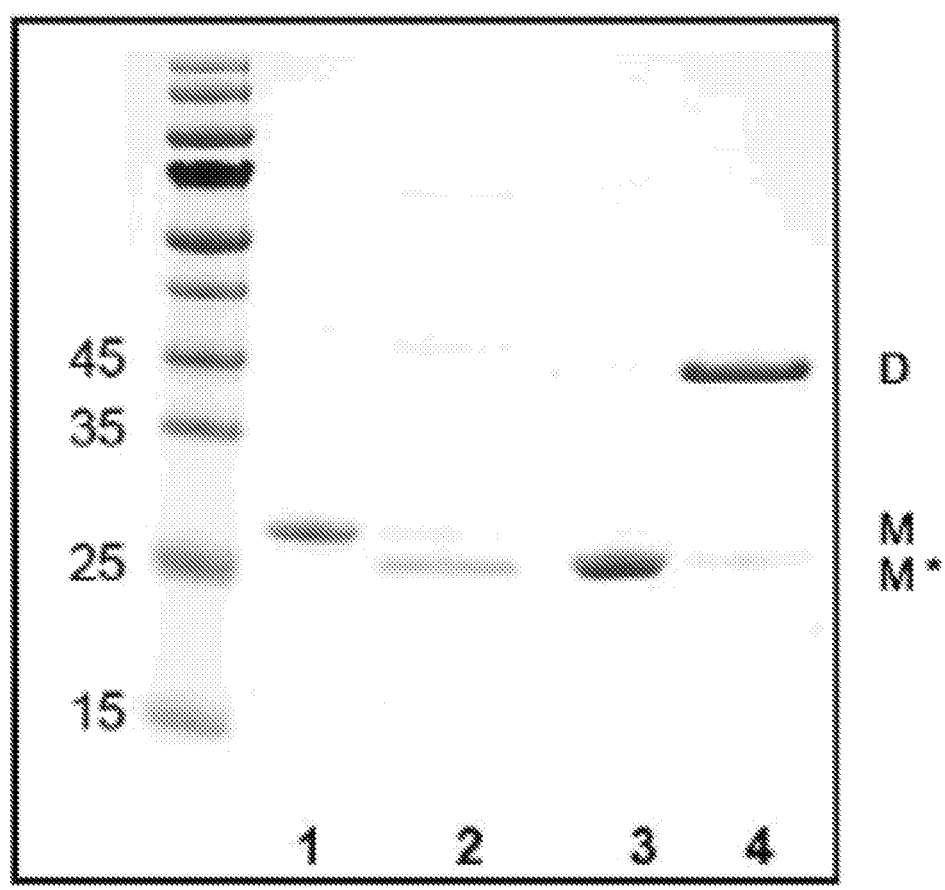

HBV Patient Plasmas. A total of 67 HBV patient plasma samples (35 HBeAg-positive and 32 HBeAg-negative) were obtained from the National Institutes of Health Clinical Center, in accordance with institutional policies for protection of human subjects. All plasma samples had been screened by the Clinical Center on the Ortho Clinical Vitros Eci immunodiagnostic system, and the HBeAg data corresponding to each of the plasma samples were provided.

rHBeAg. The *E. coli* expression and purification were performed as previously described (Watts, N. R., et al., (2010) *Molecular basis for the high degree of antigenic cross-reactivity between hepatitis B virus capsids (HBcAg) and dimeric capsid-related protein (HBeAg): insights into the enigmatic nature of the e-antigen*. J. Mol. Biol. 398, 530-541). We used the construct Cp(−10)-149.C48C.C107A (FIG. 1B). If the protein was not fully oxidized as judged by non-reducing SDS-PAGE (FIG. 9B) it was incubated with 1 μM CuCl$_2$ for 30 min, 5 mM EDTA added and re-chromatographed on Superdex 200 to remove any aggregated protein.

rHBeAg with Carboxyl-terminal Avi-tag. A rHBeAg construct with a 17-residue peptide biotin ligase substrate domain appended to the Carboxyl-terminus was expressed in *E. coli*. Protein purification was as described above. Biotinylation with biotin ligase (Avidity, LLC) was done according to the manufacturer's protocol. Following the reaction, the protein was gel filtrated on Superdex S200. The protein was characterized by mass spectrometry to confirm protein labeling.

rHBcAg. The construct Cp1-149.C48C.C107A (FIG. 1B), which corresponds to the capsid assembly domain, was produced as previously described and assembled into capsids (Watts, et al., (2010) J. Mol. Biol., supra). For many of the assays we used capsids assembled from Cp1-149.C48C.C107A dimers as surrogate HBcAg.

rHBsAg. The Small form (genotype D) was purified from recombinant yeast by immunoaffinity chromatography.

Selection of Anti-rHBeAg Chimeric Rabbit/Human Fab by Phage Display. The methods used were as previously described (Stahl, S. J., et al., (2010) *Generation and characterization of a chimeric rabbit/human Fab for cocrystallization of HIV*-1 Rev. J. Mol. Biol. 397, 697-708; Stahl, S. J., et al., (2014) *Generation and use of antibody fragments for structural studies of proteins refractory to crystallization*. Methods Mol Biol 1131, 549-561). Briefly, rabbits homozygous for immunoglobulin allotypes VHa1 and Ckb9 were immunized with purified rHBeAg and spleen and bone marrow were collected and processed for total RNA preparation. RT-PCR amplification of rabbit VL, Ck, and $V_H$ encoding sequences was performed using established primer combinations and protocols. VLCk-$V_H$ cassette assembly and asymmetric SfiI ligation into the phage display vector pC3C was performed as described previously (Hofer, T., et al., (2007) *Chimeric rabbit/human Fab and IgG specific for members of the Nogo-66 receptor family selected for species cross-reactivity with an improved phage display vector*. J Immunol Methods 318:75-87). The library consisting of transformed rabbit/human Fab clones was selected by phage display on rHBeAg which had been selectively biotinylated on the Carboxyl-terminal Avi-tag and immobilized on stepavidin-coated plates. After several rounds of panning, selected clones were screened for rHBeAg binding by ELISA and hits were sequenced.

Expression and Purification of Fab and scFv Antibody Fragments. A modified ompAVk-Ck-pe1B-VH-CH1-polyHis cassette was transferred from pC3C into *E. coli* expression vector pET11a (Novagen) between the NdeI-BamHI restriction sites. The Fab Vk and VH sequences were also cloned into pET11a such that the single-chain variable fragment (scFv) versions of them would be expressed joined by the 18-residue linker (i.e. ompA-Vklinker-VH-polyHis). Similar to Fab, these scFv also had a Carboxyl-terminal polyHis-tag to facilitate purification. The expression plasmids for Fab or scFv production were transfected into *E. coli* strain BL21-CodonPlusRIL (Stratagene) and the resulting transfectants were grown in a 1-L fermenter as previously described (Stahl, S. J., et al., (2010) J. Mol. Biol., supra). Bacterial cultures were clarified by centrifugation at 14,000 g for 1 h. The secreted antibody in the supernatant had a Carboxyl-terminal His-tag and was captured using 75 ml of Ni-Sepharose resin (GE Healthcare) at 4° C. for 1-2 hours, washed with PBS (pH7.4) plus 20 mM imidazole. The Fabs were eluted with PBS plus 0.5 M imidazole and then dialyzed against 25 mM HEPES buffer (pH7.4), 0.15 M NaCl, 0.2 mM TCEP, 10% glycerol. To maintain solubility during purification, 1 M urea was often included in buffers. In these studies, the Carboxylterminal His-tag was not removed.

Kinetics of Antibody Binding Using Surface Plasmon Resonance. All experiments were performed on a Biacore X100 (GE Healthcare) instrument at 25° C. HBS-EP (10 mM HEPES, pH 7.4, 150 mM sodium chloride, 3 mM EDTA, 0.05% Polysorbate 20) was used as the running buffer and data were analyzed using Biacore X100 evaluation software (GE Healthcare). Cell 1 was left untreated to serve as a reference surface and cell 2 was used as the experimental surface. Fabs were diluted (10-20 µg/ml) in 10 mM sodium acetate buffer (pH 4.5-5.0) and immobilized on CM5 sensor chips by the standard amine coupling method (Amine Coupling kit, GE Healthcare) at a flow rate of 5 µl/min. The immobilization levels of the proteins on the sensor chip surfaces were approximately 1500 RU. For kinetic analysis, analytes were prepared by serial dilution with HBS-EP buffer over a range typically 10 nM-1 µM and injected over both the reference and experimental surfaces at a flow rate of 30 µl/min. Sensor chips were regenerated by a 60 s injection of 50 mM sodium hydroxide. Signals from the reference surface and an ensemble of buffer blank injections were subtracted to correct for nonspecific binding and injection artifacts. The corrected results were globally fitted to a 1:1 binding model and the association rate constant (ka), and dissociation rate constant (kd), were used to determine the equilibrium dissociation constant (Kd) in units of M.

Sandwich ELISA Assay. (FIG. 6C) Non-treated 96 well microplates (ThermoFisher) were coated with 100 µl per well of 10 µg/ml of murine monoclonal antibody Mab e6 (Ferns, R. B., and Tedder, R. S. (1984) *Monoclonal antibodies to hepatitis Be antigen (HBeAg) derived from hepatitis B core antigen (HBcAg): their use in characterization and detection of HBeAg*. J. Gen. Virol. 65:899-908) in 0.2 M sodium carbonate buffer, pH 9.4, by incubation either at 37° C. for 1 h or at 4° C., overnight. The plates were then washed with 200 µl/well of PBST (8 mM Na2HPO4, 150 mM KH2PO4, 3 mM KCl, 0.05% Tween 20, pH 7.4) for 5 min, repeated three times, at room temperature with shaking. Plates were blocked with 10% fetal bovine serum/PBS, 300 µl/well, at 37° C. for 1 h, and then washed with PBST as above. Test samples, diluted if necessary with PBS, and positive and negative controls were added, 100 µl/well, and incubated at 37° C. for 1 h. Plates were then washed with PBST as above. Fab e13-HRP, 1 µg/ml in 2% BSA/PBS, was added at 100 µl/well and incubated at 37° C. for 1 h. Plates were then washed with PBST as above. Color was developed with tetramethylbenzidine (TMB) 100 µl/well, incubated at room temp for 5-15 min. The reaction was quenched by addition of 100 µl 2 N $H_2SO_4$ and then absorbance at 450 nm was measured using a Bio-Tek Synergy HT plate reader. Test results were calculated as the signal to cut-off ratio (S/CO).

In the process of assay development, we used goat anti-human IgG-HRP (SeraCareKPL) to detect the chimeric secondary Fab antibody as described below. Also, for blocking we used either 5% BSA in PBS or 10% FBS in PBS although the latter was preferred as it gave cleaner backgrounds.

Fab e13 HRP Conjugation. This was performed using an EZ-link Plus activated peroxidase kit (Thermo) according to the manufacturer's instructions.

Assay Quantification. The intra-assay and inter-assay coefficients of variation (CV) were determined with several different concentrations of HBV-positive patient plasma samples, in triplicate. The procedure was repeated three times independently and each run was performed on different days. The CV was defined as [% CV=STD/average*100] where STD is the standard deviation.

Determination of Cut-off (CO) Value. 25 HBV patient samples, which were determined to be HBeAg-negative with the Ortho-Clinical Vitros Eci immunodiagnostic system in the NIH Clinical Center, were assayed in triplicate using the sandwich ELISA described above. The cut-off value (CO) was defined as [CO=average+(3*STD)].

Indirect ELISA for Screening Crossreactivity. The microtitre plates were coated with 10 µg/ml of rHBeAg, rHBcAg (capsids) or HBsAg, then washed and blocked as described above. Negative controls were healthy patient plasmas. Fabs were added 100 µl (2 µg/ml) and incubated at 37° C. for 1 h followed by washing. Bound antibody was detected using 100 µl anti-human IgG-HRP (KPL, Inc.) diluted 1/5000 with 2% BSA in PBS. Following incubation for 1 h in the dark at 37° C. and then washing, the color was developed with TMB as described above. The HBeAg reference preparation was obtained from the Paul-Ehrlich-Institut (Langen, Germany, code 129097/12). This is HBVpositive patient plasma and is used as an international standard. The preparation has a defined HBeAg activity of 100 PE IU/mL. Two Hepatitis B Seroconversion panels (catalog Nos. 6278, 6282) were obtained from ZeptoMetrix.

Immunoaffinity Purification of HBeAg from HBV Patient Plasma. Mab e6 was linked to AminoLink resin (ThermoFisher) by amine coupling according to the manufacturer's instructions. HBV patient plasmas (approx. 1 ml) were incubated with Mab e6 resin at 4° C. overnight and then washed 3 times with PBST. Protein was eluted from the resin either using glycine buffer, pH 3.0, or by boiling in SDS PAGE loading buffer. The samples were separated on a 4-12% SDS-PAGE gel and gel slices were analyzed for HBeAg by Taplin Mass Spectrometry Facility at Harvard Medical School.

Western Blotting. Samples were separated on a 4-12% SDS-PAGE gel and electrotransferred to a PVDF membrane (Invitrogen). After blocking with 5% nonfat milk solution for 1 h, the membrane was incubated with antirHBcAg polyclonal antibody (Dako, B0586) to recognize HBeAg in the samples. After washing, the membrane was further incubated with peroxidase-conjugated anti-rabbit IgG (KPL). Signals were then detected with a chemiluminescence reagent (ThermoFisher) and exposure on X-ray film.

Preparation of Immune Complexes for Structural Studies. A two-fold or greater molar excess of Fab or scFv was mixed with rHBeAg and the mixture was then applied to a Superdex S200 column. The column fractions were monitored by SDS-PAGE and the immune complex identified (usually the main peak). This was used for characterization and for crystallization screening. Alternatively, immune complexes were applied to a NiSepharose 6 Fast Flow column and processed as previously described (Stahl, S. J., et al., (2014) *Generation and use of antibody fragments for structural studies of proteins refractory to crystallization.* Methods Mol Biol. 1131:549-561).

Analytical Ultracentrifugation. A Beckman Optima XL-I analytical ultracentrifuge, absorption optics, an An-60 Ti rotor and standard double-sector centerpiece cells were used. Equilibrium measurements were made at 20° C. at 11,500 rpm for Fab complexes and 14,500 rpm for scFv complexes. The ternary complex of rHBeAg, scFv me6 and Fab e13 was measured at 10,000 rpm. Concentration profiles were recorded every 4 h for 16 h and then baselines were established by over-speeding at 45,000 rpm for 3 h. Data (the average of 8-10 scans collected using a radial step size of 0.001 cm) were analyzed using the standard Optima XL-I data analysis software.

Protein partial specific volumes (v-bar), calculated from the amino acid compositions, and solvent densities were estimated using the program SEDNTERP (rasmb.bbri.org). Sedimentation velocity measurements at 20° C. were made at 40,000 rpm with data collection every 5 min to 3 hours.

Example 1

Panel of rHBeAg-Specific Fab

The Fab CDR sequences of a panel of 24 clones are shown in Table 1. Included in Table 1, for comparison, are the murine/human Fab me6 derived from the murine Mab e6, which binds rHBeAg with high specificity (Watts, N. R., et al., (2010) J. Mol. Biol., supra), and chimeric rabbit/human Fab Rev, which binds to the HIV-1 Rev protein with pM affinity (Stahl, S. J., et al., (2010), J. Mol. Biol. supra). We selected 17 of the clones from Table 1 for further analysis based on their sequence diversity. The chimeric rabbit/human Fabs were expressed in *E. coli* using the expression cassette pC3C which comprised: ompA-Vk-CkpelB-VH-CH1-polyHis where the ompA and pelB leader sequences direct secretion of the L and H chains into the periplasm. The Carboxyl terminal His-tag on the heavy chain enables protein purification by immobilized meta-laffinity chromatography on Ni+2-nitrolotriacetic acid agarose. Usually this one step of purification was adequate but for structural studies an additional gel filtration step was included. With Western blot analysis, none of the Fab panel detected rHBeAg following SDS PAGE, indicating that they were directed against conformational epitopes.

Example 2

Characterization of Chimeric Fab Antibodies
ELISA Screening

The characterization of the Fab panel had two initial goals: first, to assess affinity against the rHBeAg standard; and second, to check specificity, primarily against the closely related rHBcAg (FIG. 1C) but also against HBsAg which is often present together with HBeAg in clinical samples. For initial screening, we used an indirect ELISA microtitre plate assay where rHBeAg was coated by adsorption onto the plate and the chimeric rabbit/human Fab binding was detected using HRP-labeled human IgG. The strongest responses were from Fabs e1, e8, e13, e21 and e38 (FIG. 2). The Fab panel was then assayed with plates coated with either rHBcAg (capsids) or HBsAg. As expected, the panel only presented background level binding to HBsAg. In contrast, many Fabs displayed above background binding to rHBcAg, especially Fabs e1, e5, e8, e13, e21, e29, e38 (FIG. 2). Typically, Fab binding to rHBeAg was higher than to rHBcAg except Fabs e5, e16 and e30, which all gave low responses to either antigen. From this basic survey, Fabs e13, e21 and e38 gave the highest response to rHBeAg and with the lowest cross reactivity to rHBcAg. To put the specificity of these selected Fabs in context, we can compare with the murine/human chimeric Fab me6, which does not bind to rHBcAg (capsids). For example, with Fabs e13 and e38, which are the strongest rHBeAg binders, the ratios of binding to rHBeAg versus rHBcAg (capsids) were both approx. 2.5, compared to 4.5 obtained with the Fab me6. In general, when antigens are adsorbed onto a plate, some protein denaturation can occur which may change the presentation of epitopes, potentially decreasing or increasing antibody binding.

Example 3

Binding Kinetics Studied by SPR

The binding characteristics of the Fabs which appeared to be the strongest binders to rHBeAg in the ELISA assay were next examined in more detail using the Biacore system, which detects binding by surface plasmon resonance (SPR). Fab was immobilized on the chip (ligand) and titrated with antigen (analyte). The dissociation constants (kd) are given in Table 2.

TABLE 2

Binding of rHBeAg and rHBcAg to chimeric Fab as measured by SPR Fabs (ligands) were immobilized on the Biacore chip. The recombinant dimeric antigens (analytes) were titrated over at least a 100-fold concentration range and the indicated kinetic constants were determined. Statistics associated with these measurements are provided in Table S1. To determine their stoichiometry, the immune complexes of Fab and either dimeric rHBeAg or dimeric rHBcAg were resolved by gel filtration and the masses determined by analytical ultracentrifugation (nd: not determined).

| Ligand Fab | Analyte | $k_a$ ($M^{-1}s^{-1}$) | $k_d$ ($s^{-1}$) | $K_d$ (M) | Stoichiometry Fab:rHBAg |
|---|---|---|---|---|---|
| e1 | rHBeAg | $9.01 \times 10^3$ | $3.61 \times 10^{-5}$ | $4.01 \times 10^{-9}$ | 2:2 |
|  | rHBcAg | $1.62 \times 10^3$ | $1.37 \times 10^{-4}$ | $8.43 \times 10^{-7}$ | nd |
| e8 | rHBeAg | $6.8 \times 10^3$ | $8.2 \times 10^{-4}$ | $1.22 \times 10^{-7}$ | 1:2 |
|  | rHBcAg | — | — | $>10^{-5}$ | nd |
| e13 | rHBeAg | $8.50 \times 10^3$ | $2.61 \times 10^{-7}$ | $3.07 \times 10^{-11}$ | 2:2 |
|  | rHBcAg | $2.31 \times 10^4$ | $2.09 \times 10^{-3}$ | $9.05 \times 10^{-8}$ | nd |
| e21 | rHBeAg | $1.60 \times 10^3$ | $1.78 \times 10^{-4}$ | $1.11 \times 10^{-10}$ | 1:2 |
|  | rHBcAg | $2.70 \times 10^2$ | $5.73 \times 10^{-5}$ | $2.12 \times 10^{-7}$ | nd |
| e38 | rHBeAg | $8.18 \times 10^3$ | $7.19 \times 10^{-8}$ | $8.79 \times 10^{-12}$ | 2:2 |
|  | rHBcAg | $3.67 \times 10^3$ | $1.10 \times 10^{-4}$ | $2.99 \times 10^{-8}$ | nd |
| me6 | rHBeAg | $1.6 \times 10^4$ | $1.6 \times 10^{-4}$ | $1.08 \times 10^{-8}$ | 2:2 |
|  | rHBcAg | 0 | 0 | 0 | No binding |

Binding affinities to the rHBeAg ranged from Kd approx. $10^{-7}$-$10^{-12}$M and were ranked (high to low affinity): Fab e38>e13>e21>e1>e8, which closely matches the ELISA data (FIG. 2). The tightest binders (Fab e13 and Fab e38) exhibited very low dissociation rates, which is a characteristic of high-affinity binding. However, we note that with such low off-rates, and with the technical limitations of the method, there is some uncertainty about the actual kd values but there is no doubt that they exhibit the high affinities typical of antibodies selected from rabbit immune repertoires by phage display.

Binding of Fabs to rHBcAg capsids was generally lower, ranging from Kd approx. $10^{-5}$-$10^{-8}$M and were ranked: Fab e38, e13>e1, e21>e8, which again is similar to the ELISA data (FIG. 2). With, for example, Fab e38 and Fab e13, the off-rates are approximately four orders of magnitude higher compared to their binding to rHBeAg. Therefore, although binding to rHBeAg is not absolutely specific it is significantly stronger than to rHBcAg capsid. The murine/human chimeric Fab me6 exhibited no binding to rHBcAg capsid (Table 2). This confirms our previous finding with the murine Mab e6 (Watts, N. R., (2010) J. Mol. Biol., supra). To generate chimeric Fab me6 we sequenced Mab e6 and used this for gene synthesis and *E. coli* expression. The SPR data clearly shows that specificity was retained and this was also true for the scFv e6.

Example 4

Binding Stoichiometry

Figure 3:
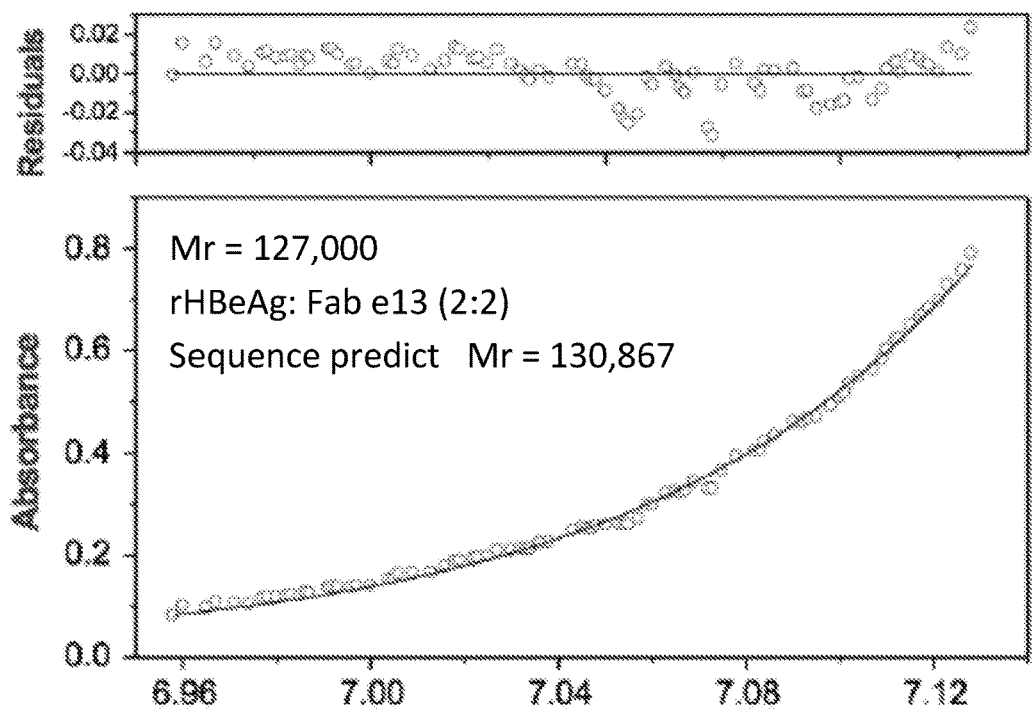
FIG. 3 shows the sedimentation equilibrium of rHBeAg—Fab e13 complex. The panels show absorbance (bottom panel) and residuals (upper panel). Open circles show the UV absorbance gradient in the centrifuge cell. The solid line indicates the calculated fit for an ideal single species. Residuals show the difference between the fitted and experimental values as a function of radial position. The determined molecular weight 127,000 (±1500) is indicated and this compares with a molecular weight of 130,867 calculated for a complex of 2 Fab e13 and one rHBeAg dimer.

As the rHBeAg is a homodimer, in principle it has two copies of most epitopes. This was studied by mixing rHBeAg with a two-fold molar excess of Fab and resolving complexes from excess reagents by gel filtration and then analyzing by analytical ultracentrifugation. The sedimentation equilibrium profile, for example, from Fab e13 (FIG. 3) was used to determine a mass of 127 kDa, which is close to that predicted for a complex of 2 Fab and one rHBeAg dimer (131 kDa). The 2:2 binding stoichiometry was also observed with Fabs e38, e1 and Fab me6. For Fabs e8 and e21, 1:2 binding was observed indicating that only one Fab bound to dimeric rHBeAg (Table 2).

Example 5

Development of a New and Specific HBeAg Assay

Figure 4:
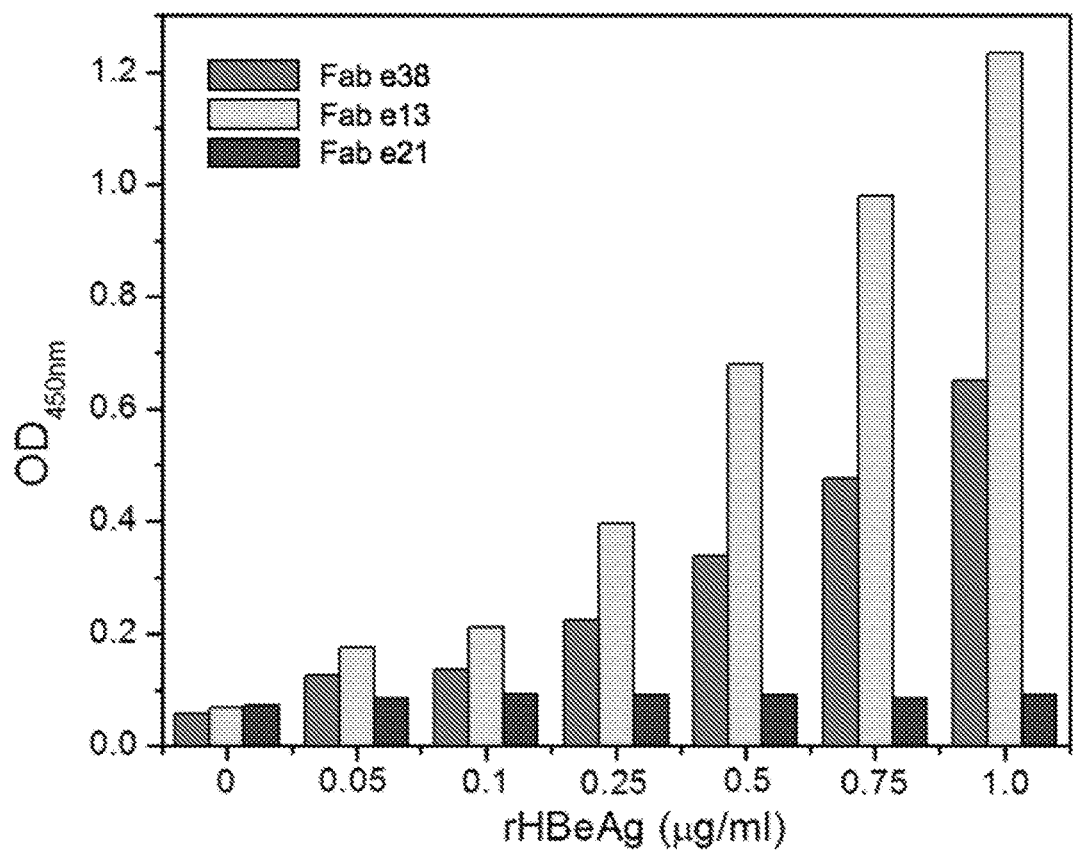
FIG. 4 shows secondary antibody pairing. A sandwich ELISA was used which incorporated Mab e6-coated plates for antigen capture, and Fabs e13, e21 or e38 for detection. Anti-human IgGHRP was used to generate the absorbance signal at 450 nm. The assay was performed over the range of 0-1 µg/ml rHBeAg. The experiment was performed three times, with similar results.

One of the aims of this study was to apply the high-affinity Fabs to the development of a specific and quantitative assay for the HBeAg. We used the traditional ELISA sandwich format for the formulation of this assay. Based on its specificity for the rHBeAg, we used the murine monoclonal antibody Mab e6 (IgG2a) for antigen capture even though it does not have the highest binding affinity (Table 2). We found in initial screening trials that microtiter plates coated with Mab e6 gave more reliable results than the chimeric Fab me6, suggesting that more correctly orientated binding sites are presented with the larger adsorbed molecule. For detection, we screened the highest affinity binders identified in Table 2, namely, Fabs e38, e21 and e13, and used HRP-coupled antihuman IgG for detection. Over the rHBeAg concentration range 0-1 µg/ml, Fab e13 gave the strongest response and Fab e21, which binds rHBeAg with 1:2 stoichiometry, gave only a weak signal (FIG. 4). Based on these results, the pairing of Mab e6 and Fab e13 for capture and detection, respectively, of HBeAg was further developed.

Example 6

Epitope Mapping

Figure 5A:
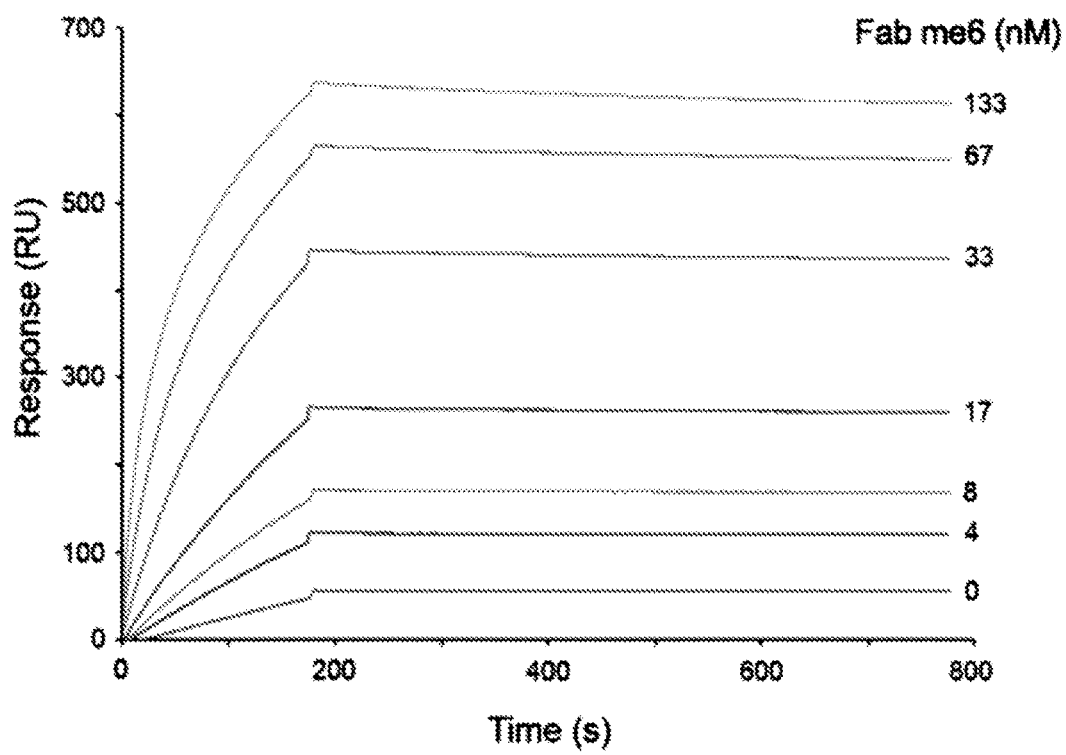
FIGS. 5A and 5B show the results of epitope mapping using surface plasmon resonance.
Figure 5B:
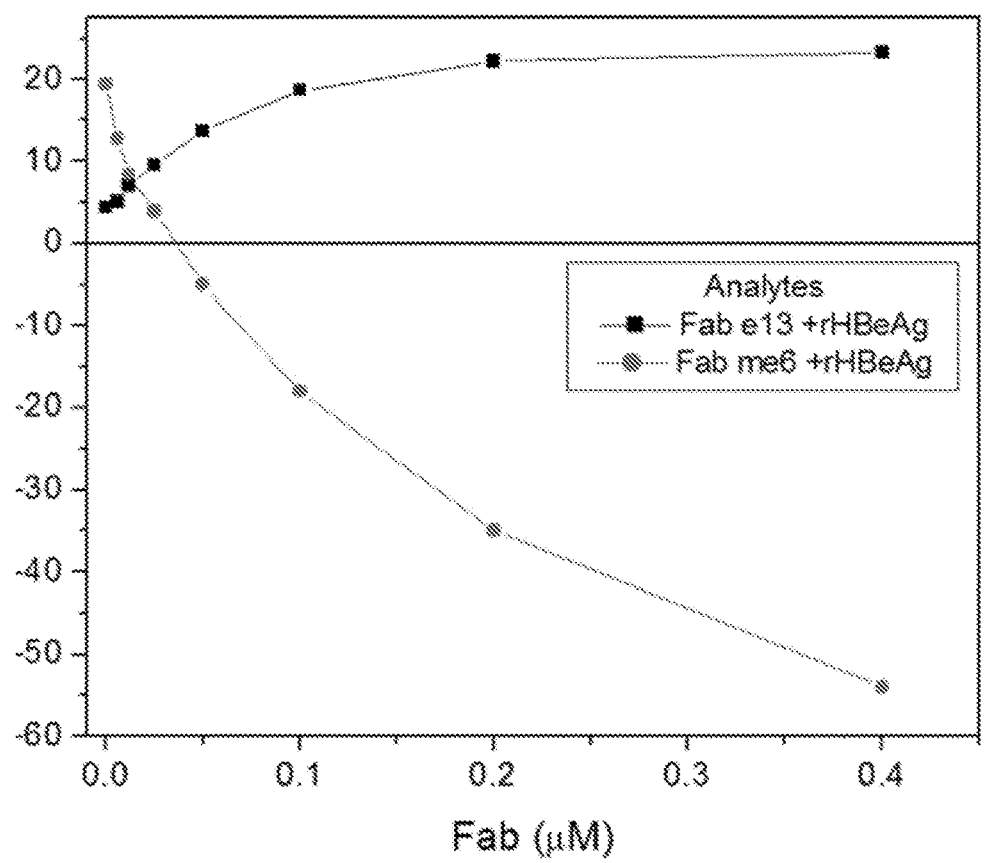

In a sandwich ELISA, the capture and detection antibodies should ideally have different, non-overlapping epitopes. Although this requirement is not essential for antibodies which can bind to both epitopes of a dimeric protein, we sought to combine specific capture with high affinity detection and, as rationalized above, the combination of Mab e6 and Fab e13 was the combination of choice. The cross-reactivity of these two antibodies was studied by rHBeAg neutralization as monitored by SPR. First, immobilized Fab e13 was titrated with a fixed amount of rHBeAg together with increasing concentrations of Mab e6. There was a positive non-competitive response proportional to Mab e6 concentration (FIG. 5A). Namely, rHBeAg with bound Mab e6 could still bind to the Fab e13 ligand. Second, immobilized Mab e6 was titrated with a fixed amount of rHBeAg together with varying concentrations of either Fab e13 or Fab me6: non-competitive and competitive bindings, respectively, were observed (FIG. 5B). These results indicate that Mab e6 and Mab e13 bind to rHBeAg, and presumably HBeAg, at non-overlapping epitopes.

Example 7

Calibration Curves

Figure 6A:
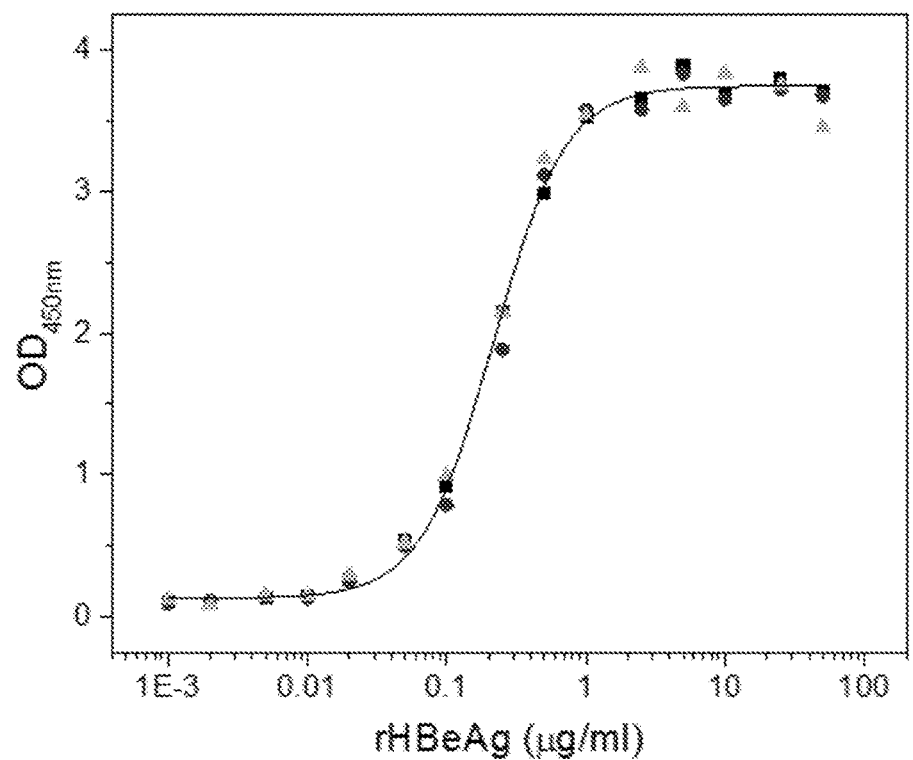
FIG. 6A shows an ELISA response curve with rHBeAg. With the optimized sandwich ELISA protocol, rHBeAg is titrated over the concentration range: 0-100 µg/ml (0-5.6 The experiment was performed in triplicate, and a sigmoidal fit to the data is shown with an $EC_{50}$ approx 12 nM.
Figure 6B:
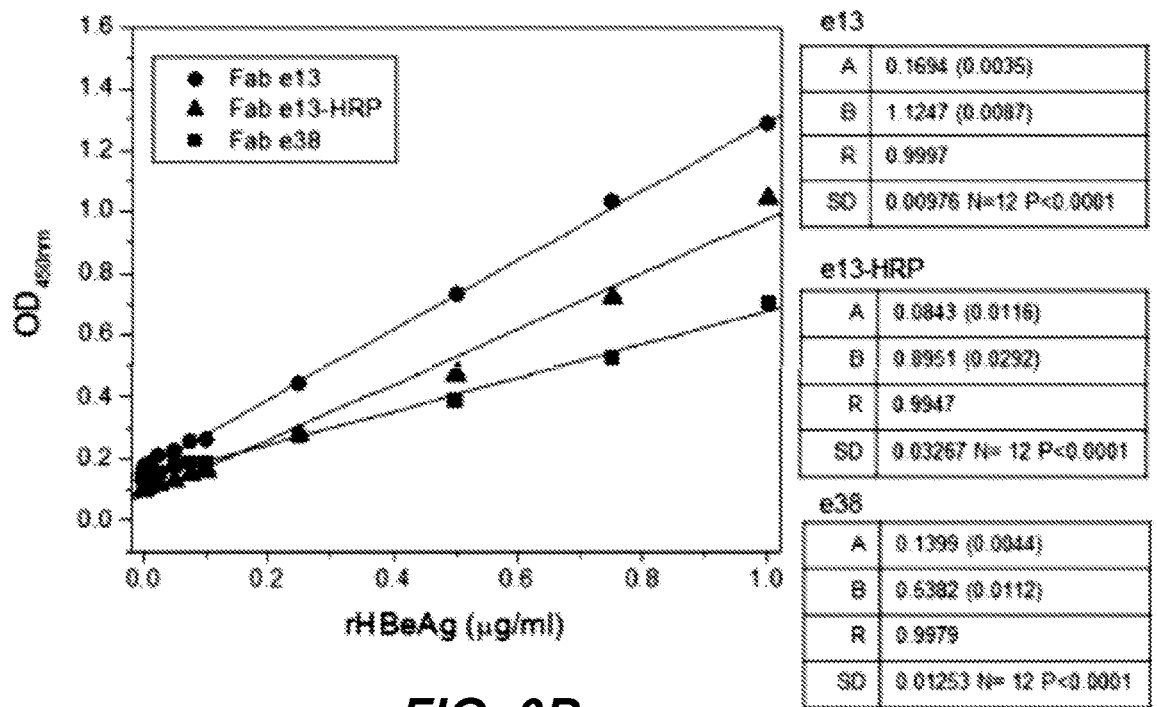
FIG. 6B shows calibration curves for Fab e13: conjugated and non-conjugated with HRP. ELISA sandwich assay of rHBeAg using Mab e6 for antigen capture and unconjugated Fabs e13 and e38 for detection. Anti-human IgG-HRP was used to generate signal at 450 nm. These are compared with the Fab e13 directly conjugated to HRP. The experiment was performed twice, with triplicate measurements each time. The averages were plotted and the corresponding linear fits are shown on the right.

A sandwich ELISA which incorporated Mab e6 for antigen capture, Fab e13 for detection and HRP-anti-human IgG for signal generation, was used to titrate rHBeAg over the range of 0-100 µg/ml (FIG. 6A). The absorbance response was linear from 0.1-1 µg/ml and at >50 µg/ml the "hook effect" was observed indicating saturation. To simplify the assay, rather than using secondary antibody detection, HRP was conjugated to Fab e13. Over the linear response range (0.1-1 µg/ml), the conjugate gave only a slightly lower response than the nonconjugated antibody, therefore it was adopted for all subsequent studies (FIG. 6B). Following further optimization, including, for example, antibody concentrations, selection of blocking reagents and incubation times, the ELISA protocol was established as depicted in the schematic of FIG. 6C.

Figure 6D:
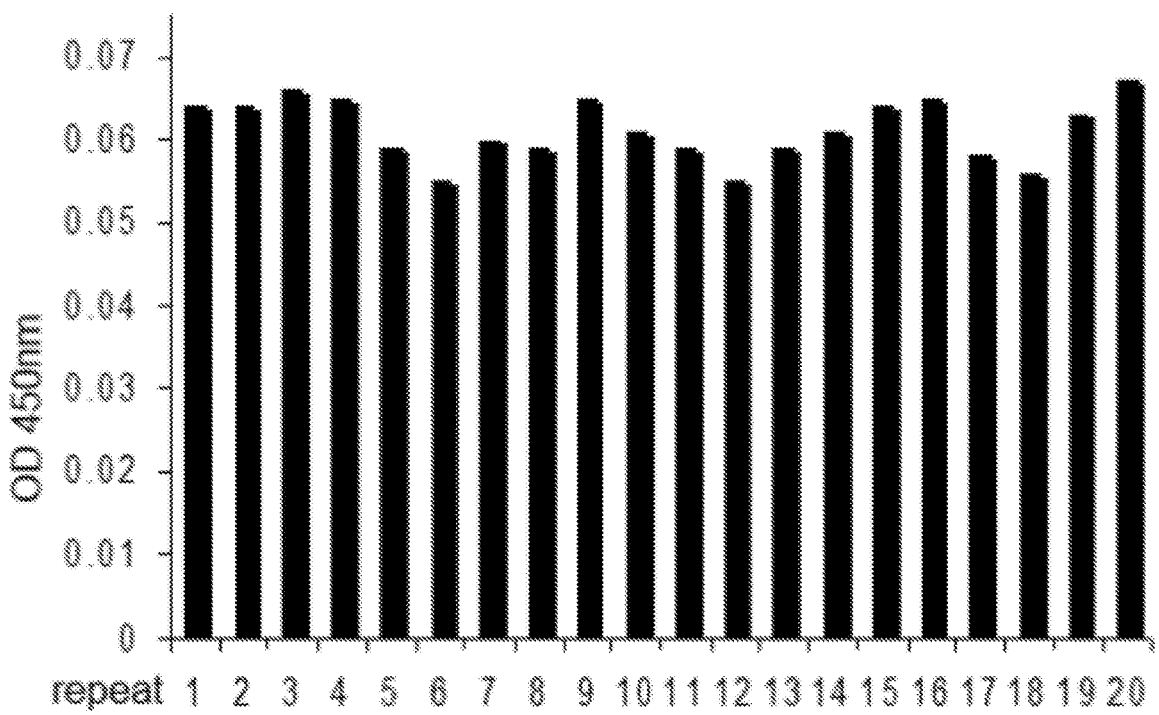
FIGS. 6D-6F show the results of the ELISA assay: determination of cut-off value; intra- and inter-plate variation; and matrix effect.
Figure 6C:
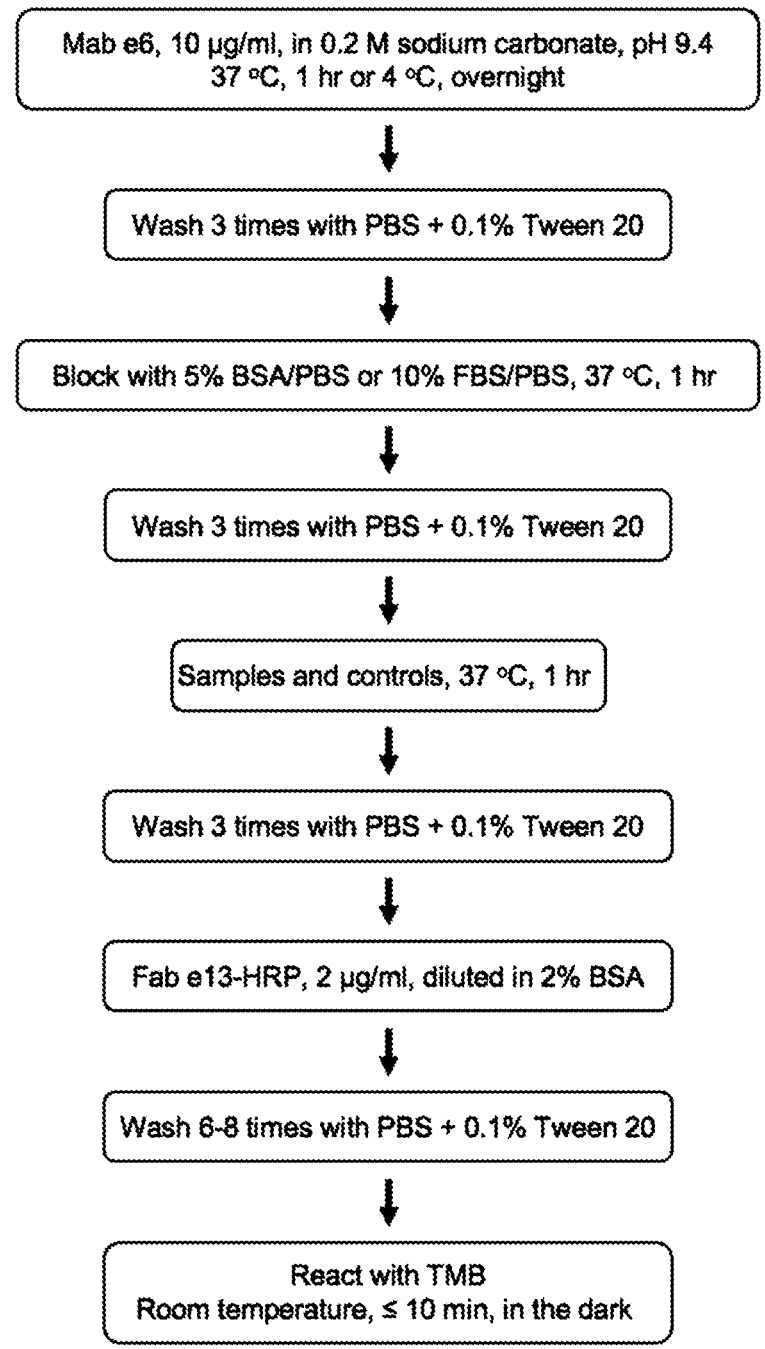
FIG. 6C shows a sandwich ELISA protocol flow sheet for the detection and assay of HBeAg.
Figure 6E:
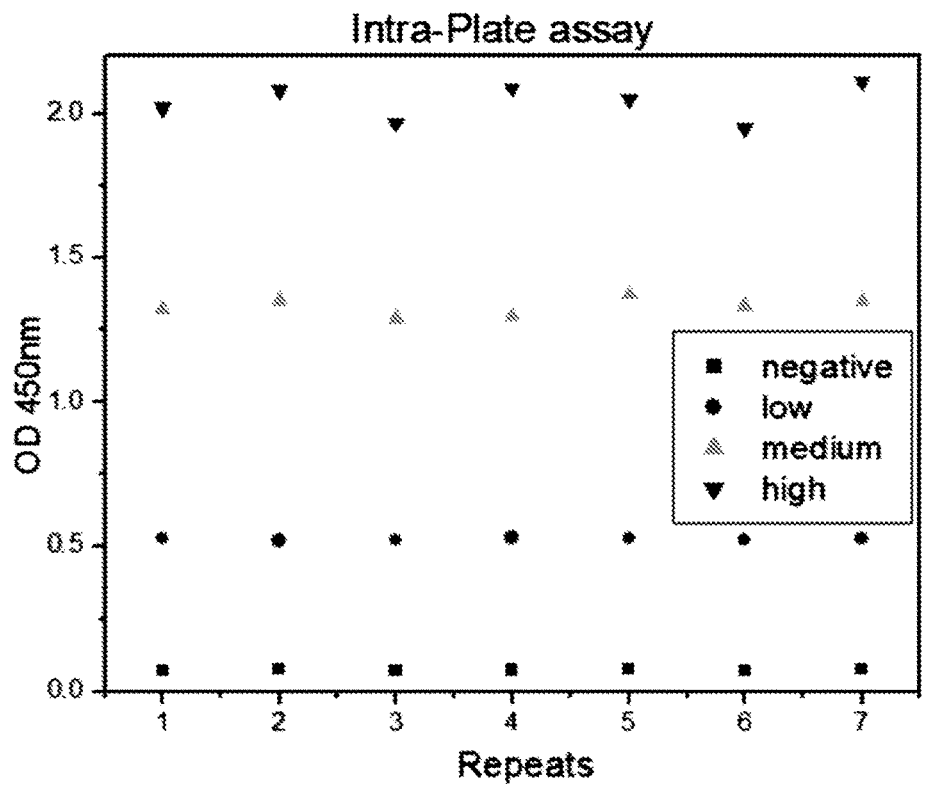
Figure 6F:
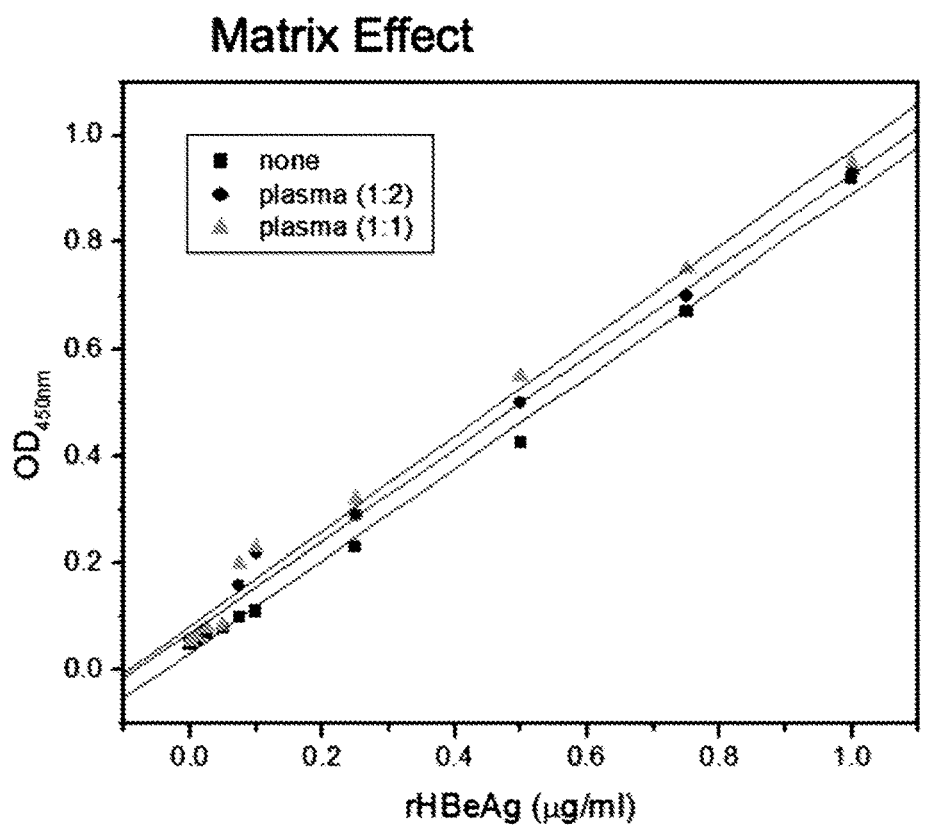

For standardization of the calibration curves we determined a cut-off value (CO) for the assay and as illustrated in FIG. 6D. We also checked intra- and inter-plate variation using samples with negative, low, medium and high signals (FIG. 6E). The intra- and inter-assay coefficient of variance (CV) values were <5% and <7.2%, respectively, which indicated high reproducibility (FIG. 6F). The values compiled in Table 3 are consistent with good assay performance.

TABLE 3

Compilation of ELISA assay values: determination of cut-off value; intra- and inter-plate variation (precision), and matrix effect.

| Sample (OD$_{450}$) | Intra-assay CV (%) | Inter-assay CV (%) |
|---|---|---|
| Negative (<0.1) | 2.49 | 5.40 |
| Low(0.1-1) | 1.76 | 5.51 |
| Medium (1-2) | 2.17 | 5.15 |
| High(>2) | 3.00 | 7.20 |
| Mean | 2.355 | 5.815 |

Figure 6G:
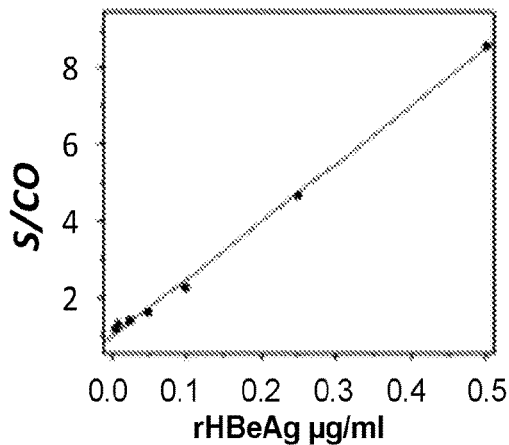
FIGS. 6G-6I show calibration of rHBeAg and WHO PE standard.
Figure 6H:
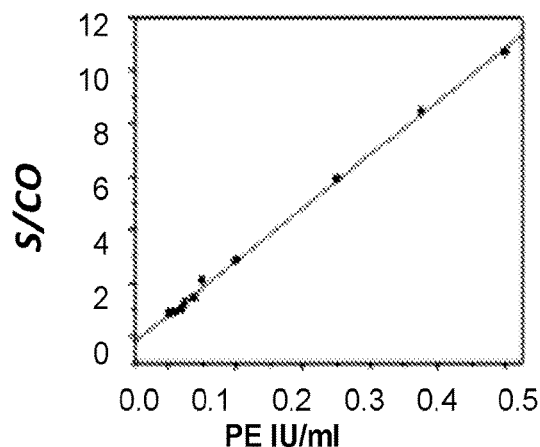
Figure 6I:
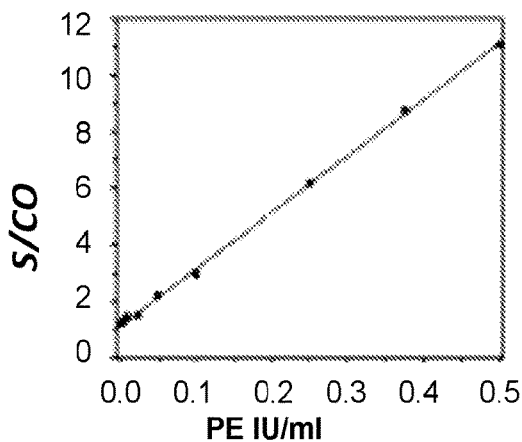
Figure 6J:
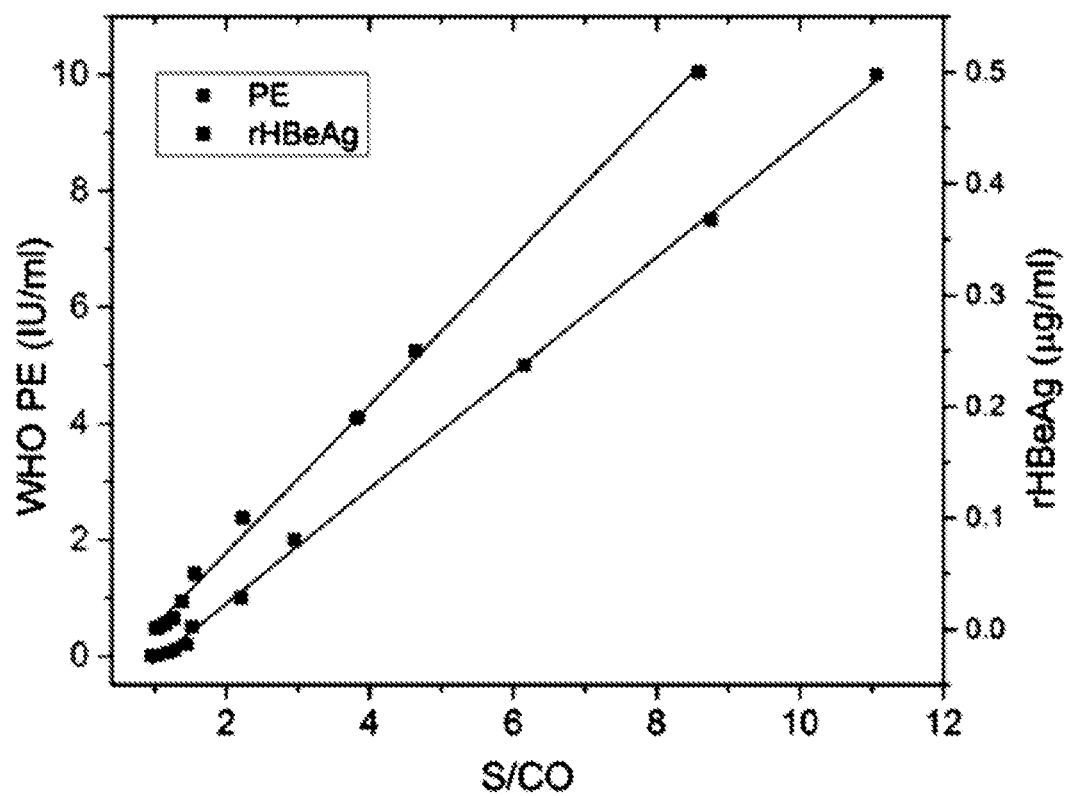
FIG. 6J shows the calibration curves for rHBeAg and WHO standard. Using the sandwich ELISA (FIG. 6C), calibration curves for the HBeAg WHO reference sample from the Paul-Ehrlich-Institut (PE IU/ml) and rHBeAg were prepared where the signal to cut-off (S/CO) ratio was determined as described in in the Examples section of this disclosure. From the plots, 1 PE IU/ml corresponds to approx. 0.05 µg/ml (2.8 nM) rHBeAg. The experiment was performed in triplicate.

Using rHBeAg, calibration curves of signal to cut-off ratio (S/CO) (FIG. 6G) indicated a linear response up to 1 µg/ml (56 nM, monomer) with a lower detection limit of approx. 4 ng/ml (0.2 nM). A calibration curve was also prepared using the WHO HBeAg international standard from the Paul-Ehrich-Institut which has an activity of 100 PE IU/ml. The linear plots for 0-1.0 PE IU/ml and 0-10 PE IU/ml are shown in FIGS. 6I1 and 6I, respectively. The lower detection level is approx 0.02 PE IU/ml. From these plots, 1 PE IU/ml corresponds to approx. 0.2 µg/ml (approx. 10 nM) of the rHBeAg (FIG. 6J).

Example 8

Assay Clinical Performance

Figure 7:
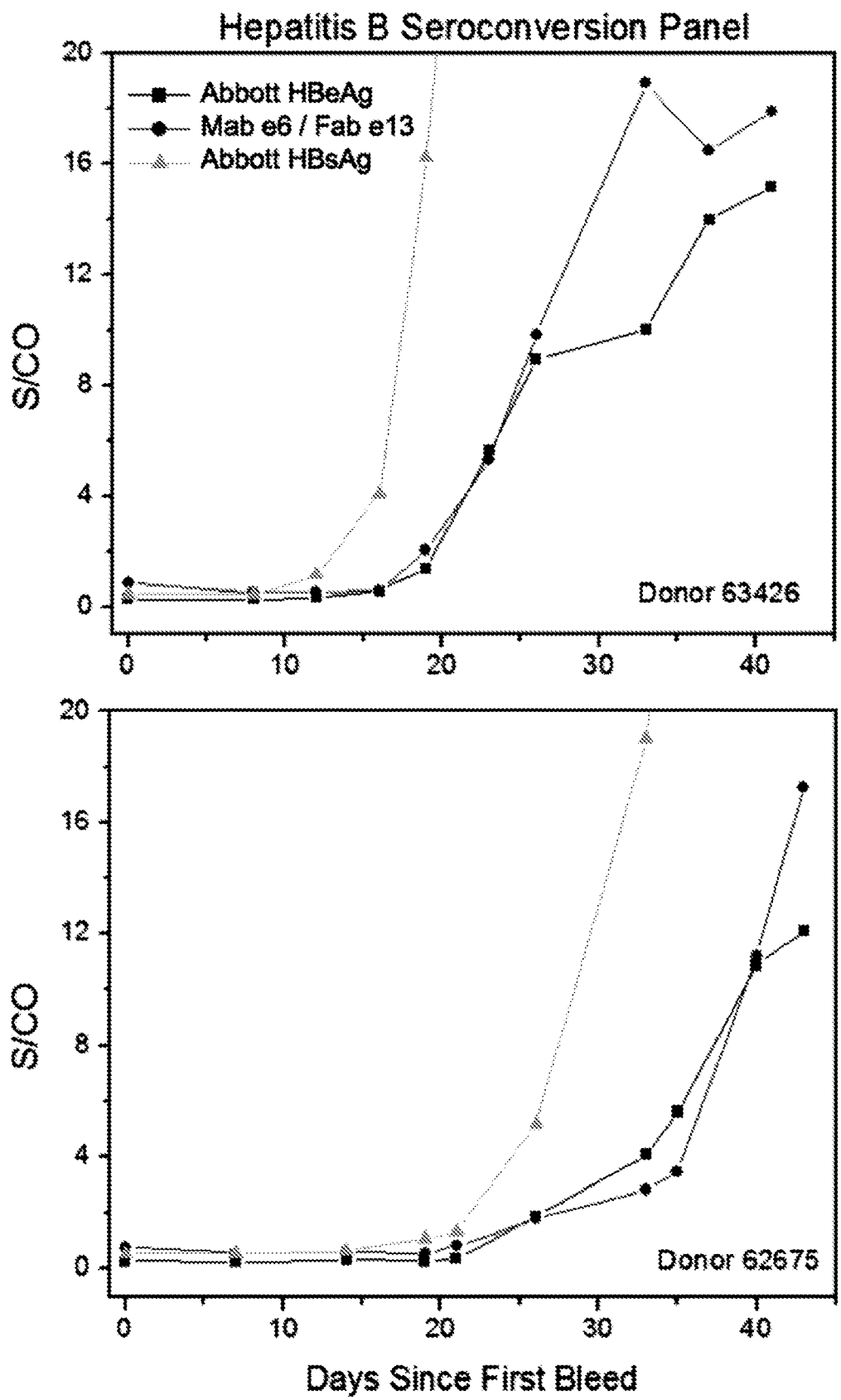
FIG. 7 shows the detection of HBeAg in commercial seroconversion panels. The commercial seroconversion panels from two HBV patients (donor numbers are indicated at the bottom of each panel) included assay data obtained using Abbott systems for the HBsAg and HBeAg. These data are plotted together with assay data from the Mab e6/Fab e13 ELISA.

To test the utility of the assay on patient samples, we first checked the matrix effect by titrating rHBeAg to 1 µg/ml in the presence of undiluted and 1:1 diluted non-immune human plasma. No differences were observed in the linear plots. Our next check of the assay was to detect HBeAg content in patient plasma using a negative-to-positive seroconversion panel. Two commercial panels from ZeptoMetrix were used which also included assay data for HBsAg and HBeAg determined using the Abbott Laboratory assay systems. There was a high correlation between our assay and the Abbott assay in detecting (or not) patient plasma HBeAg (FIG. 7).

The 67 HBV patient plasma samples previously assayed for HBeAg by the NIH Clinical Center were assayed again with two commercial kits and with the system described above. A comparison of a subset of the data (25 samples) is shown in Table 4.

TABLE 4

Screening patient plasma: comparison with commercial systems. A total of 67 HBV patient plasma samples, 35 HBeAg-positive and 32 HBeAg-negative, were tested for HBeAg with the NIH Ortho-Clinical Vitros Eci immunodiagnostic system, with two commercial HBeAg-detection kits (one shown), and the Mab e6/Fab e13 system. Signal to cut-off ratios (S/CO) were calculated as described in Examples section of this disclosure. HBeAg-positive (S/CO > 1); HBeAg-negative (S/CO < 1). A subset (25/67) of the data is shown.

| Patient Sample | Vitros S/CO | Kit-1 S/CO | Mab e6/Fab e13 S/CO |
|---|---|---|---|
| 01 | 0.14 | 0.45 | 0.62 |
| 02 | 0.15 | 0.46 | 0.63 |
| 03 | 0.16 | 0.47 | 0.52 |
| 04 | 0.13 | 0.47 | 0.75 |
| 05 | 0.13 | 0.45 | 0.42 |
| 06 | 0.16 | 0.45 | 0.84 |
| 11 | 1.03 | 0.49 | 1.01 |
| 12 | 1.31 | 0.50 | 0.97 |
| 13 | 1.52 | 0.49 | 1.02 |
| 14 | 1.94 | 0.50 | 1.18 |
| 07 | 2.67 | 0.91 | 1.30 |
| 15 | 3.86 | 1.05 | 1.50 |
| 16 | 11.7 | 4.64 | 2.38 |
| 08 | 33.5 | 3.05 | 1.55 |
| 17 | 148 | 10.44 | 13.77 |
| 18 | 1080 | 25.24 | 37.20 |
| 19 | 1410 | 31.95 | 34.40 |
| 09 | 1660 | 29.85 | 26.44 |
| 20 | 1760 | 31.52 | 37.76 |
| 21 | 1770 | 32.79 | 33.61 |
| 22 | 1820 | 32.67 | 28.81 |
| 10 | 2290 | 29.15 | 22.49 |
| 23 | 2600 | 29.71 | 19.96 |
| 24 | 2630 | 24.45 | 38.60 |
| 25 | 2840 | 23.43 | 28.00 |

The data shows that the detection of positive samples is similar with all three systems. The Vitros system had the strongest signal as it employs chemiluminescent detection rather than the chromogenic detection used in the other two.

The assay data described above indicate that our assay matches the commercial systems in terms of the simple detection of HBeAg in plasma; however, our system appears superior in the following ways: First, our system is more sensitive based on detection limits using both the WHO PE standard and the rHBeAg, shown in Table 5.

TABLE 5

Indicates detection limits of two commercial systems and the Mab e6/Fab e13 ELISA. The assay with the Vitros system was performed by the NIH Clinical Center. A third commercial system (not shown) detected the WHO standard at 0.5 PE IU/ml and rHBeAg at 0.005 µg/ml.

| Antigen | Kit 1 | Vitros | Mab e6/Fab e13 |
|---|---|---|---|
| WHO PE IU/ml | 1 | 0.1 | 0.02 |
| rHBeAg (µg/ml) | 0.01 | 0.001 | 0.001 |

Figure 8:
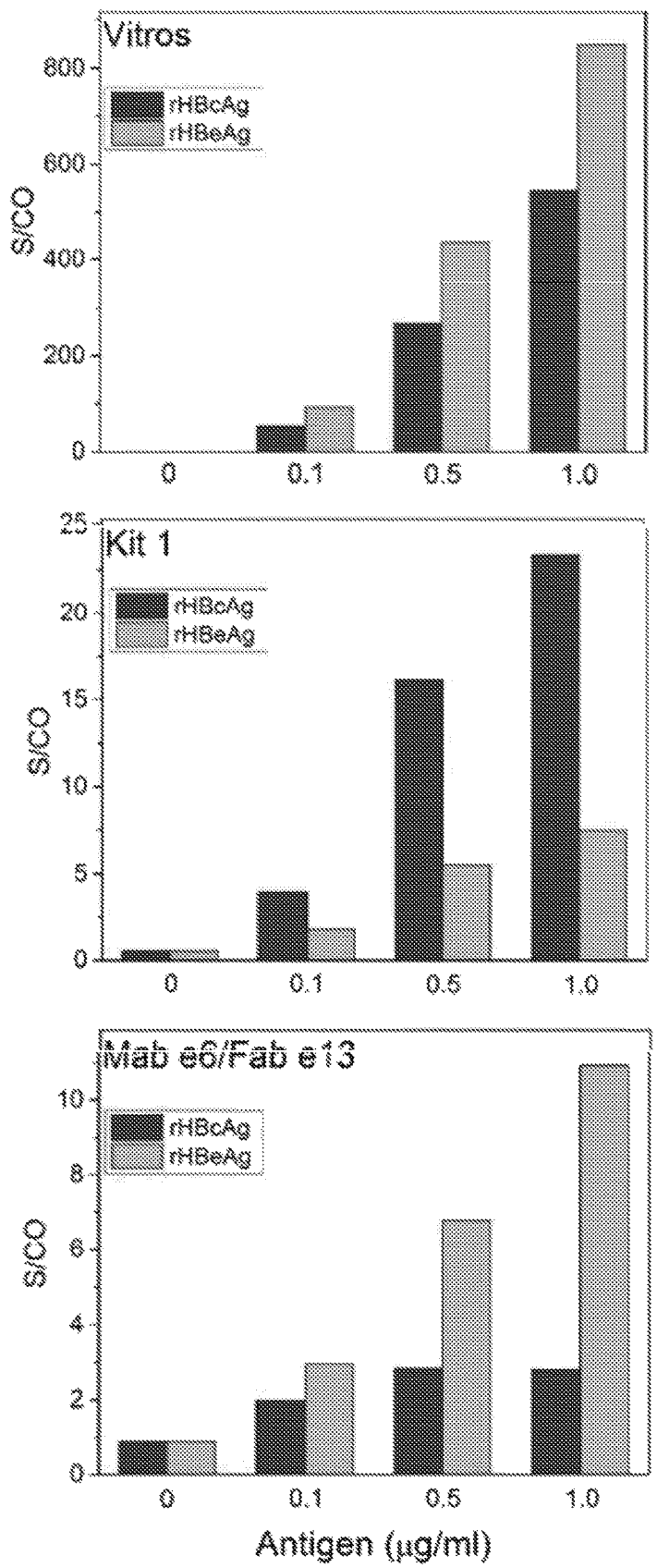
FIG. 8 shows the detection limits of assay and cross reactivity: comparison with commercial systems. The data compares the assay responses to rHBeAg and rHBcAg, i.e., cross-reactivity. Experiments in this FIG. involving Kit 1 and the Vitros system were performed twice and the average values are shown; the in-house system was characterized more extensively in the course of this study.

Second, our assay, based on capture with Mab e6, is more selective for rHBeAg than rHBcAg (capsids), and therefore presumably HBeAg and HBcAg. It might be assumed that commercial systems would be highly specific for the target antigen but two of the systems that we tested showed high cross reactivity with rHBcAg (capsids) (FIG. 8). For the testing of clinical plasma this is not critical as HBcAg (i.e. free nucleocapsid) is usually not present but for basic research purposes this may be of importance. Third, our system is quantitative and we have shown calibration curves for the rHBeAg and the WHO PE standard (FIGS. 6G-6J). The quantitative aspect of our assay should be useful for monitoring the treatment of CHB and for basic research.

Example 9

Identification of HBeAg in Patient Plasma

Another aim of this study was to isolate HBeAg from patient plasma to confirm its sequence, especially at the Carboxyl-terminal end. The antigen was isolated from HBeAg-positive plasma samples (S/CO approx. 1000-3000; approx. 1-3 µg/ml HBeAg) by affinity chromatography using Mab e6 immobilized on resin. SDS PAGE of the eluted protein under reducing and non-reducing conditions followed by Western blot analysis showed a approx. 19 kDa species that migrated slightly faster under the non-reducing condition (FIGS. 9A and 9B), consistent with the presence of an intra-molecular disulfide bond, as occurs in rHBeAg between C(−7) and C61. The protein bands were digested with trypsin, analyzed by mass spectrometry, and the peptides compared to a database of peptides derived from rHBeAg and rHBcAg where full coverage had been established. Three peptides were identified, corresponding to residues 28-40, 82-98, and 127-151 (of SEQ ID NO:2). The 127-151 peptide corresponds to the Carboxyl-terminal sequence of the rHBeAg plus an additional two arginine residues. This result was obtained with HBV genotypes C (two independent determinations) and F. This peptide was not detected in the E genotype.

These Examples demonstrate the inventors' production of a panel of chimeric rabbit/human Fabs specific for rHBeAg, some with unprecedentedly high affinities (Kd of approx. $10^{-12}$ M), that have both diagnostic and therapeutic potential to treat infectious Hepatitis B virus or to prevent reactivation of virus in chronic HBV infected individuals, or to prevent or slow the progress of chronic HBV infection to cirrhosis and/or HCC. The inventors have also described a quantitative assay for HBeAg in which both the epitopes and paratopes are known, and which is superior to existing commercial assays, both in sensitivity and specificity, as the specificities of commercially available antibodies and assay systems against HBcAg and HBeAg are usually either not clearly defined or not known.

The foregoing disclosure is sufficient to enable one skilled in the art to practice the invention. The present invention is not to be limited in scope by the constructs described, because the described embodiments are intended as illustrations of certain aspects of the invention and any constructs that are functionally equivalent are within the scope of this invention.

What is claimed is:

1. An Hepatitis B Virus (HBV) e-antigen (HBeAg) antibody or antigen-binding fragment thereof, wherein the HBeAg antibody or antigen-binding fragment thereof binds to an antigen comprising SEQ ID NO: 2, and wherein the HBeAg antibody or antigen-binding fragment thereof comprises light chain complementary determining regions LCDR1, LDR2, and LDR3 and heavy chain complementary determining regions HCDR1, HCDR2, HCDR3, and wherein the HBeAg antibody or antigen-binding fragment thereof comprises:
   (a) the LCDR1 sequence of SEQ ID NO:9;
   (b) the LCDR2 sequence of SEQ ID NO:11;
   (c) the LCDR3 sequence of SEQ ID NO:10;
   (d) the HCDR1 sequence of SEQ ID NO:12;
   (e) the HCDR2 sequence of SEQ ID NO:13; and
   (f) the HCDR3 sequence of SEQ ID NO:14.

2. The HBeAg antibody or antigen-binding fragment thereof of claim 1, wherein the HBeAg antibody is a monoclonal antibody.

3. The HBeAg antibody or antigen-binding fragment thereof of claim 1, wherein the HBeAg antibody is a chimeric antibody.

4. The HBeAg antibody or antigen-binding fragment thereof of claim 1, wherein the HBeAg antibody is a rabbit-human chimeric antibody.

5. The HBeAg antibody or antigen-binding fragment thereof of claim 1, wherein the HBeAg antibody is a humanized antibody.

6. The HBeAg antibody or antigen-binding fragment thereof of claim 1, wherein the HBeAg antibody is a bispecific antibody.

7. The HBeAg antibody or antigen-binding fragment thereof of claim 1, wherein the HBeAg antibody or antigen-binding fragment thereof is conjugated to a moiety selected from the group consisting of a growth inhibitory agent, a detectable label, an enzyme, and a cytotoxic agent.

8. The HBeAg antibody or antigen-binding fragment thereof of claim 1, wherein the HBeAg antibody or antigen-binding fragment thereof is conjugated to a solid support that includes glass, a polysaccharide, a polyacrylamide, a polystyrene, a polyvinyl alcohol, a silicone, an assay plate, or a purification column.

* * * * *